(12) United States Patent
You et al.

(10) Patent No.: US 11,773,057 B2
(45) Date of Patent: Oct. 3, 2023

(54) NAPHTHALENESULFONAMIDE COMPOUND, PREPARATION METHOD, AND APPLICATION

(71) Applicant: CHINA PHARMACEUTICAL UNIVERSITY, Jiangsu (CN)

(72) Inventors: Qidong You, Jiangsu (CN); Zhengyu Jiang, Jiangsu (CN); Yuting Liu, Jiangsu (CN); Mengchen Lu, Jiangsu (CN); Hongli Shao, Jiangsu (CN); Jing Zhao, Jiangsu (CN); Xiaoli Xu, Jiangsu (CN); Xiaoke Guo, Jiangsu (CN); Lei Wang, Jiangsu (CN)

(73) Assignee: CHINA PHARMACEUTICAL UNIVERSITY, Jiangsu (CN)

( * ) Notice: Subject to any disclaimer, the term of this patent is extended or adjusted under 35 U.S.C. 154(b) by 74 days.

(21) Appl. No.: 17/626,505

(22) PCT Filed: Apr. 13, 2020

(86) PCT No.: PCT/CN2020/084460
§ 371 (c)(1),
(2) Date: Jan. 12, 2022

(87) PCT Pub. No.: WO2021/012721
PCT Pub. Date: Jan. 28, 2021

(65) Prior Publication Data
US 2022/0251035 A1    Aug. 11, 2022

(30) Foreign Application Priority Data

Jul. 24, 2019   (CN) .......................... 201910673326.3

(51) Int. Cl.
*A61K 31/63*      (2006.01)
*C07C 311/29*     (2006.01)
(Continued)

(52) U.S. Cl.
CPC .......... *C07C 311/29* (2013.01); *A61K 31/343* (2013.01); *A61K 31/63* (2013.01); *C07D 307/79* (2013.01)

(58) Field of Classification Search
CPC ... C07C 311/29; C07C 311/21; C07C 311/46; C07D 307/79; C07D 307/82;
(Continued)

(56) References Cited

FOREIGN PATENT DOCUMENTS

| CN | 108101821 | 6/2018 |
|----|-----------|--------|
| CN | 108752245 | 11/2018 |

(Continued)

OTHER PUBLICATIONS

"International Search Report (Form PCT/ISA/210) of PCT/CN2020/084460," dated Jul. 8, 2020, with English translation thereof, pp. 1-6.

*Primary Examiner* — Taylor V Oh
(74) *Attorney, Agent, or Firm* — JCIP GLOBAL INC.

(57) ABSTRACT

Disclosed in the present invention are a naphthalenesulfonamide compound, a preparation method, and an application. The naphthalenesulfonamide compound provided by the present invention can interfere with Keap1-Nrf2 binding and activate Nrf2 to relieve inflammatory damage and improve an inflammatory microenvironment, has a potential anti-inflammatory activity, and can be used for preparing an anti-inflammatory drug for inflammatory damage of various inflammation-related diseases, including chronic obstructive pulmonary disease (COPD), Alzheimer's disease, Parkinson's disease, atherosclerosis, chronic kidney disease (CKD), diabetes, intestinal Inflammations, rheumatoid arthritis, etc.

7 Claims, 1 Drawing Sheet

(51) Int. Cl.
*C07D 307/79* (2006.01)
*A61K 31/343* (2006.01)

(58) Field of Classification Search
CPC .... Y02P 20/55; A61P 1/00; A61P 3/10; A61P 9/10; A61P 11/00; A61P 13/12; A61P 19/02; A61P 25/16; A61P 25/28; A61P 39/06; A61P 29/00; A61K 31/343; A61K 31/63
USPC .................................. 514/469, 602; 564/84
See application file for complete search history.

(56) References Cited

FOREIGN PATENT DOCUMENTS

| | | |
|---|---|---|
| CN | 110256305 | 9/2019 |
| EP | 2998294 | 3/2016 |

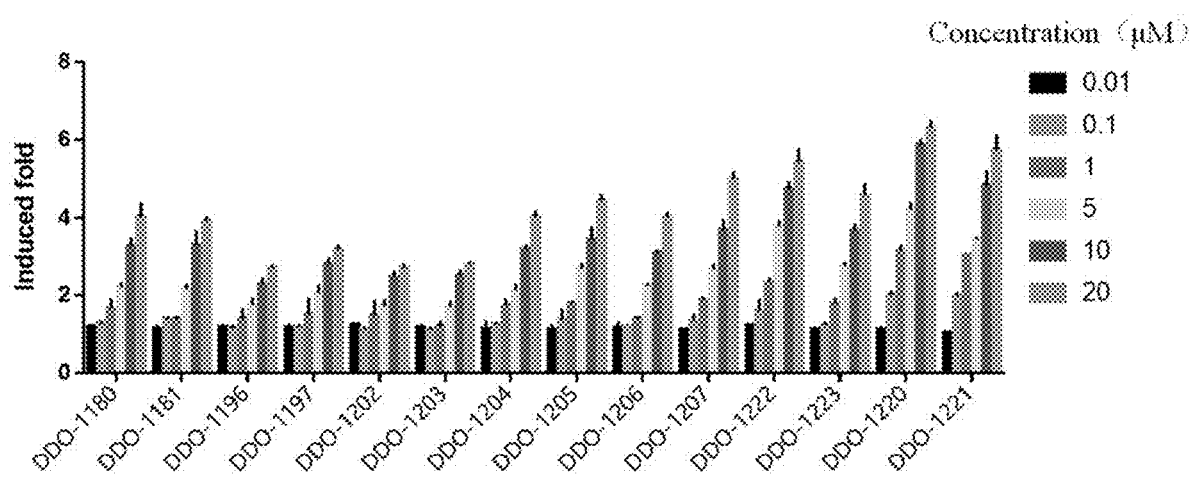

NAPHTHALENESULFONAMIDE COMPOUND, PREPARATION METHOD, AND APPLICATION

CROSS-REFERENCE TO RELATED APPLICATION

This application is a 371 of international application of PCT application serial no. PCT/CN2020/084460, filed on Apr. 13, 2020, which claims the priority benefit of China application no. 201910673326.3, filed on Jul. 24, 2019. The entirety of each of the above-mentioned patent applications is hereby incorporated by reference herein and made a part of this specification.

TECHNICAL FIELD

The present invention belongs to the field of pharmaceutical chemistry, and in particular relates to a naphthalenesulfonamide compound, a preparation method and an application.

BACKGROUND

Oxygen ($O_2$) is essential for cell energy metabolism and life systems, but reactive oxygen species (ROS) are produced during these metabolic processes. ROS plays a major role in the occurrence and development of cancer, inflammatory diseases and neurodegenerative diseases. Anti-oxidative defense systems consisting of detoxifying enzymes and anti-oxidases can attenuate the damaging effects of ROS such as superoxide dismutase (SOD), glutathione catalase (GPx), thioredoxin, HO-1, ferritin, glutathione reductase, NAD(P)H dehydrogenase (NQO1), and glutathione S transferase (GST). The antioxidant enzyme is regulated by an antioxidant response element (ARE), and a nuclear factor E2-related factor 2 (Nrf2) is one of the major ARE binding transcription factors. Previous studies have demonstrated a protective effect of Nrf2 on oxidative stress, which makes the up-regulation of Nrf2 activity a promising therapeutic strategy, particularly for inflammation and central nervous system (CNS) diseases. In the non-stress state, the cell concentration of Nrf2 is very low, and is negatively regulated by the substrate regulatory protein Kelch-like epichlorohydrin-related protein 1 (Keap1), which binds to Nrf2 in the cytoplasm and is targeted for delivery to the proteasome for ubiquitination degradation. In the oxidative stress state. Keap1 serves as an oxidation-reduction sensor and a regulator and active oxidants modify sulfhydryl groups on cysteine residues of a specific Keap1 (i.e. Cys151, Cys257, Cys273, Cys288 and Cys297). The conformation of Keap1 changes and disturbs Keap1-Nrf2 protein-protein interaction (PPI), thereby blocking the process of Nrf2 ubiquitination. Nrf2 then accumulates and transfers to the nucleus to form a transcription factor complex, binds to the region of the ARE promoter, and induces the expression of an antioxidase gene. Therefore, the Keap1-Nrf2 PPI inhibitor can be used as a therapeutic means for increasing the antioxidant capacity in the oxidative stress state.

It has been found through a large amount of literature research that Keap1-Nrf2 PPI inhibitors activate Nrf2 and thus have great therapeutic potential for anti-inflammatory diseases, neurodegenerative diseases, respiratory diseases and the like. There are many early research results on an inhibitor of covalently modified Keap1, and drugs have been marketed (dimethyl fumarate), but such drugs lack selectivity and are potentially toxic. In contrast, the Keap1-Nrf2 PPI inhibitors have become a research hotspot in this field due to its advantages such as clear in targeting, non-easy off-targeting, and reversible competitive binding. Among the Keap1-Nrf2 PPI inhibitors, small-molecule PPI inhibitors have the advantages of lower cost, chemical stability, and good bioavailability, and have become the mainstream research direction.

As a Keap1-Nrf2 PPI small molecule inhibitor, a compound DDO-1002 (a chemical structure thereof is as follows) is obtained as a most active compound by early research in our research group, and has a relatively high affinity for Keap1, but the presence of dicarboxylic group results in a relatively large molecular polarity, which is not conducive to membrane permeation, and results in a relatively poor cell activity thereof. The research group designed and synthesized a series of naphthalenesulfonamide Keap1-Nrf2 PPI small molecule inhibitors comprising β amino acid structure by adopting a series of strategies to reduce the polar surface area of the molecule, such as breaking the symmetry structure and removing the sulfonamide structure on one side, among which DDO-1146 (chemical structure is as follows) has better activity, but DDO-1146 still has a great difference from DDO-1002, and due to the presence of dicarboxyl groups, the molecular polarity of DDO-1146 is still relatively large. Therefore, the present subject designs and synthesizes Keap1-Nrf2 PPI inhibitors with high activity and improved physical and chemical properties by adopting DDO-1146 as a lead compound by adopting structure-based drug design strategies and systematic structure-activity relationship studies, enriches the structure types of the Keap1-Nrf2 PPI inhibitor, and provides more choices for targeting Keap1-Nrf2 PPI.

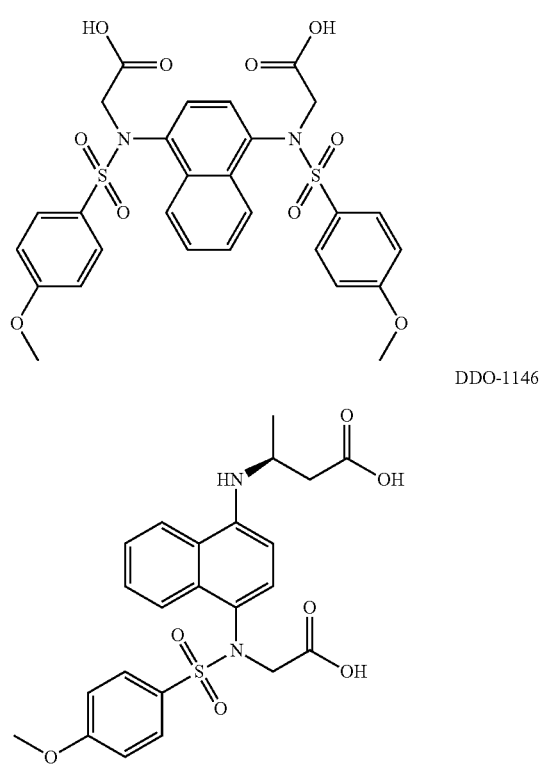

Therefore, the present invention has been specifically proposed.

SUMMARY

An objective of the present invention is to overcome disadvantages of the prior art, and provide a naphthalenesulfonamide compound, a preparation method and an application.

The described object of the present invention is achieved by the following technical solution:

A naphthalenesulfonamide compound, wherein the chemical structure thereof is represented by general formula I, II, III, IV, V or VI:

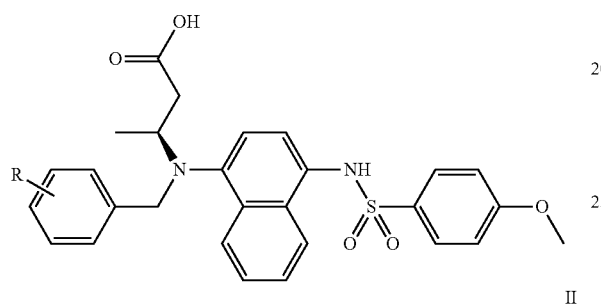

I

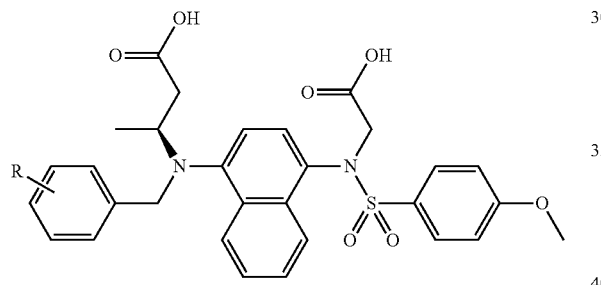

II wherein in general formula I or II, a substituent R is:

| General formula | Substituent R | General formula II-number | Substituent |
|---|---|---|---|
| DDO-1160 | —H | DDO-1161 | —H |
| DDO-1162 | 4-CH$_3$ | DDO-1163 | 4-CH$_3$ |
| DDO-1164 | 4-Cl | DDO-1165 | 4-Cl |
| DDO-1166 | 4-F | DDO-1167 | 4-F |
| DDO-1168 | 3-CH$_3$ | DDO-1169 | 3-CH$_3$ |
| DDO-1170 | 2-CH$_3$ | DDO-1171 | 2-CH$_3$ |
| DDO-1172 | 3-Cl | DDO-1173 | 3-Cl |
| DDO-1174 | 2-Cl | DDO-1175 | 2-Cl |
| DDO-1176 | 3-F | DDO-1177 | 3-F |
| DDO-1178 | 2-F | DDO-1179 | 2-F |

We performed a target activity test on compound DDO-1160~DDO-1179 by using a fluorescence polarization based Keap1-Nrf2 PPI competitive inhibition experiment (FP experiment), and the results are shown in the following table:

| Number | Substituent R | IC$_{50}$ (μM) | Number | Substituent R | IC$_{50}$ (μM) |
|---|---|---|---|---|---|
| DDO-1160 | —H | 0.86 | DDO-1161 | —H | 0.108 |
| DDO-1162 | 4-CH$_3$ | 1.91 | DDO-1163 | 4-CH$_3$ | 0.152 |
| DDO-1164 | 4-Cl | 4.10 | DDO-1165 | 4-Cl | 0.272 |
| DDO-1166 | 4-F | 2.15 | DDO-1167 | 4-F | 0.176 |
| DDO-1168 | 3-CH$_3$ | 1.66 | DDO-1169 | 3-CH$_3$ | 0.205 |
| DDO-1170 | 2-CH$_3$ | 1.09 | DDO-1171 | 2-CH$_3$ | 0.113 |
| DDO-1172 | 3-Cl | 3.78 | DDO-1173 | 3-Cl | 0.180 |
| DDO-1174 | 2-Cl | 1.60 | DDO-1175 | 2-Cl | 0.109 |
| DDO-1176 | 3-F | 2.47 | DDO-1177 | 3-F | 0.180 |
| DDO-1178 | 2-F | 0.46 | DDO-1179 | 2-F | 0.075 |

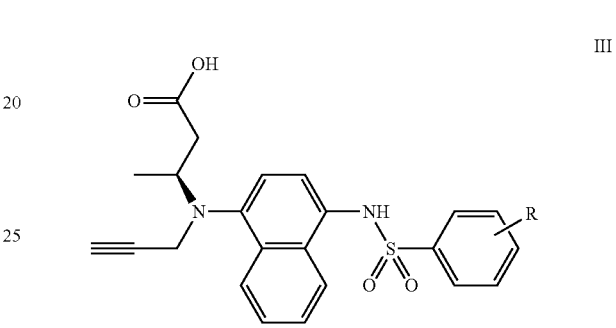

III

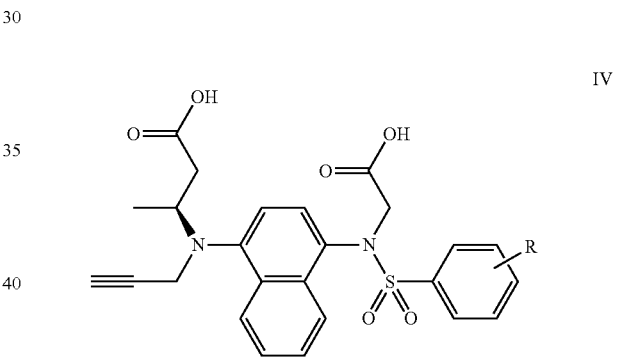

IV wherein in general formula III or IV, a substituent R is:

| General formula III | Substituent R | General formula IV | Substituent R |
|---|---|---|---|
| DDO-1186 | H | DDO-1187 | H |
| DDO-1188 | 4-NHCOCH$_3$ | DDO-1189 | 4-NHCOCH$_3$ |
| DDO-1180 | 4-OCH$_3$ | DDO-1181 | 4-OCH$_3$ |
| DDO-1190 | 4-F | DDO-1191 | 4-F |
| DDO-1192 | 4-Cl | DDO-1193 | 4-Cl |
| DDO-1194 | 4-CH(CH$_3$)$_2$ | DDO-1195 | 4-CH(CH$_3$)$_2$ |
| DDO-1196 | 4-CH$_3$ | DDO-1197 | 4-CH$_3$ |
| DDO-1198 | 2-OCH$_3$ | DDO-1199 | 2-OCH$_3$ |
| DDO-1200 | 3-OCH$_3$ | DDO-1201 | 3-OCH$_3$ |
| DDO-1202 | 2-CH$_3$ | DDO-1203 | 2-CH$_3$ |
| DDO-1204 | 2,4-CH$_3$ | DDO-1205 | 2,4-CH$_3$ |
| DDO-1206 | 2,4,6-CH$_3$ | DDO-1207 | 2,4,6-CH$_3$ |
| DDO-1208 | 2,3,5,6-CH$_3$ | DDO-1209 | 2,3,5,6-CH$_3$ |

We performed a target activity test on compound DDO-1186~DDO-1209 by using a fluorescence polarization based Keap1-Nrf2 PPI competitive inhibition experiment (FP experiment), and the results are shown in the following table:

| General formula | Substituent R | IC$_{50}$ | General formula | Substituent | IC$_{50}$ (μM) |
|---|---|---|---|---|---|
| DDO-1186 | H | 8 | DDO-1187 | H | 3 |
| DDO-1188 | 4-NHCOCH$_3$ | 1.46 | DDO-1189 | 4-NHCOC | 0.63 |
| DDO-1180 | 4-OCH$_3$ | 0.095 | DDO-1181 | 4-OCH$_3$ | 0.068 |
| DDO-1190 | 4-F | 4 | DDO-1191 | 4-F | 2 |
| DDO-1192 | 4-Cl | 1.7 | DDO-1193 | 4-Cl | 0.95 |
| DDO-1194 | 4-CH(CH$_3$)$_2$ | 0.48 | DDO-1195 | 4-CH(CH$_3$) | 0.11 |
| DDO-1196 | 4-CH$_3$ | 0.22 | DDO-1197 | 4-CH$_3$ | 0.080 |
| DDO-1198 | 2-OCH$_3$ | 2 | DDO-1199 | 2-OCH$_3$ | 0.29 |
| DDO-1200 | 3-OCH$_3$ | 0.24 | DDO-1201 | 3-OCH$_3$ | 0.13 |
| DDO-1202 | 2-CH$_3$ | 0.24 | DDO-1203 | 2-CH$_3$ | 0.17 |
| DDO-1204 | 2,4-CE$_3$ | 0.093 | DDO-1205 | 2,4-CE$_3$ | 0.027 |
| DDO-1206 | 2,4,6-CH$_3$ | 0.041 | DDO-1207 | 2,4,6-CH$_3$ | 0.015 |
| DDO-1208 | 2,3,5,6-CH$_3$ | 1 | DDO-1209 | 2,3,5,6-CH | 0.15 |

| Number | Substituent | IC$_{50}$ (nM) |
|---|---|---|
| DDO-1210 | 3-OMe | 72 |
| DDO-1211 | 3-OMe | 59 |
| DDO-1212 | 3-F | 277 |
| DDO-1213 | 3-F | 155 |
| DDO-1214 | 3-Cl | 75 |
| DDO-1215 | 3-Cl | 40 |
| DDO-1216 | 3-Me | 72 |
| DDO-1217 | 3-Me | 37 |
| DDO-1218 | 2,3,6-3Me | 23 |
| DDO-1219 | 2,3,6-3Me | 7.1 |
| DDO-1220 | 2,6-2Me | 13 |
| DDO-1221 | 2,6-2Me | 5.8 |
| DDO-1222 | (2,3-dihydrobenzofuran-5-yl) | 160 |
| DDO-1223 | (2,3-dihydrobenzofuran-5-yl) | 86 |

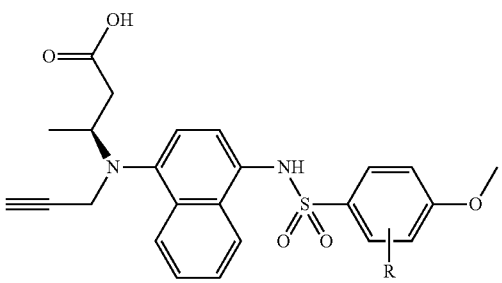

V

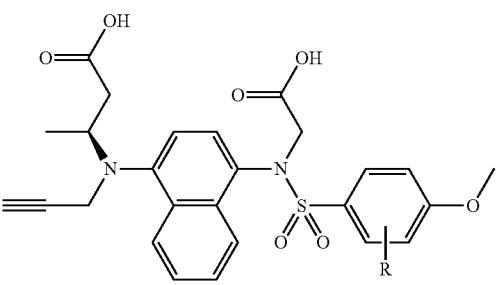

VI wherein, in general formula V or VI, a substituent R is:

| General formula V-number | Substituent R | General formula VI-number | Substituent R |
|---|---|---|---|
| DDO-1210 | 3-OMe | DDO-1211 | 3-OMe |
| DDO-1212 | 3-F | DDO-1213 | 3-F |
| DDO-1214 | 3-Cl | DDO-1215 | 3-Cl |
| DDO-1216 | 3-Me | DDO-1217 | 3-Me |
| DDO-1218 | 2,3,6-3Me | DDO-1219 | 2,3,6-3Me |
| DDO-1220 | 2,6-2Me | DDO-1221 | 2,6-2Me |
| DDO-1222 | (2,3-dihydrobenzofuran-5-yl) | DDO-1223 | (2,3-dihydrobenzofuran-5-yl) |

We performed a target activity test on compound DDO-1210~DDO4223 by using a fluorescence polarization based Keap1-Nrf2 PPI competitive inhibition experiment (FP experiment), and the results are shown in the following table:

A method for preparing a compound represented by general formula I or II, comprising the following steps:

performing nucleophilic substitution with 1-nitronaphthalene as a raw material to obtain a compound 18, and then reacting the compound 18 with Tf$_2$O to obtain a compound 19 having an easy leaving group; performing Buchwald-Hartwig C—N coupling reaction on the compound 19 and (S)-methyl aminobutyrate hydrochloride to obtain an intermediate 20; performing nitro reduction on the intermediate 20 in the presence of Pd/C and H$_2$ to obtain an intermediate 21; reacting the intermediate 21 with di-tert-butyl dicarbonate to obtain an intermediate 22; reacting the intermediate 22 with benzyl bromide in the presence of K$_2$CO$_3$ and NaI to obtain an intermediate 23; removing Boc of the intermediate 23 with trifluoroacetic acid to an intermediate 24, and reacting the intermediate 24 with 4-methoxybenzene sulfonyl chloride to obtain a key intermediate 25; and reacting the intermediate 25 with methyl bromoacetate in the presence of K$_2$CO$_3$ to obtain a compound 26, and demethylating the compound 26 in the presence of LiOH to obtain a diacid compound of general formula II, or demethylating the intermediate 25 in the presence of LiOH to obtain a mono-acid compound of general formula I; a synthetic route is as follows:

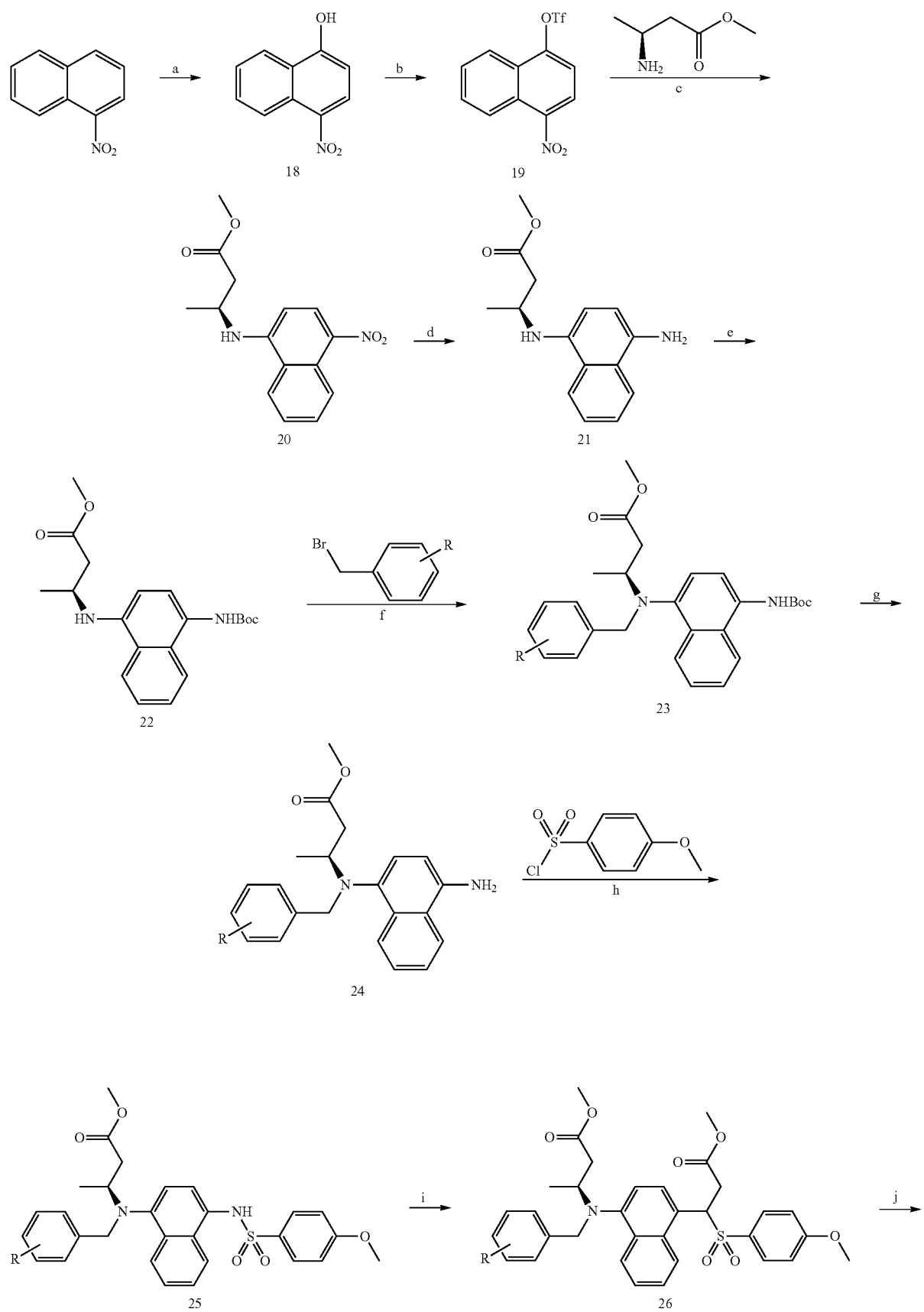

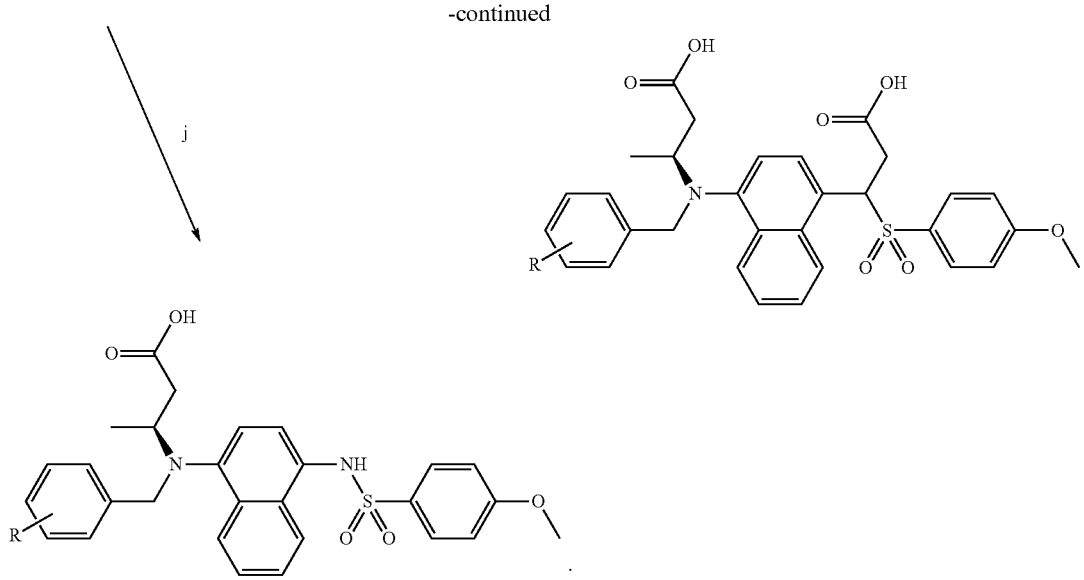

Reaction parameters in synthetic route: (a) tBu-COOH, KOH, DMSO/H₂O, rt. 4 h; (b) Tf₂O, Et₂N, DCM, r.t. 2 h; (c) Pd₂(dba)₃, BINAP, Cs₂CO₃, DIPEA, dioxane, 100° C., 20 h; (d) H₂, Pd/C, THF, r.t. 4-6 h; (e) boc₂O, EtOH, 8 h; (f) K₂CO₃, NaI, DMF, 100° C., 24 h; (g) CF₃COOH, DCM, rt. 2 h; (h) Py, THF, 70° C., 4 h; (i) K₂CO₃, DMF, r.t. 2 h; LiOH, MeOH/H₂O, rt. 10 h.

A method for preparing a compound represented by general formula III or IV, comprising the following steps:
performing nucleophilic substitution with 1-nitronaphthalene as a raw material to obtain a compound 18, and then reacting the compound 18 with Tf₂O to obtain a compound 19 having an easy leaving group; performing Buchwald-Hartwig C—N coupling reaction on the compound 19 and (S)-methyl aminobutyrate hydrochloride to obtain an intermediate 20; performing nitro reduction on the intermediate 20 in the presence of Pd/C and H₂ to obtain an intermediate 21; reacting the intermediate 21 with di-tert-butyl dicarbonate to obtain an intermediate 22; reacting the intermediate 22 with propargyl bromide in the presence of K₂CO₃ and NaI to obtain an intermediate 35; removing Boc of the intermediate 35 with trifluoroacetic acid to an intermediate 36, and reacting the intermediate 36 with benzene sulfonyl chloride with different substituents to obtain a key intermediate 37; and reacting the intermediate 37 with methyl bromoacetate in the presence of K₂CO₃ to obtain a compound 38, and demethylating the compound 38 in the presence of LiOH to obtain a diacid compound of general formula IV, or demethylating the intermediate 37 in the presence of LiOH to obtain a mono-acid compound of general formula III; a synthetic route is as follows:

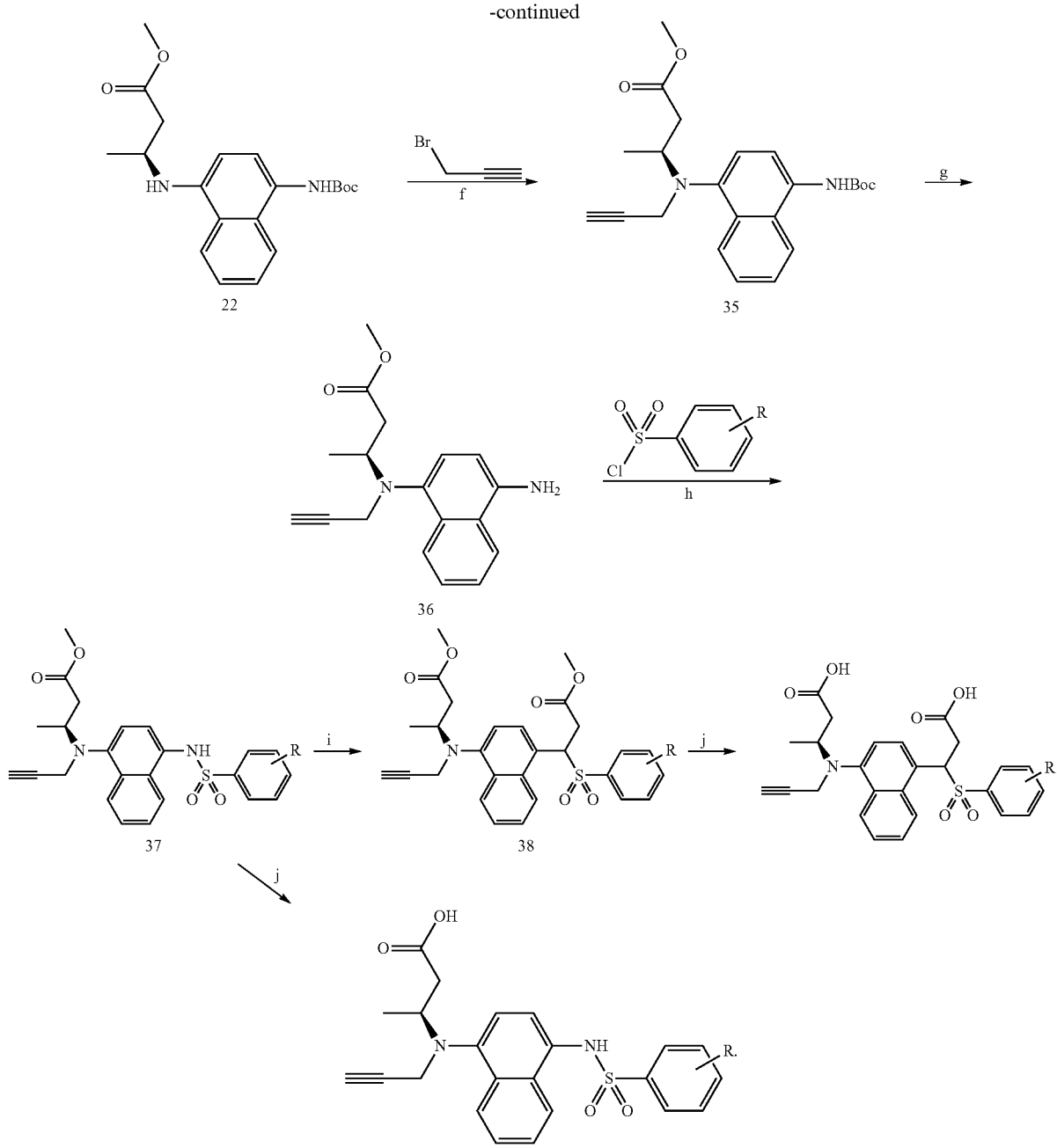

Reaction parameters in synthetic route: (a) tBu-COOH, KOH, DMSO/H₂O, r.t. 4 h; (b) Tf₂O, Et₃N, DCM, r.t. 2 h; (c) Pd₂(dba)₃, Cs₂CO₃, DIPEA, dioxane, 100° C., 20 h; (d) H₂, Pd/C, THF, r.t. 4-6 h; (e) boc₂O, EtOH, 8 h; (f) K₂CO₃, NaI, DMF, 100° C., 24 h; (g) CF₃COOH, DCM, r.t. 2 h; (h) Py, THF, 70° C., 4 h; (i) K₂CO₃, DMF, rt. 2 h; (j) LiOH, MeOH/H₂O, rt. 10 h.

A method for preparing a compound represented by general formula V or VI, comprising the following steps:
performing nucleophilic substitution with 1-nitronaphthalene as a raw material to obtain a compound 18, and then reacting the compound 18 with Tf₂O to obtain a compound 19 having an easy leaving group; performing Buchwald-Hartwig C—N coupling reaction on the compound 19 and (S)-methyl aminobutyrate hydrochloride to obtain an intermediate 20; performing nitro reduction on the intermediate 20 in the presence of Pd/C and H₂ to obtain an intermediate 21; reacting the intermediate 21 with di-tort-butyl dicarbonate to obtain an intermediate 22; reacting the intermediate 22 with propargyl bromide in the presence of K₂CO₃ and NaI to obtain an intermediate 35; removing Boc of the intermediate 35 with trifluoroacetic acid to an intermediate 36, and reacting the intermediate 36 with 4-methoxybenzenesulfonyl chloride with different substituents to obtain a key intermediate 39; and reacting the intermediate 39 with methyl bromoacetate in the presence of K₂CO₃ to obtain a compound 40, and demethylating the compound 40 in the presence of LiOH to obtain a diacid compound of general formula VI, or demethylating the intermediate 39 in the presence of LiOH to obtain a mono-acid compound of general formula V; a synthetic route is as follows:

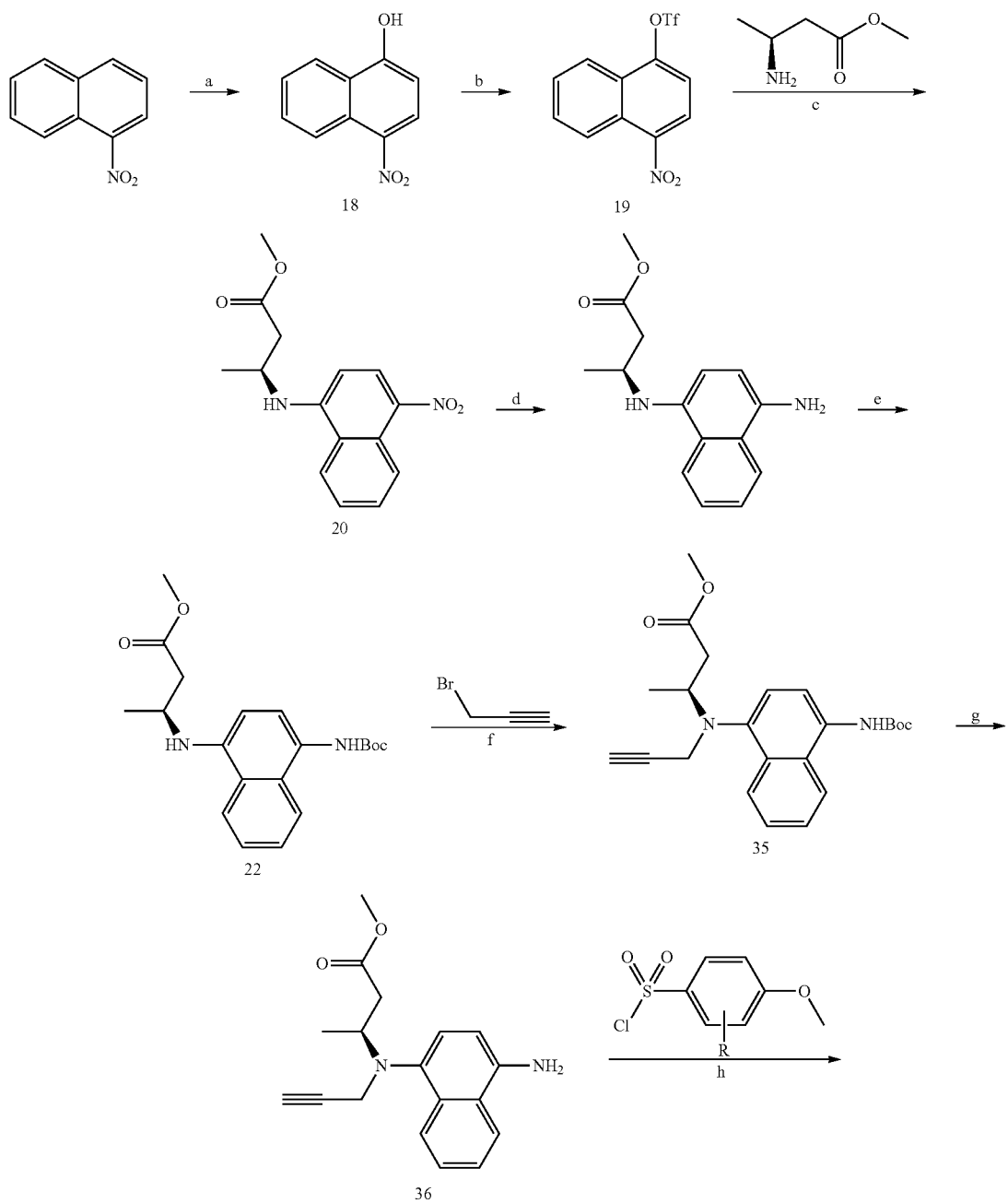
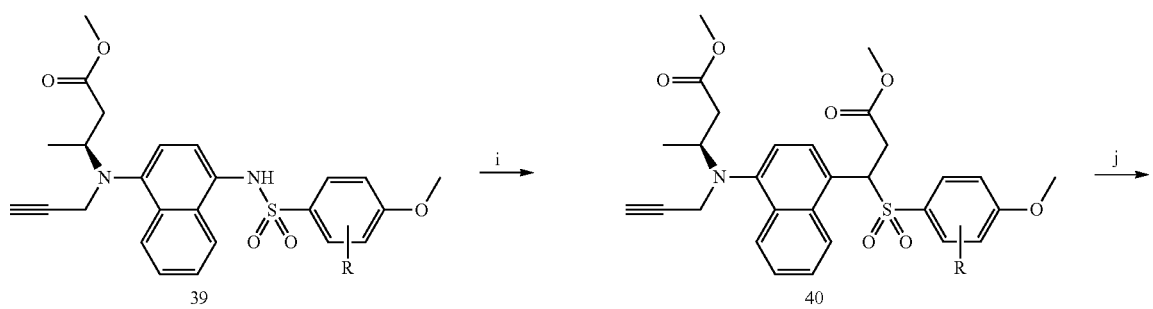

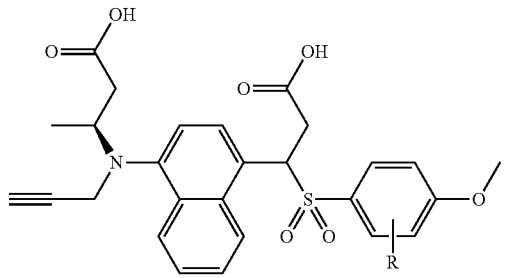

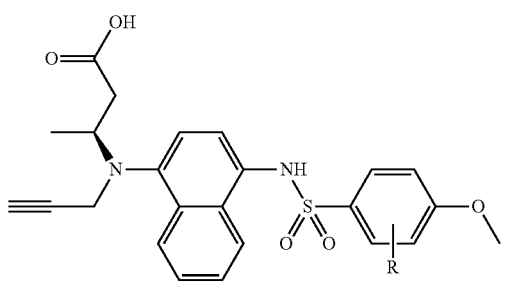

Reaction parameters in synthetic route: (a) tBu-COOH, KOH, DMSO/H$_2$O, r.t. 4 h; (b) Tf$_2$O, Et$_3$N, DCM, r.t. 2 h; (c) Pd$_2$(dba)$_3$, BINAP, Cs$_2$CO$_3$, DIPEA, dioxane, 100° C., 20 h; (d) H$_2$, Pd/C, Et. 4-6 h; (e) boc$_2$O, EtOH, 8 h; (f) K$_2$CO$_3$, NaI DMF, 100° C., 24 h; (g) CF$_3$COOH, DCM, r.t. 2 h; (h) Py, THF, 70° C., 4 h; (i) K$_2$CO$_3$, DMF, r.t. 2 h; LiOH, MeOH/H$_2$O, r.t. 10 h.

A pharmaceutically acceptable salt of the naphthalenesulfonamide compound.

Use of the naphthalenesulfonamide compound and the pharmaceutically acceptable salt thereof in preparation of a Keap1-Nrf2 protein-protein interaction inhibitor.

Use of the naphthalenesulfonamide compound and the pharmaceutically acceptable salt thereof in preparation of a drug for increasing the antioxidant capacity under an oxidative stress state.

Use of the naphthalenesulfonamide compound and the pharmaceutically acceptable salt thereof in preparation of a drug for treating or alleviating inflammation of a disease.

Further, the disease is an inflammatory disease or a neurodegenerative disease, comprising chronic obstructive pulmonary disease, Alzheimer's disease, Parkinson's disease, atherosclerosis, chronic kidney disease, diabetes, intestinal inflammation, and rheumatoid arthritis.

Beneficial Effects:

The naphthalenesulfonamide compound provided by the disclosure can interfere with the binding of Keap1-Nrf2 and activate Nrf2, thereby alleviating inflammatory damage, improving the inflammatory microenvironment. The naphthalenesulfonamide compound has potential anti-inflammatory activity, and can be prepared into anti-inflammatory drugs for inflammatory damage of many inflammation-related diseases, including chronic obstructive pulmonary disease (COPD), Alzheimer's disease, Parkinson's disease, atherosclerosis, chronic kidney disease (CKD), diabetes, intestinal inflammation, rheumatoid arthritis, and the like.

BRIEF DESCRIPTION OF THE DRAWINGS

FIG. 1 is the ARE luciferase reporter gene activity (fold induction) of selected compounds.

DETAILED DESCRIPTION OF THE EMBODIMENTS

The present invention is hereinafter described in detail with reference to embodiments, but is not intended to limit the scope of protection of the present invention.

Example 1: Synthesis and Structural Confirmation of Compound

1. General Experimental Rules

The chemical reagents used in the present invention are commercially available chemical pure or analytical pure. Melting points are determined using a M. P.50 Melting Point System (the thermometer is uncorrected). $^1$H-NMR, $^{13}$C-NMR spectra are determined by Bruker AV300 (300 MHz) nuclear magnetic resonance spectrometer (TMS is an internal standard, and the mass spectrum is determined by Agilent 1946 A-MSD type mass spectrometer (ESI-MS) and Water Q-Tof mass spectrometer (HRMS). The purity is determined by HPLC. The chromato-graphic column is an Agilent C18 (4.6×150 mm, 3.5 μM) reverse phase column. The mobile phase is methanol:water:trifluoroacetic acid=85:15:0.1.

The solvent is concentrated by an N-1100 rotary evaporator (carried out at 40° C.) manufactured by EYELA Instruments Co., Ltd. Silica gel used for column chromatography is 200-300 mesh silica gel (Qingdao Marine Chemical Factory, division factory), and the eluent is petroleum ether (boiling range of 60-90° C.) and ethyl acetate. The reaction is monitored by a GF254 thin-layer chromatography silica gel plate (Nicotiana deli) of 0.25×0.75 mm specification, and ultraviolet absorption is detected by irradiation with ZF-1 three purpose ultraviolet analyzer (Hangzhou David Science and Education instrument Co., Ltd.).

II. Preparation of Intermediates

Synthesis of 4-nitro-1-naphthol (41)

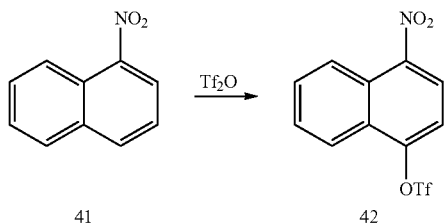 [SMILES: "Tf2O" ; O=[N+]([O-])c1cccc2ccccc12 ; O=[N+]([O-])c1ccc(OS(=O)(=O)C(F)(F)F)c2ccccc12]

1-Nitronaphthalene (8.50 g, 49.10 mmol) is dissolved in 2000 mL of DMSO (dimethyl sulfoxide), then potassium hydroxide (11.00 g, 196.30 mmol) is dissolved in 10.00 mL of water and added dropwise to a reaction system under an ice bath, and finally a solution of 10.00 mL of DMSO in which tert-butylperoxy alcohol (9.80 mL, 98.20 mmol) is dissolved is added dropwise to the reaction system. After the addition is complete, the mixture is stirred for about 10 minutes, the ice bath is removed, and the reaction is allowed to proceed at room temperature. After reaction for 4 h, $Na_2S_2O_3$ (1.50 g, 9.30 mmol) is added and stirred for 1 h, then 200.00 mL of water is added, the pH is adjusted with dilute hydrochloric acid to 4 so as to precipitate a large amount of a yellow solid, followed by filtering and retaining the filter cake, then the pH of the filter cake is adjusted with 2 M sodium hydroxide to 9-10, and the pH of the aqueous layer is adjusted with dilute hydrochloric acid solution to 4 so as to precipitate a yellow solid, followed by filtering and drying to obtain a bright yellow solid 41 of 5.20 g with a yield of 72.5%; m.p. 156-159° C.; $^1$H-NMR (300 MHz, DMSO-$d_6$) δ: 6.98 (d, 1H, J=8.70 Hz), 7.61-7.66 (m, 1H), 7.78-7.83 (m, 1H), 8.33 (d, 1H, J=8.34 Hz), 8.42 (d, 1H, J=8.70 Hz), 8.68 (d, J=8.79 Hz), 11.98 (br, 1H); ESI-MS m/z: 190.0 [M+H]$^+$.

Synthesis of 4-nitronaphthalen-1-yl trifluoromethanesulfonate (42)

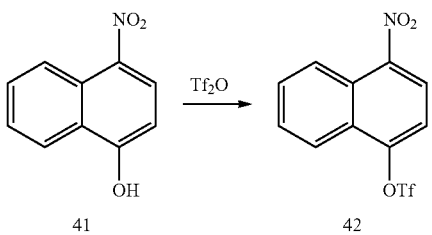 [SMILES: "Tf2O" ; O=[N+]([O-])c1ccc(O)c2ccccc12 ; O=[N+]([O-])c1ccc(OS(=O)(=O)C(F)(F)F)c2ccccc12]

4-nitro-1-naphthol 41 (2.00 g, 10.60 mmol) is dissolved in 20.00 mL DCM, $Et_3N$ (4.40 mL, 31.90 mmol) and $Tf_2O$ (2.70 mL, 16.30 mmol) are added successively in an ice bath, after the addition was completed, the reaction system is left at room temperature and stirred for 2 h until TLC monitors the reaction to be complete. The reaction is neutralized with saturated $NaHCO_3$ (20.00 mL), and the organic phase is washed twice with water (20.00 mL) and washed twice with saturated NaCl (20.00 mL). Finally, the organic phase is dried with anhydrous $Na_2SO_4$, the organic solvent is spin-dried to make sand directly, and is purified by column chromatography, so as to obtain 2.00 g of pale yellow solid 42 with a yield of 56%, m. p. 59-61° C.; ESI-MS 321.99 [M+H]$^-$.

Synthesis of (S)-methyl 3-((4-nitronaphthalen-1-yl) amino) butanoate (43)

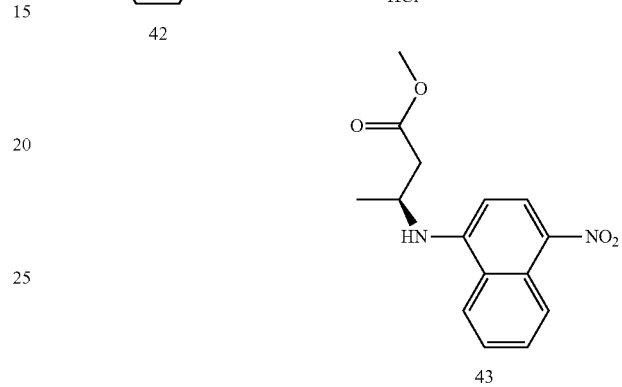

Compound 42 (2 g, 6.22 mmol) and (S)-methyl aminobutyrate hydrochloride (1.14 g, 7.46 mmol) are added to a reaction vial, followed by quick addition of $Cs_2CO_3$ (4.00 g, 12.44 mmol), (±)-BINAP (0.58 g, 0.94 mmol) and $Pd_2(dba)_3$ (0.28 g, 0.32 mmol), and finally, in time, DIPEA (2.2.0 mL, 12.44 mmol) and toluene (20.00 mL), and heating under nitrogen for 100° C. for 20 h of reaction. The reaction is cooled to room temperature, the reaction solution is filtered through Celite, the filtrate is spin-dried to make sand directly, and is purified by column chromatography, so as to obtain a yellow oily liquid 43 of 1.10 g with a yield of 61%; $^1$H NMR (300 MHz, Chloroform-d) δ 9.06 (d, J=8.8 Hz, 1H), 8.51 (d, J=8.9 Hz, 1H), 7.89 (d, J=8.5 Hz, 1H), 7.74 (t, J=7.9 Hz, 1H), 7.58 (t, J=7.7 Hz, 1H), 6.58 (d, J=8.9 Hz, 1H), 6.08 (d, J=8.2 Hz, 1H), 4.35-4.20 (m, 1H), 3.79 (s, 3H), 2.78 (t, J=4.2 Hz, 2H), 1.31 (d, J=8.4 Hz, 3H); ESI-MS m/z: 289.1 [M+H]$^+$.

Synthesis of (S)-methyl 3-((4-aminonaphthalen-1-yl) amino) butanoate (44)

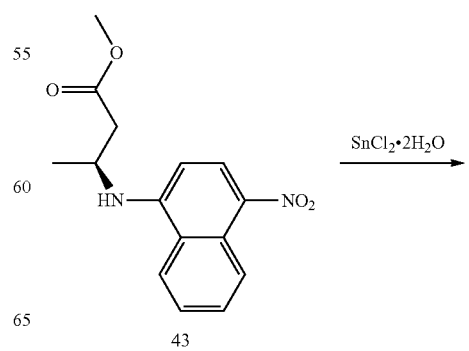

-continued

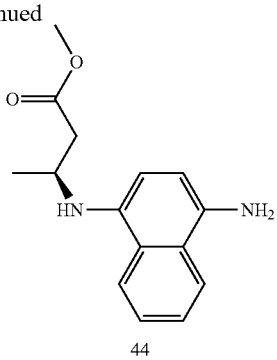

44

Compound 43 (1.10 g, 3.81 mmol) is added to a reaction vial and dissolved in 20.00 mL of ethyl acetate, stannous chloride dihydrate (3.45 g, 15.26 mmol) is added, and the reaction is carried out at 78° C. for 4 h. After TLC monitors the reaction to be complete, the reaction is cooled to room temperature. Saturated NaHCO₃ is added to adjust the pH to weakly alkaline pH of 7-8. The reaction solution is filtered through a sand core funnel, the filter cake is washed with the ethyl acetate until no ultraviolet absorption is performed. The filtrate is layered, and the water layer is discarded. The organic layer is washed twice with saturated NaCl solution, and dried with anhydrous sodium sulfate, and concentration is performed under reduced pressure, so as to obtain a brown oily liquid 44 of 0.83 g with a yield of 85%, and the brown oily liquid 44 is directly added into the next step.

Synthesis of (S)-methyl 3-((4-((tert-butoxycarbonyl) amino) naphthalen-1-yl) amino) butanoate (45)

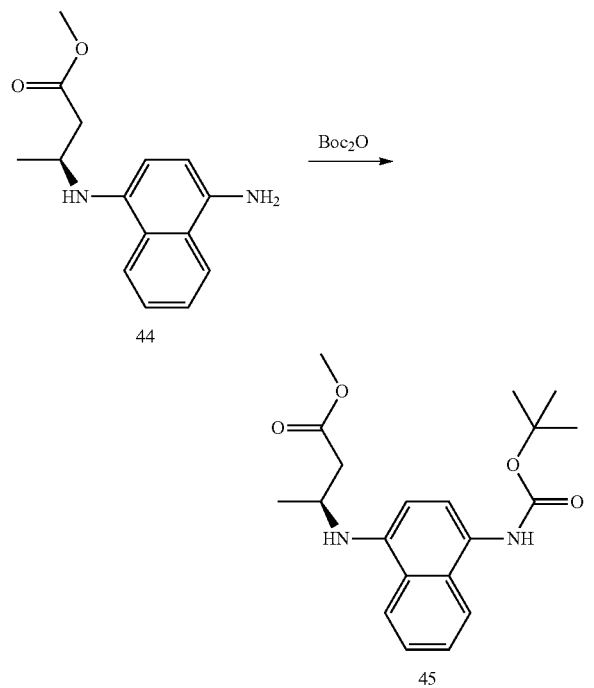

Compound 44 (0.83 g, 3.22 mmol) is dissolved in 10.00 mL of ethanol to which di-tert-butyl dicarbonate (0.77 g, 3.54 mmol) is added, and stirred at room temperature for 4 h. After TLC monitored the reaction to be complete, the organic solvent is spin-dried to make sand directly, and is purified by column chromatography, so as to obtain a dark blue oily liquid 45 of 0.96 g with a yield of 87%; ¹H NMR (300 MHz, Chloroform-d) δ 7.93-7.81 (m, 2H), 7.55-7.44 (m, 3H), 6.65 (d, J=8.2 Hz, 1H), 6.43 (s, 1H), 4.67 (s, 1H), 4.12 (q, J=6.3 Hz, 1H), 3.72 (s, 3H), 2.78 (dd, J=15.2, 4.9 Hz, 1H), 2.64-2.56 (m, 1H), 1.55 (s, 9H), 1.41 (d, J=6.3 Hz, 3H); ESI-MS m/z: 359.2 [M+H]⁺.

III. Synthesis of Benzyl-Substituted Compounds

Synthesis of (S)-methyl 3-(benzyl(4-(tert-butoxycarbonyl) amino) naphthalen-1yl) amino butanoate (46)

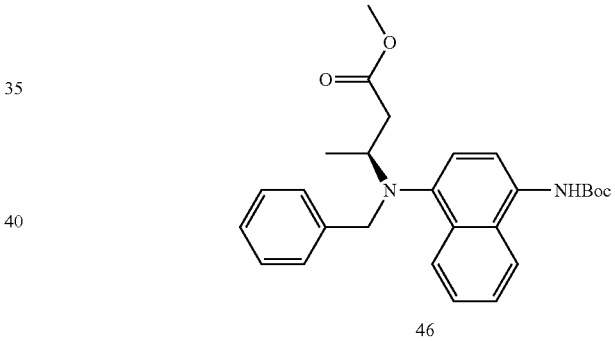

Compound 45 (0.50 g, 1.40 mmol) is added to a reaction vial, dissolved in 5.00 mL of DMSO, benzyl bromide (0.71 g, 4.20 mmol), K₂CO₃ (1.16 g, 8.40 mmol) and NaI (1.26 g, 8.40 mmol) are added. After nitrogen protection, the reaction is performed at 100° C. for 24 h. After TLC monitors the reaction to be complete, the reaction is cooled to room temperature, 10.00 ml of water is added, extraction is performed three times with EA (30.00 mL), the organic phase is combined and washed twice with saturated aqueous NaCl (30.00 mL), then the organic phase is dried with anhydrous Na₂SO₄ to make sand directly, and is purified by column chromatography so as to obtain a yellow liquid oil 46 of 0.31 g with a yield of 49%; ¹H NMR (300 MHz, Chloroform-d) δ 8.48-8.38 (m, 1H), 7.84 (dd, J=7.6, 2.2 Hz, 1H), 7.54 (td, J=7.5, 1.6 Hz, 2H), 7.37 (dd, J=12.6, 2.2 Hz, 2H), 7.23-7.06 (m, 5H), 6.66 (s, 1H), 4.42 (d, J=2.7 Hz, 2H), 3.92 (dt, J=9.0, 6.2 Hz, 1H), 3.62 (s, 3H), 2.87 (dd, J=14.4, 5.3 Hz, 1H), 2.52 (dd, J=14.5, 8.8 Hz, 1H), 1.53 (s, 9H), 1.41 (s, 3H); EST-MS m/z: 449.2 [M+H]⁺.

Synthesis of (S)-methyl 3-((4-aminonaphthalen-1-yl(benzyl) amino) butanoate (47)

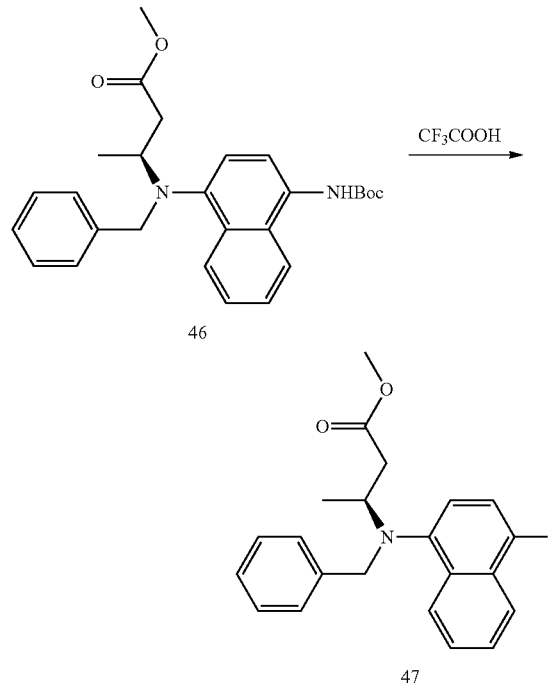

Compound 46 (0.31 g, 0.69 mmol) is added into a reaction vial, dissolved in 5.00 mL of DCM, trifluoroacetic acid (051 mL, 6.90 mmol) is added, stirred at room temperature for 2 h. After TLC monitors the reaction to be complete, the solvent is dried under reduced pressure, ethyl acetate (30.00 mL) is added to dissolve the solution, the pH is adjusted to weakly basic with saturated NaHCO$_3$ (about 8), the solution was divided, the aqueous layer is discarded, the organic phase is washed twice with saturated NaCl aqueous solution (10.00 mL), then the organic phase is dried with anhydrous Na$_2$SO$_4$, the organic phase is dried under reduced pressure to obtain a brown oily liquid 47 of 0.20 g with a yield of 82%.

Synthesis of (S)-methyl 3-((4-((4methoxyphenyl) sulfonamido) naphthalen-1-yl) (benzyl) amino) butanoate (48)

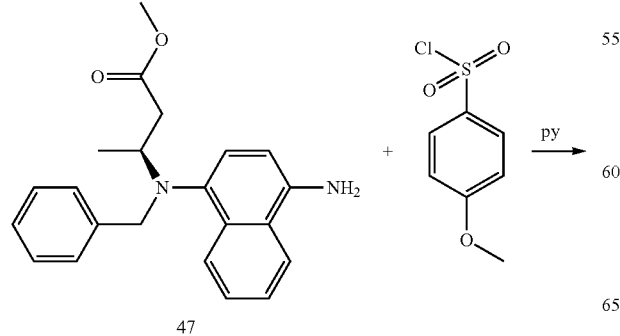

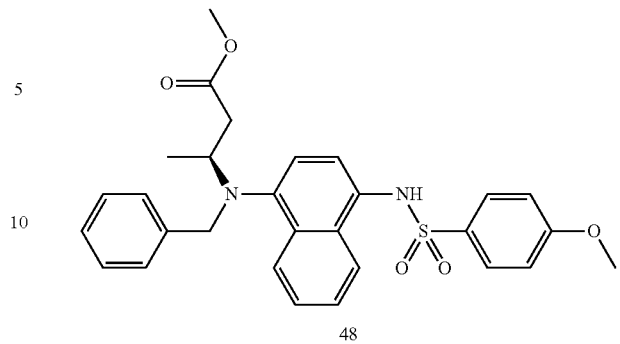

Compound 47 (0.20 g, 0.57 mmol) is added to a reaction vial, dissolved in 10.00 mL THF, and 4-methoxybenzenesulfonyl chloride (0.14 g, 069 mmol), pyridine (0.14 g, 1.72 mmol) is added; after protection with nitrogen, reaction is carried out at 70° C. for 8 h. After TLC monitors the reaction to be complete, the solvent is removed by vortexing under reduced pressure, ethyl acetate (30.00 mL) is added to dissolve, the organic phase is washed twice with 1 M HCl (10.00 mL) and washed twice with saturated aqueous NaCl (10.00 mL), then the organic phase is dried with anhydrous Na$_2$SO$_4$, is spin-dried to make sand directly and is purified by column chromatography so as to obtain a pale yellow oily liquid 48 of 0.21 g with a yield of 71%; $^1$H NMR (300 MHz, Chloroform-d) δ 8.33 (d, J=8.4 Hz, 1H), 7.76 (d, J=8.4 Hz, 1H) 7.58-7.44 (m, 3H), 7.44-7.34 (m, 1H), 7.32-7.29 (m, 1H), 7.27 (s, 1H), 7.20-6.99 (m, 5H), 6.79-6.70 (m, 2H), 6.64 (s, 1H), 4.41 (s, 2H), 4.03-3.92 (m, 1H), 3.79 (s, 3H), 3.59 (s, 3H), 2.83 (dd, J=14.6, 5.6 Hz, 1H), 2.51 (dd, J=14.5, 8.5 Hz, 1H), 1.37 (d, J=6.5 Hz, 3H); ESI-MS

Synthesis of (S)-methyl 3-((4-((4-methoxy-N-(2-methoxy-2-oxoethyl) phenyl) sulfonamido) naphthalen-1-yl) (benzyl) amino) butanoate (49)

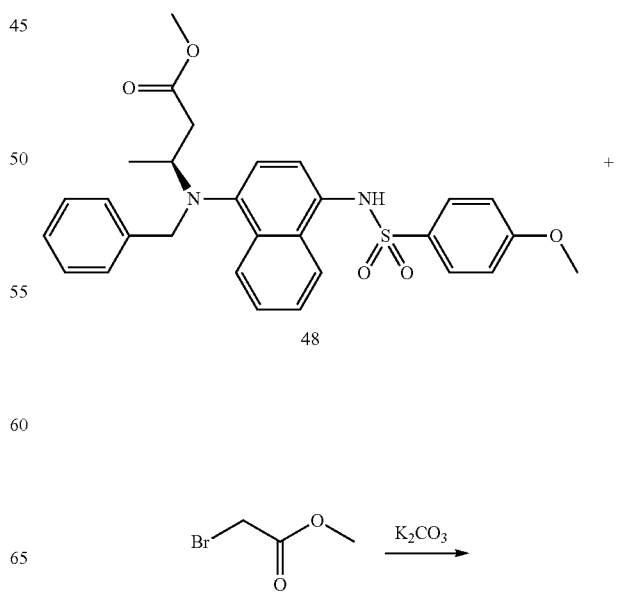

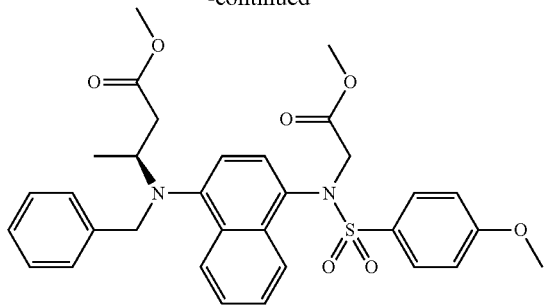

49

Compound 48 (0.10 g, 0.19 mol) is dissolved in 5.00 mL DMF, potassium carbonate (78.66 mg, 0.57 mmol) is added, and finally methyl bromoacetate (35.19 mg, 0.23 mmol) is added and stirred at room temperature. Reaction is carried out for 2 h, water is added to the solution until a solid precipitates out, extraction is performed with EA (30.00 mL) three times, the organic phases are combined, and washed with saturated NaCl aqueous solution (10.00 mL) three times, then the organic phase is dried with anhydrous $Na_2SO_4$ and is spin-dried so as to obtain a pale yellow oily liquid 49 of 90.65 mg with a yield of 81% ESI-MS m/z: 591.2 $[M+H]^+$.

Synthesis of (S)-3-(((4-((4methoxyphenyl) sulfonamido) naphthalen-1-yl) (benzyl) amino) butanoic acid (DDO-1160)

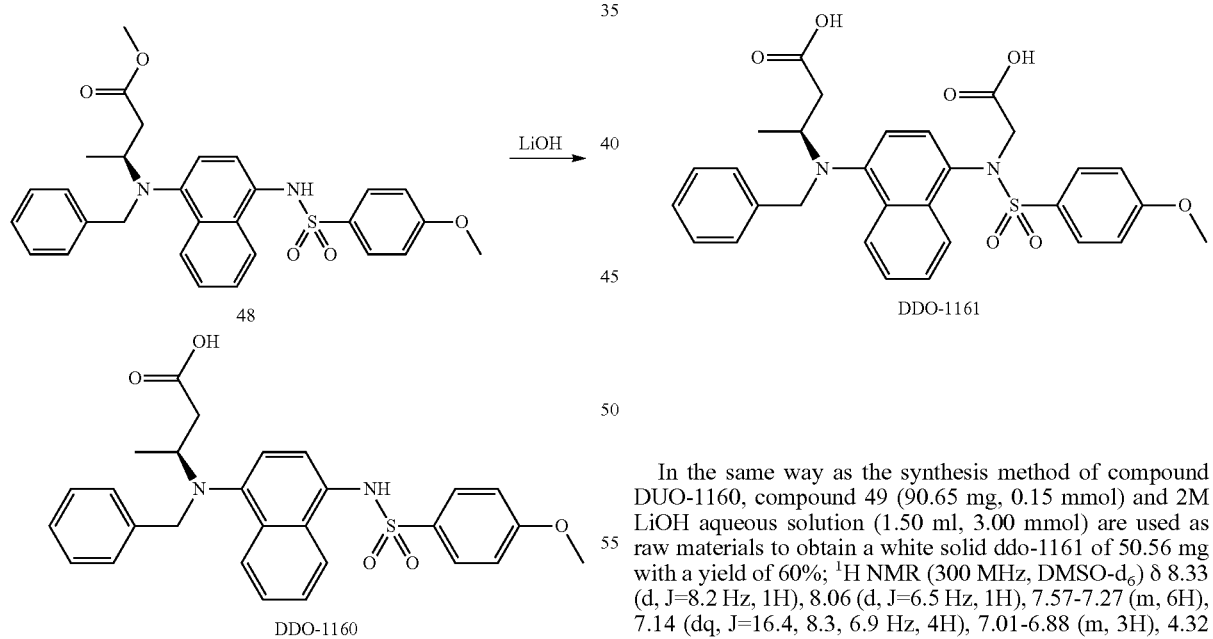

Compound 48 (0.10 g, 0.19 mmol) is dissolved in 5.00 mL of methanol, and 2 M aq. LiOH (0.95 mL, 1.90 mmol) is added and stirred overnight at room temperature. The next day, after TLC monitors the reaction to be complete, the solvent is evaporated under reduced pressure, insoluble material is filtered and the pH is adjusted to 4-5 with 1M dilute hydrochloric acid, a white precipitate is gradually precipitated, and is filtered so as to obtain a white solid DDO-1160 of 63.20 mg with a yield of 66%; $^1H$ NMR (300 MHz, DMSO-$d_6$) δ 12.19 (s, 1H), 9.73 (s, 1H), 8.30 (d, J=8.2 Hz, 1H), 7.96 (d, J=8.2 Hz, 1H), 7.55-7.35 (m, 4H), 7.31 (d, J=6.8 Hz, 2H), 7.19 (d, J=7.5 Hz, 1H), 7.14-7.00 (m, 3H), 6.98-6.90 (m, 2H), 6.84 (d, J=7.8 Hz, 1H), 4.35H), 3.83-3.72 (m, 3H), 3.67 (s, 1H), 2.70 (dd, 2H), 1.25 (s, 3H); $^{13}C$ NMR (75 MHz, DMSO-$d_6$) δ 173.52, 144.90, 139.99, 131.33, 129.22, 128.42, 128.18, 126.78, 126.07, 124.20, 123.43, 119.36, 114.48, 56.96, 56.02, 48.04, 17.03; HRMS (ESI): found 505.1789 ($C_{28}H_{28}N_2O_5S$, $[M+H]^+$, requires 505.1791); HPLC (85:15 methanol:water with 1‰ TFA): $t_R$=9.44 min, 96.3%.

Synthesis of (S)-3-(benzyl(4-((N-(carboxymethyl)-4methoxyphenyl) sulfonamido) naphthalen-1-yl) (benzyl) amino) butanoic acid (DDO-1161)

In the same way as the synthesis method of compound DUO-1160, compound 49 (90.65 mg, 0.15 mmol) and 2M LiOH aqueous solution (1.50 ml, 3.00 mmol) are used as raw materials to obtain a white solid ddo-1161 of 50.56 mg with a yield of 60%; $^1H$ NMR (300 MHz, DMSO-$d_6$) δ 8.33 (d, J=8.2 Hz, 1H), 8.06 (d, J=6.5 Hz, 1H), 7.57-7.27 (m, 6H), 7.14 (dq, J=16.4, 8.3, 6.9 Hz, 4H), 7.01-6.88 (m, 3H), 4.32 (dd, J=31.5, 13.5 Hz, 4H), 3.84 (d, J=3.3 Hz, 3H), 3.77 (s, 1H), 2.73 (s, 2H), 1.28 (s, 3H); $^{13}C$ NMR (75 MHz, DMSO-$d_6$) δ 173.49, 170.47, 163.09, 146.96, 140.00, 133.38, 131.30, 130.20, 128.42, 128.27, 127.33, 126.85, 126.37, 126.13, 125.07, 124.19, 118.84, 114.45, 57.06, 56.12, 53.50, 47.75, 38.78, 17.05; HRMS(ESI): found 563.1844. ($C_{30}H_{30}N_2O_7S$, $[M+H]^+$, requires 563.1846); HPLC (85:15 methanol:water with 1‰ TFA): $t_R$=9.38 min, 100.00%.

Synthesis of (S)-methyl 3-((4-((tert-butoxycarbonyl) amino) naphthalen-1-yl) (4-methylbenzyl) amino) butanoate (50)

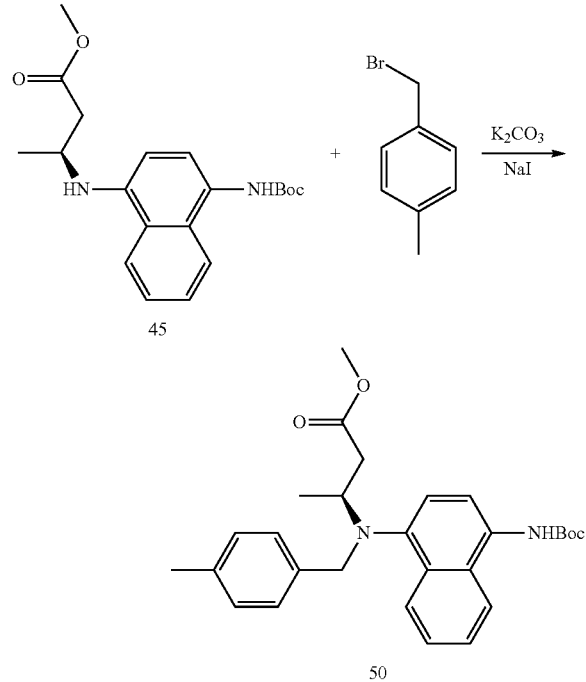

In the same way as the synthesis method of compound 46, the reaction is carried out on compound 45 (0.36 g, 1.00 mmol), 4-methylbenzylbromide (0.56 g, 3.00 mmol), K$_2$CO$_3$ (0.83 g, 6.00 mmol) and NaI (0.90 g, 6.00 mmol) as starting materials to obtain a pale yellow liquid 50 of 0.35 g with a yield of 76%; $^1$H NMR (300 MHz, Chloroform-d) δ 8.42 (d, J=8.5 Hz, 1H), 7.83 (d, J=7.7 Hz, 1H), 7.65 (d, J=8.0 Hz, 1H), 7.53 (dq, J=12.6, 6.8 Hz, 2H), 7.18 (d, J=9.4 Hz, 3H), 6.95 (d, J=7.7 Hz, 2H), 6.65 (s, 1H), 4.38 (s, 2H), 3.90 (dt, J=8.6, 6.1 Hz, 1H), 3.61 (s, 3H), 2.94-2.79 (m, 1H), 2.51 (dd, J=14.5, 8.9 Hz, 1H), 2.21 (s, 3H), 1.55 (s, 9H), 1.33 (d, J=6.3 Hz, 3H); ESI-MS m/z: 463.3 [M+H]$^+$.

Synthesis of (S)-methyl 3-((4-((4-methoxyphenyl) sulfonamido) naphthalen-1-yl) (4-methylbenzyl) amino) butanoate (51)

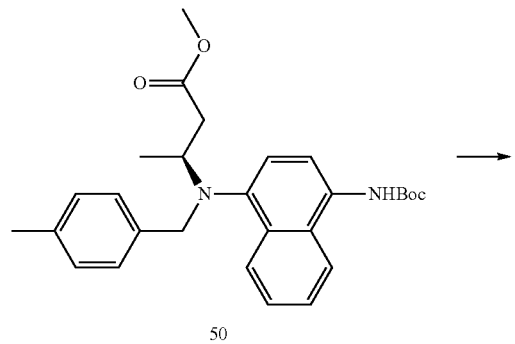

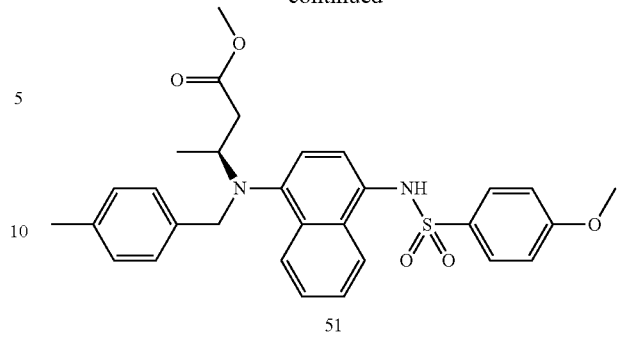

In the same way as the synthesis method of compound 48, after BOC removal, compound 50 (0.35 g, 0.76 mmol) reacts with 4-methoxybenzene sulfonyl chloride (0.19 g, 0.91 mmol) and pyridine (0.18 g, 2.28 mmol) to obtain a white solid 51 of 0.25 g with a yield of 62%; $^1$H NMR (300 MHz, Chloroform-d) δ 8.32 (d, J=8.4 Hz, 1H), 7.75 (d, J=8.4 Hz, 1H), 7.57-7.51 (m, 2H), 7.48 (d, J=7.9 Hz, 1H), 7.40 (d, J=8.0 Hz, 1H), 7.2-7.10 (m, 3H), 7.03 (d, J=8.1 Hz, 1H), 6.95 (d, J=7.7 Hz, 2H), 6.75 (d, J=9.0 Hz, 2H), 6.56 (s, 1H), 4.37 (s, 2H), 4.00-3.90 (m, 1H), 3.80 (s, 3H), 3.58 (s, 3H), 2.82 (dd, J=14.3, 5.8 Hz, 1H), 2.57-2.45 (m, 2.22 (s, 3H), 1.30 (d, J=8.3 Hz, 3H); ESI-MS m/z: 533.2 [M+H]$^+$.

Synthesis of (S)-methyl 3-(4-((4-methoxy-N-(2-methoxy-2-oxoethyl) phenyl) sulfonamido) naphthalen-1-yl) (4-methylbenzyl) amino) butanoate (52)

In the same way as the synthesis method of compound 49, compound 51 (0.10 g, 0.18 mmol), methyl bromoacetate (34.51 mg, 0.22 mmol) and K₇CO₃ (74.52 mg, 0.54 mmol) are used as starting materials to obtain a pale yellow solid 52 of 80.36 mg with a yield of 74%; ESI-MS m/z: 605.2 [M+H]⁺.

(5) Synthesis of 3-((4-((4-methoxyphenyl) sulfonamido) naphthalen-1-yl) (4-methylbenzyl) amino) butanoic acid (DDO-1162)

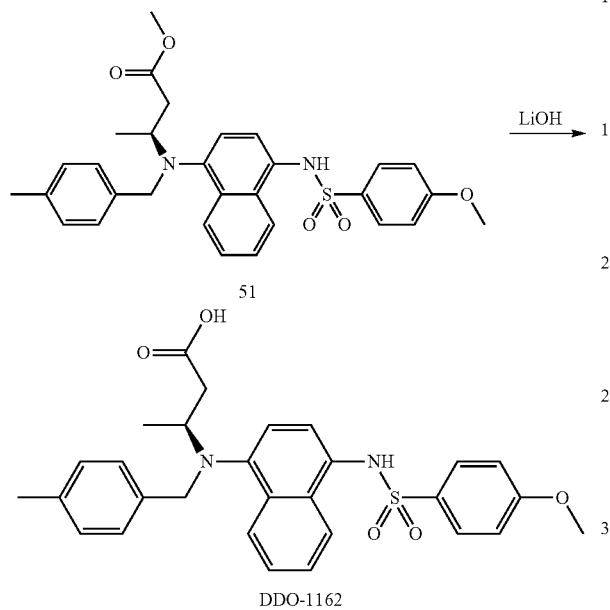

In the same way as the synthesis method of compound DDO-1160, reaction is performed on compound 51 (0.10 g, 0.18 mmol) and 2 M aqueous solution of LiOH (1.00 mL, 2.00 mmol) are used as starting material to obtain a white solid DDO-1162 of 65.00 mg with a yield of 70%; ¹H NMR (300 MHz, DMSO-d₆) δ 12.25 (s, 1H), 9.78 (s, 1H), 8.28 (d, J=8.4 Hz, 1H), 7.96 (d, J=8.4 Hz, 1H), 7.55-7.44 (m, 3H), 7.40 (t, J=7.6 Hz, 1H), 7.18 (dd. J=7.9, 4.5 Hz, 3H), 7.02-687 (m, 4H), 6.82 (d, J=8.0 Hz, 1H), 4.28 (d, J=5.8 Hz, 2H), 3.79 (s, 3H), 3.64 (s, 1H), 2.69 (s, 1H), 2.51 (d, J=1.9 Hz, 1H), 2.12 (s, 3H), 1.24 (s, 3H); HRMS(ESI): found 519.1953. (C₂₉H₃₀N₂O₅S, [M+H]⁺, requires 519.1875); HPLC (85:15 methanol:water with 1% TFA): t$_R$=13.47 min, 100.00%.

Synthesis of (S)-3-((4-(N-(carboxymethyl)-4-methoxyphenyl) sulfonamido) naphthalen-1-yl) (4-methylbenzyl) amino) butanoic acid (DDO-1163)

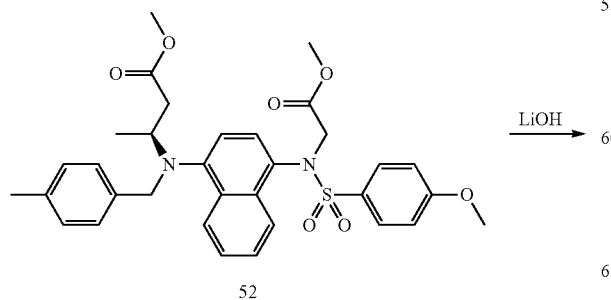

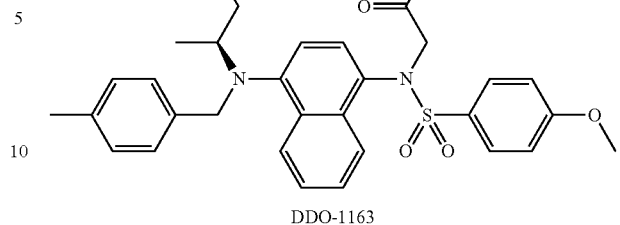

In the same way as the synthesis method of compound DDO-1161, reaction is performed on compound 52 (80.36 mg, 0.13 mmol) and 2M aqueous solution of LiOH (1.50 mL, 3.00 mmol) as starting material to obtain a white solid DDO-1163 of 50.30 mg with a yield of 67%; ¹H NMR (300 MHz, DMSO-d₆) δ 12.39 (s, 2H), 8.30 (d, J=8.3 Hz, 114), 8.10-8.00 (m, 1H), 7.61-7.34 (m, 4H), 7.20 (dd, J=13.3, 7.8 Hz, 3H), 6.95 (t, J=7.2 Hz, 5H), 4.44-4.19 (m, 4H), 3.89-3.78 (m, 3H), 3.73 (s, 1H), 2.73 (5, 1H), 2.58 (s, 1H), 2.14 (s, 3H), 1.25 (d, J=11.5 Hz, 3H); HRMS(ESI): found 577.2008. (C₃₁H₃₂N₂O₇S, [M+H]⁺, requires 577.1930); HPLC (85:15 methanol:water with 1‰ TFA): t$_R$=13.36 min, 96.50%.

Synthesis of (S)-methyl 3-((4-((tert-butoxycarbonyl) amino) naphthalen-1-yl) (4-chlorobenzyl) amino) butanoate (53)

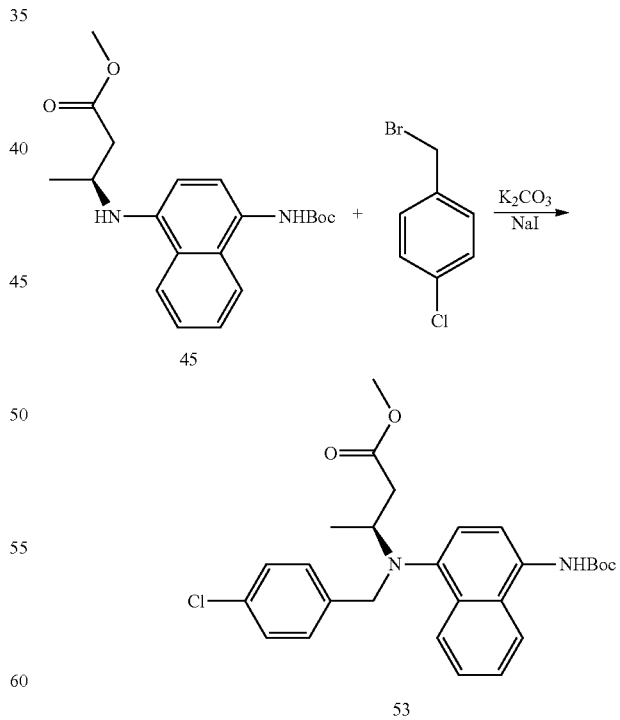

In the same way as the synthesis method of compound 46, reaction is performed on compound 45 (0.36 g, 1.00 mmol), 4-chlorobenzyl bromide (0.61 g, 3.00 mmol), K₂CO₃ (0.83 g, 6.00 mmol) and NaI (0.90 g, 6.00 mmol) as raw materials to obtain a pale yellow liquid 53 of 0.33 g with a yield of 68%; ESI-MS m/z: 483.2 [M+H]⁺.

Synthesis of (S)-methyl 3-((4-chlorobenzyl) (4-((4-methoxyphenyl) sulfonamido) naphthalen-1-yl) amino) butanoate (54)

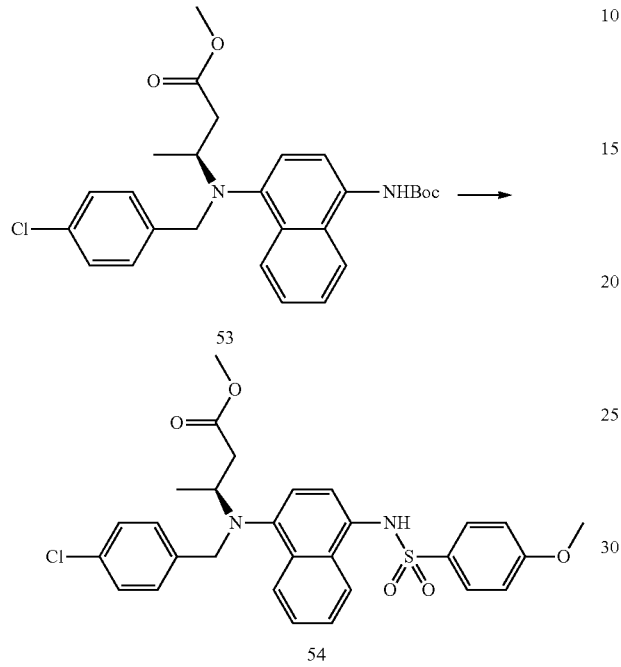

In the same way as the synthesis method of compound 48, after BOC removal, compound 53 (0.33 g, 0.68 mmol) reacts with 4-methoxybenzenesulfonyl chloride (0.17 g, 0.82 mmol) and pyridine (0.16 g, 2.04 mmol) to obtain a white solid 54 of 0.23 g with a yield of 61%; ¹H NMR (300 MHz, Chloroform-d) δ 8.28 (d, J=8.5 Hz, 1H), 7.79 (d, J=8.5 Hz, 1H), 7.57-7.44 (m, 3H), 7.38 (s, 1H), 7.30-7.05 (m, 6H), 6.85 (s, 1H), 6.78-6.68 (m, 2H), 4.35 (d, J=4.2 Hz, 2H), 3.93 (p, J=6.7 Hz, 1H), 3.78 (d, J=3.6 Hz, 3H), 3.59 (s, 3H), 2.79 (s, 1H), 2.51 (s, 1H), 1.32 (dd, J=13.4, 7.1 Hz, 3H); ESI-MS m/z: 553.1 [M+H]⁺.

Synthesis of (S)-methyl 3-((4-chlorobenzyl) (4-((4-methoxy-N-(2-methoxy-2-oxoethyl) phenyl) sulfonamido) naphthalen-1-yl) amino) butanoate (55)

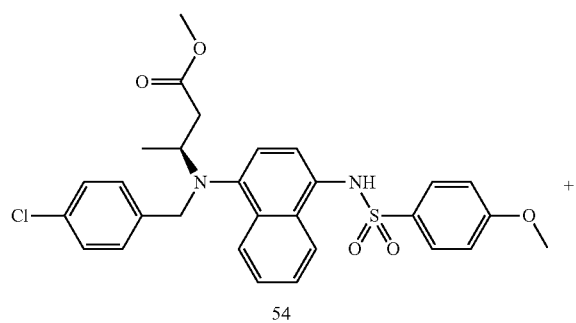

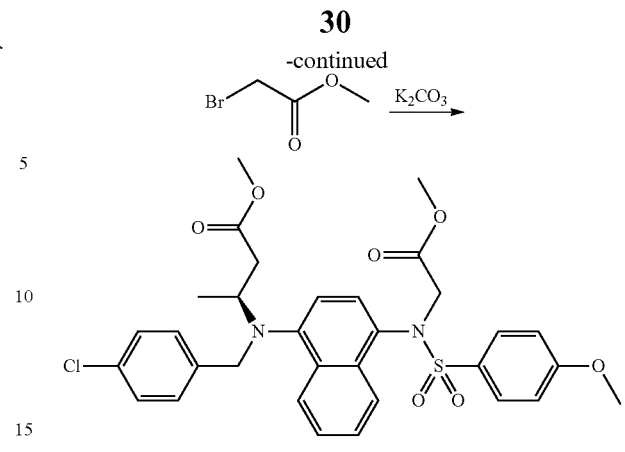

In the same way as the synthesis method of compound 49, reaction is performed on compound 54 (0.10 g, 0.18 mmol), methyl bromoacetate (34.51 mg, 0.22 mmol) and K₂CO₃ (74.52 mg, 0.54 mmol) as starting materials to obtain a pale yellow solid 55 of 74.16 mg with yield of 65%; ESI-MS m/z: 625.2 [M+H]⁺.

Synthesis of (S)-3-((4-chlorobenzyl) (4-((4-methoxyphenyl) sulfonamido) naphthalen-1-yl) amino) butanoic acid (DDO-1164)

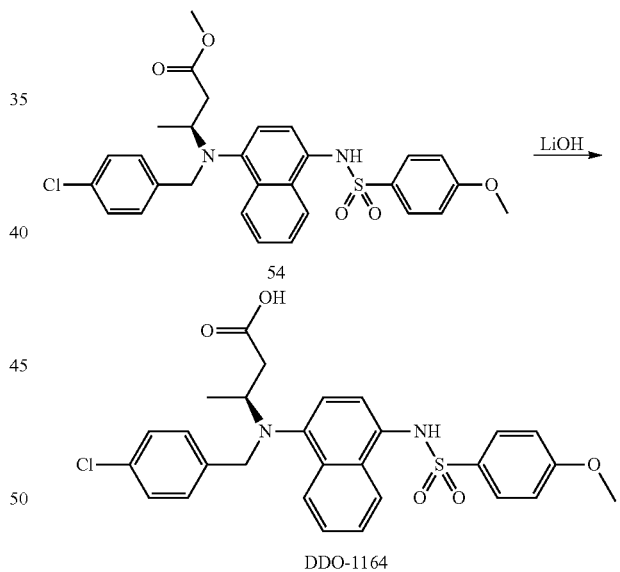

In the same way as the synthesis method of compound DDO-1160, reaction is performed on compound 54 (0.10 g, 0.18 mmol) and 2M aqueous LiOH (1.00 mL, 2.00 mmol) as starting materials to obtain a white solid DDO-1164 of 63 mg with yield of 65%; ¹H NMR (300 MHz, DMSO-d₆) δ 9.77 (s, 1H), 8.30 (d, J=8.5 Hz, 1H), 7.99 (d, J=8.5 Hz, 1H), 7.57-7.46 (m, 3H), 7.42 (t, J=7.7 Hz, 1H), 7.34 (d, J=8.1 Hz, 2H), 7.26-7.13 (m, 3H), 7.00-6.91 (m, 2H), 6.87 (d, J=8.0 Hz, 1H), 4.43-4.27 (m, 2H), 3.81 (d, J=2.0 Hz, 3H), 3.68 (s, 1H), 2.72 (s, 2H), 1.26 (s, 3H); HRMS(ESI): found 539.1408 (C28H27ClN2O5S, [M+H]+, requires 539.1329); HPLC (85:15 methanol:water with 1‰ TFA): t_R=13.92 min, 97.55%.

Synthesis of (S)-3-((4-((N-(carboxymethyl)-4-methoxyphenyl) sulfonamido) naphthalen-1-yl)(4-chlorobenzyl) amino) butanoic acid (DDO-1165)

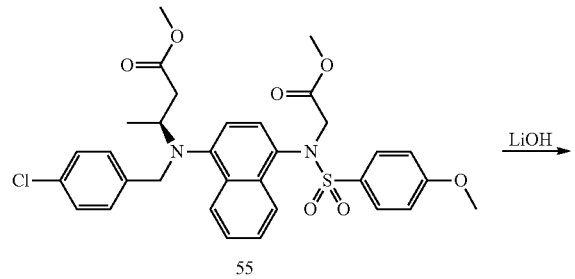

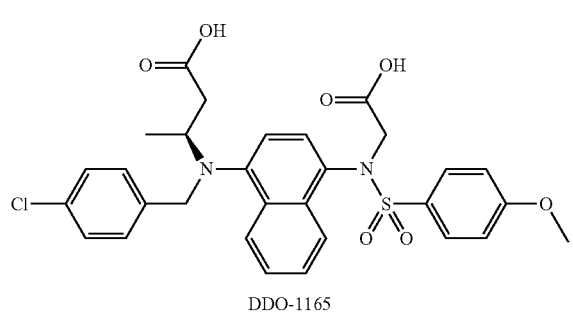

DDO-1165

In the same way as the synthesis method of compound DDO-1161, reaction is performed on compound 55 (74.16 mg, 0.12 mmol) and 2M aqueous LiOH (1.50 mL, 3.00 mmol) as starting materials to obtain a white solid DDO-1165 of 52.30 mg with yield of 73%; $^1$H NMR (300 MHz, DMSO-d$_6$) δ 12.47 (s, 2H), 8.32 (s, 1H), 8.10 (s, 1H), 7.40 (d, J=8.8 Hz, 5H), 7.22 (s, 3H), 6.98 (s, 3H), 4.36 (d, J=19.5 Hz, 4H), 3.86 (t, J=5.5 Hz, 3H), 3.84 (s, 1H), 2.76 (s, 2H), 1.28 (s, 3H); HRMS(ESI): found 597.1459. (C$_{30}$H$_{29}$ClN$_2$O$_7$S, [M+H]$^+$, requires 597.1384); HPLC (85:15 methanol:water with 1‰ TFA): t$_R$=13.50 min, 95.71%.

Synthesis of (S)-methyl 3-((4-((tert-butoxycarbonyl) amino) naphthalen-1-yl) (4-fluorobenzyl) amino) butanoate (56)

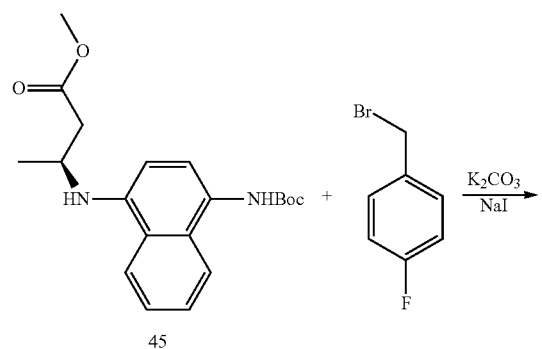

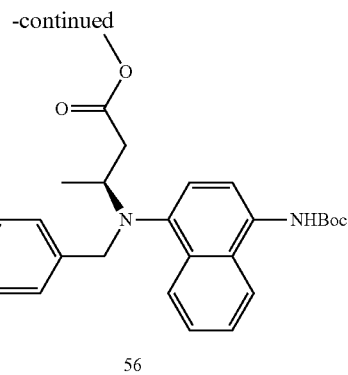

56

In the same way as the synthesis method of compound 46, reaction is performed on compound 45 (0.36 g, 1.00 mmol), 4-fluorobenzyl bromide (0.57 g, 3.00 mmol) and K$_2$CO$_3$ (0.83 g 6.00 mmol) as starting materials to obtain a pale yellow liquid 56 of 0.36 g with a yield of 77%; $^1$H NMR (300 MHz, Chloroform-d) δ 8.31-8.22 (m, 1H), 7.72 (dq, J=7.1, 2.7 Hz, 1H), 7.56 (d. J=8.1 Hz, 1H), 7.42 (ddt, J=7.3, 4.7, 2.2 Hz, 2H), 7.17 (tq, J=5.6, 2.5 Hz, 2H), 7.06 (dt, J=8.1, 2.5 Hz, 1H), 6.70 (tt, J=8.7, 2.5 Hz, 2H), 6.56 (s, 1H), 4.26 (s, 2H), 3.84-3.71 (m, 1H), 3.51 (s, 3H), 2.79-2.67 (m, 1H), 2.47-2.34 (m, 1H), 1.48-1.38 (s, 9H), 1.19 (dq, J=8.7, 3.1, 2.3 Hz, 3H); ESI-MS m/z: 467.2 [M+H]$^+$.

Synthesis of (S)-methyl 3-((4-fluorobenzyl) (4-((4-methoxyphenyl) sulfonamido) naphthalen-1-yl) amino) butanoate (57)

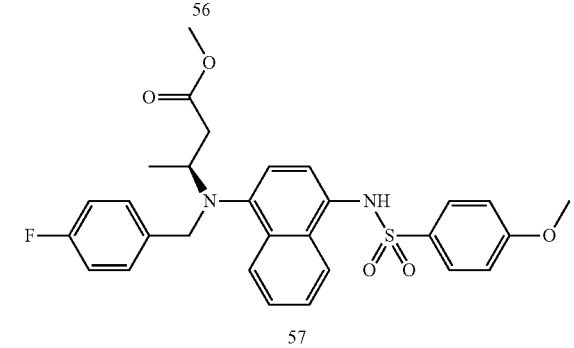

In the same way as the synthesis method of compound 48, after BOC, removal, compound 56 (0.36 g, 0.77 mmol) reacts with 4-methoxybenzenesulfonyl chloride (0.19 g, 0.92 mmol) and pyridine (0.18 g, 2.31 mmol) to obtain a white solid 57 of 0.26 g with a yield of 63% $^1$H NMR (300

MHz, Chloroform-d) δ 8.28 (d, J=8.4 Hz, 1H), 7.75 (d, J=8.3 Hz, 1H), 7.59-7.43 (m, 3H), 7.38 (s, 1H), 7.25-7.13 (m, 3H), 7.02 (dd, J=8.1, 2.8 Hz, 1H), 6.86-6.65 (m, 5H), 4.36 (s, 2H), 3.99-3.87 (m, 1H), 3.79 (d, J=2.9 Hz, 3H), 3.59 (d, J=2.7 Hz, 3H), 2.81 (dd, J=14.8, 5.5 Hz, 1H), 2.49 (dd, J=14.4, 8.2 Hz, 1H), 1.30-1.25 (m, 3H); ESI-MS m/z: 537.2 [M+H]⁺.

Synthesis of (5)-methyl 3-((4-fluorobenzyl) (4-((4-methoxy-N-(2-methoxy-2-oxoethyl) phenyl) sulfonamido) naphthalen-1-yl) amino) butanoate (58)

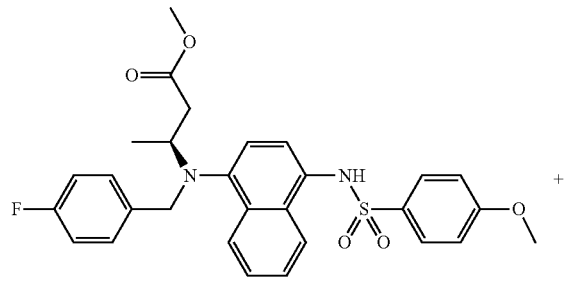

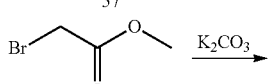

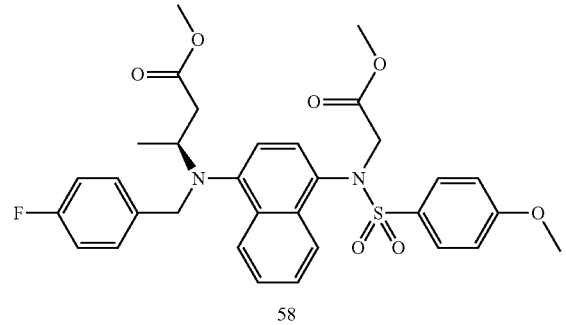

In the same way as the synthesis method of compound 49, reaction is performed on compound 57 (0.10 g, 0.18 mmol), methyl bromoacetate (34.51 mg, 0.22 mmol) and K₂CO₃ (74.52 mg, 0.54 mmol) as starting materials to obtain a pale yellow solid 58 of 75.36 mg with yield of 68%. ESI-MS m/z: 609.2 [M+H]⁺.

Synthesis of (S)-3-((4-fluorobenzyl) (4-((4-methoxyphenyl) sulfonamido) naphthalen-1-yl) amino) butanoic acid (DDO-1166)

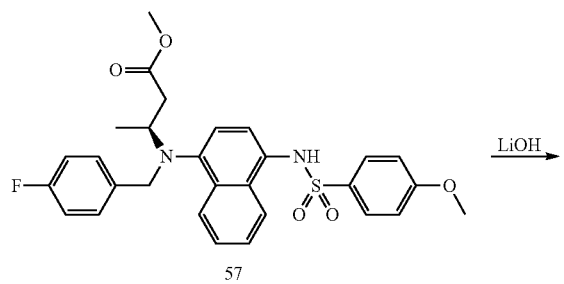

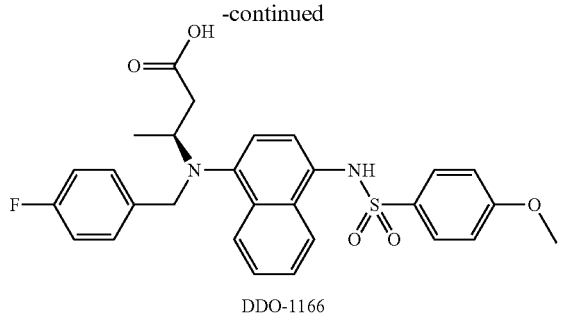

In the same way as the synthesis method of compound DDO-1160, reaction is performed on compound 57 (0.10 g, 0.18 mmol) and 2M aqueous LiOH (1.00 mL, 2.00 mmol) as starting materials to obtain a white solid DDO-1166 of 60.00 mg with yield of 65%; ¹H NMR (300 MHz, DMSO-d₆) δ 12.20 (s, 1H), 9.78 (d, J=6.9 Hz, 1H), 8.30 (s, 1H), 7.97 (d, J=10.9 Hz, 1H), 7.51 (s, 4H), 7.36 (s, 2H), 7.22 (d, J=7.0 Hz, 1H), 7.05-6.74 (m, 5H), 4.35 (s, 2H), 3.79 (d, J=4.4 Hz, 3H), 3.68 (s, 1H), 2.74 (dd, 2H), 1.26 (s, 3H); HRMS(ESI): found 523.1703 (C₂₈H₂₇FN₂O₅S, [M+H]⁺, requires 523.1625); HPLC, (85:15 methanol:water with 1‰ TFA): t$_R$=11.89 min, 95.74%.

Synthesis of (S)-3-((4-((N-(carboxymethyl)-4-methoxyphenyl) sulfonamido) naphthalen-1-yl) (4-fluorobenzyl) amino) butanoic acid (DDO-1167)

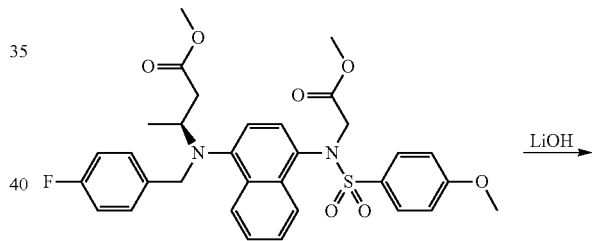

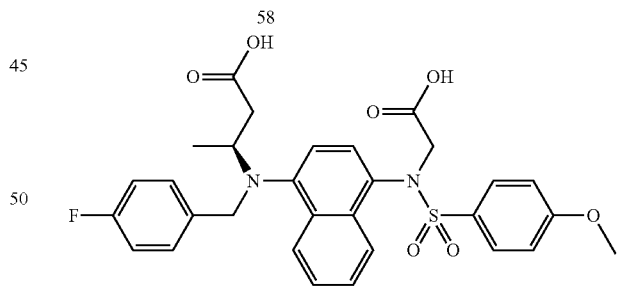

In the same way as the synthesis method of compound DDO-1161, reaction is performed on compound 58 (75.36 mg, 0.12 mmol) and 2M aqueous LiOH (1.50 mL, 3.00 mmol) as starting materials to obtain a white solid DDO-1167 of 53.30 mg with yield of 75%; ¹H NMR (300 MHz, DMSO-d₆) δ 12.47 (s, 2H), 8.33 (s, 1H), 8.09 (s, 1H), 7.44 (d, J=21.9 Hz, 6H), 7.22 (s, 1H), 6.99 (s, 5H), 4.38 (s, 4H), 3.90-3.80 (m, 3H), 3.78 (s, 1H), 2.68 (d, J=48.8 Hz, 2H), 1.28 (s, 3H); HRMS(ESI): found 581.1755. (C₃₀H₂₉FN₂O₇S, [M+H]⁺, requires 581.1680); HPLC (85:15 methanol:water with 1‰ TFA): t$_R$=11.37 min, 95.89%.

Synthesis of (S)-methyl 3-((4-((tert-butoxycarbonyl) amino) naphthalen-1-yl) (3-methylbenzyl) amino) butanoate (59)

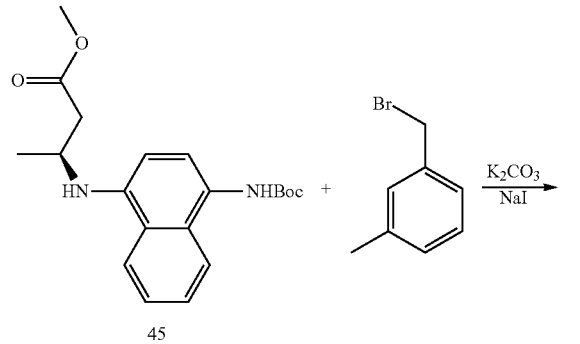

45

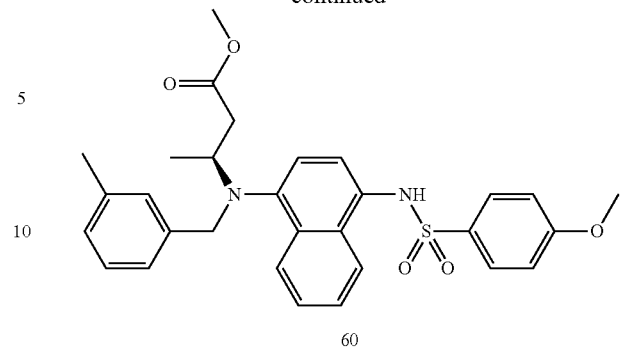

60

In the same way as the synthesis method of compound 48, after BOC removal, compound 59 (0.33 g, 0.69 mmol) reacts with 4-methoxybenzenesulfonyl chloride (0.17 g 0.83 mmol) and pyridine (0.16 g, 2.07 mmol) to obtain a white solid 60 of 0.25 g with a yield of 68%; $^1$H NMR (300 MHz, Chloroform-d) δ 8.32 (d, J=8.5 Hz, 1H), 7.74 (d, J=8.4 Hz, 1H), 7.51 (t, J=10.1 Hz, 3H), 7.39 (d, J=14.9 Hz, 1H), 7.14-6.98 (m, 5H), 6.90 (d, J=7.4 Hz, 1H), 6.75 (d, J=8.7 Hz, 2H), 6.53 (s, 1H), 4.36 (s, 2H), 3.95 (q, J=6.8 Hz, 1H), 3.80 (s, 3H), 3.58 (s, 3H), 2.82 (dd, J=14.5, 5.71 Hz, 1H), 2.49 (dd, J=14.5, 8.5 Hz, 1H), 2.22 (s, 3H), 1.29 (d, J=8.5 Hz, 3H); ESI-MS m/z: 533.2 [M+H]$^+$.

Synthesis of (S)-methyl 3-((4-((4-methoxy-N-(2-methoxy-2-oxoethyl) phenyl) sulfonamido) naphthalen-1-yl) (3-methylbenzyl) amino) butanoate (61)

59

In the same way as the synthesis method of compound 46, reaction is performed on compound 45 (0.36 g, 1.00 mmol), 3-methylbenzyl bromide (0.56 g, 3.00 mmol) and K$_2$CO$_3$ (0.83 g, 6.00 mmol) as starting materials to obtain a pale yellow liquid 59 of 0.32 g with a yield of 69%; $^1$H NMR (300 MHz Chloroform-d) δ 8.47-8.39 (m, 1H), 7.83 (dd, J=7.7, 1.9 Hz, 1H), 7.65 (d, J=7.9 Hz, 1H), 7.59-7.48 (m, 2H), 7.14 (t, J=8.5 Hz, 3H), 7.02 (t, J=7.6 Hz, 1H), 6.88 (d, J=7.5 Hz, 1H), 6.64 (s, 1H), 4.37 (d, J=3.2 Hz, 2H), 3.90 (dt, J=8.9, 6.1 Hz, 1H), 3.61 (s, 3H), 2.88-2.80 (m, 1H), 2.50 (dd, J=14.5, 8.9 Hz, 1H), 2.22 (s, 3H), 1.57 (s, 9H), 1.34 (d, J=7.8 Hz, 3H); ESI-MS m/z: 463.3 [M+H]$^+$.

Synthesis of (S)-methyl 3-((4-((4-methoxyphenyl) sulfonamido) naphthalen-1-yl) (3-methylbenzyl) amino) butanoate (60)

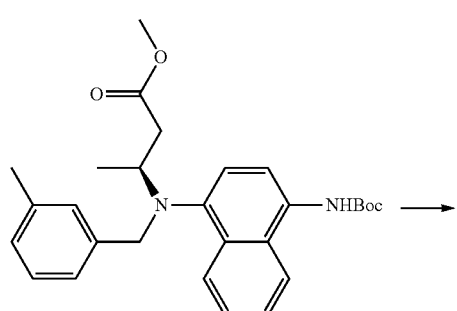

59

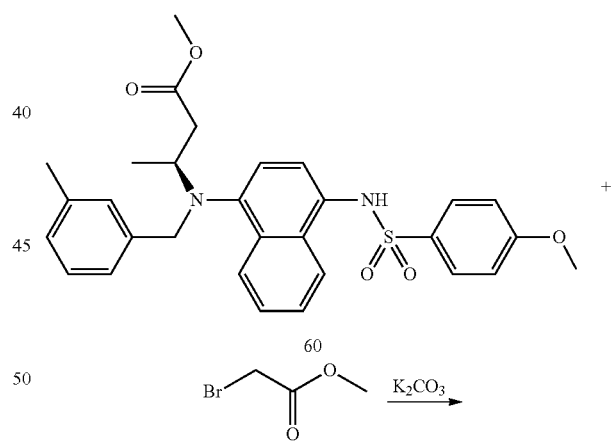

60

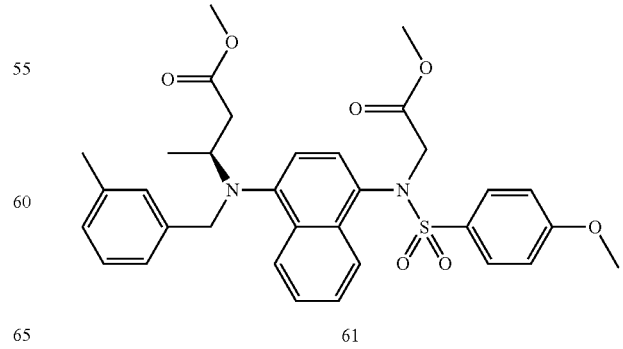

61

In the same way as the synthesis method of compound 49, reaction is performed on compound 60 (0.10 g, 0.19 mmol), methyl bromoacetate (34.51 mg, 0.26 mmol) and K₂CO₃ (77.81 mg, 0.56 mmol) as starting materials to obtain a pale yellow solid 61 of 65.16 mg with yield of 57%; ESI-MS m/z: 605.2 [M+H]⁺.

Synthesis of (S)-3-((4-((4-methoxyphenyl) sulfonamido) naphthalen-1-yl) (3-methylbenzyl) amino) butanoic acid (DDO-1168)

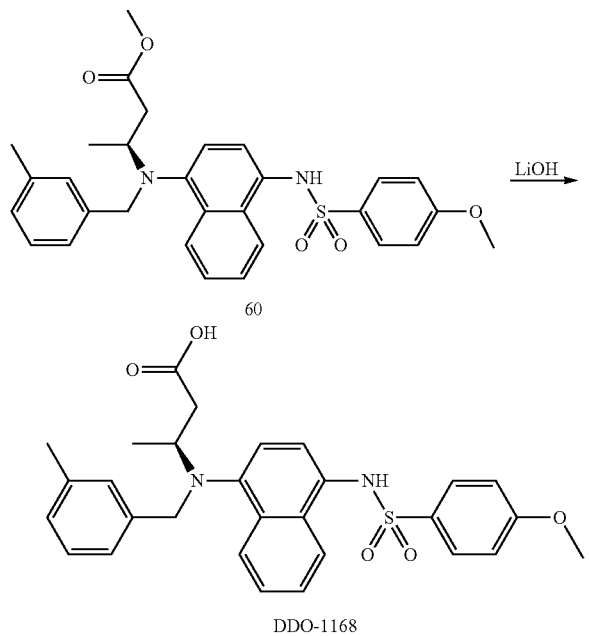

In the same way as the synthesis method of compound DDO-1160, reaction is performed on compound 60 (0.10 g, 0.19 mmol) and 2M aqueous LiOH (1.00 mL, 2.00 mmol) as starting materials to obtain a white solid DDO-1168 of 60.40 mg with yield of 61%; ¹H NMR (300 MHz, DMSO-d₆) δ 12.25 (s, 1H), 9.79 (d, J=6.8 Hz, 1H), 8.29 (d, J=8.3 Hz, 1H), 8.05-7.88 (m, 1H), 7.51 (s, 4H), 7.13 (s, 3H), 6.99-6.77 (m, 5H), 4.40-4.22 (m, 2H), 3.80 (s, 3H), 3.66 (s, 1H), 2.71 (s, 2H), 2.12 (t, J=7.3 Hz, 3H), 1.26 (s, 3H); HRMS(ESI): found 519.1952 (C₂₉H₃₀N₂O₅S, [M+H]⁺, requires 519.1875); HPLC (85:15 methanol:water with 1‰ TFA): t_R=13.49 min, 96.45%.

Synthesis of (S)-3-((4-((N-(carboxy)-4-methoxyphenyl) sulfonamide) naphthalen-1-yl) (3-methylbenzyl) amino) butanoic acid (DDO-1169)

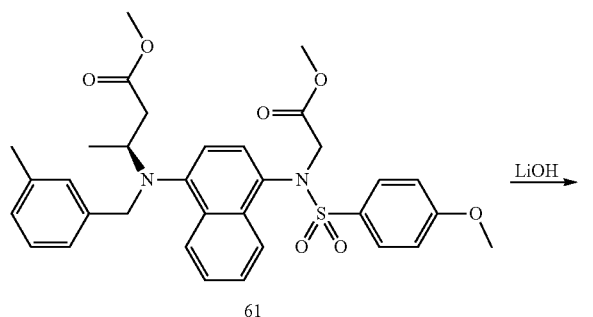

In the same way as the synthesis method of compound DDO-1161, reaction is performed on compound 61 (65.16 mg, 0.11 mmol) and 2M aqueous LiOH (1.00 mL, 2.00 mmol) as starting materials to obtain a white solid DDO-1169 of 45.30 mg with yield of 71%; ¹H NMR (300 MHz, DMSO-d₆) δ 12.48 (s, 2H), 8.32 (s, 1H), 8.07 (s, 1H), 7.52-7.39 (m, 4H), 7.18 (s, 3H), 7.04-6.92 (m, 5H), 4.32 (d, J=18.0 Hz, 4H), 3.84 (d, J=4.1 Hz, 3H), 3.36 (s, 1H), 2.73 (d, 2H), 2.17 (d, J=4.7 Hz, 3H), 1.27 (s, 3H); HRMS(ESI): found 577.2011. (C₃₁H₃₂N₂O₇S, [M+H]⁺, requires 577.1930); HPLC (85:15 methanol:water with 1‰ TFA): t_R=13.32 min, 96.00%.

Synthesis of (S)-methyl 3-((4-butoxycarbonyl) amino) naphthalen-1-yl) 2-methylbenzyl) amino) butanoate (62)

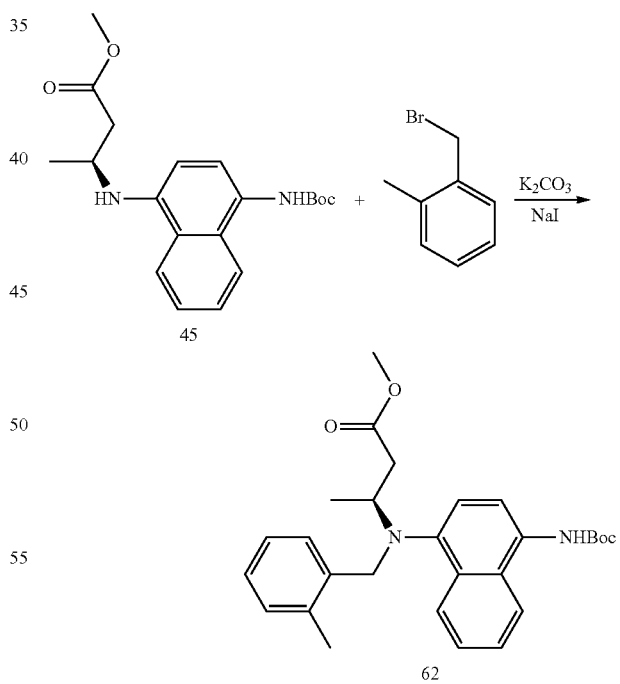

In the same way as the synthesis method of compound 46, reaction is performed on compound 45 (0.36 g, 1.00 mmol), 2-methylbenzyl bromide (0.56 g, 3.00 mmol), K₂CO₃ (0.83 g, 6.00 mmol) and dial (0.90 g, 6.00 mmol) as starting materials to obtain a pale yellow liquid 62 of 0.34 g with a yield of 74%; ¹H NMR (300 MHz, Chloroform-d) δ 8.44-

8.37 (m, 1H), 7.87-7.80 (m, 1H), 7.67 (d, 8.1 Hz, 1H), 7.56-7.49 (m, 2H), 7.38 (q, J=3.0 Hz, 1H), 7.27 (d, J=2.4 Hz, 2H), 7.02 (d, J=2.4 Hz, 1H), 6.92 (t, J=7.4 Hz, 1H), 6.66 (s, 1H), 4.38 (s, 2H), 3.94 (dt, J=9.0, 6.2 Hz, 1H), 3.59 (s, 3H), 2.86 (dd, J=14.4, 5.0 Hz, 1H), 2.58-2.48 (m, 1H), 2.44 (s, 3H), 1.55 (s, 9H), 1.38-1.34 (m, 3H); ESI-MS m/z: 463.3 [M+H]$^+$.

Synthesis of (S)-methyl 3-((4-((4-methoxyphenyl) sulfonamido) naphthalen-1-yl) (2-methylbenzyl) amino) butanoate (63)

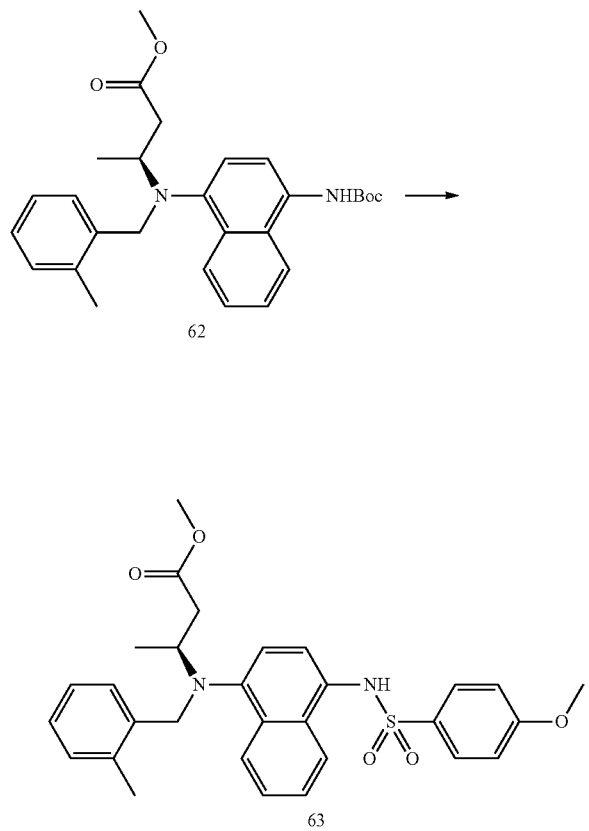

In the same way as the synthesis method of compound 48, after BOC removal, compound 62 (0.34 g, 0.74 mmol) reacts with 4-methoxybenzenesulfonyl chloride (0.18 g, 0.88 mmol) and pyridine (0.18 g, 2.22 mmol) to obtain a white solid 63 of 0.26 g with a yield of 65%; $^1$H NMR (300 MHz, Chloroform-d) δ 8.33 (d, J=8.4 Hz, 1H), 7.82 (d, J=8.4 Hz, 1H), 7.55 (d, J=8.7 Hz, 2H), 7.50-7.43 (m, 1H), 7.39 (d, J=7.3 Hz, 1H), 7.24 (s, 1H), 7.17 (d, J=8.1 Hz, 1H), 7.09-6.97 (m, 4H), 6.92 (td, J=7.2, 1.9 Hz, 1H), 6.74 (d, J=8.6 Hz, 2H), 4.38 (s, 2H), 4.05-3.95 (m, 1H), 3.77 (s, 3H), 3.57 (s, 3H), 2.85 (dd, J=14.6, 5.5 Hz, 1H), 2.52 (dd, J=14.6, 8.7 Hz, 1H), 2.43 (s, 3H), 1.37 (d, J=6.5 Hz, 3H); ESI-MS m/z: 533.2 [M+H]$^+$.

Synthesis of (S)-methyl 3-((4-((4-methoxy-N-(2-methoxy-2-oxoethyl) phenyl) sulfonamido) naphthalen-1-yl) (2-methylbenzyl) amino) butanoate (64)

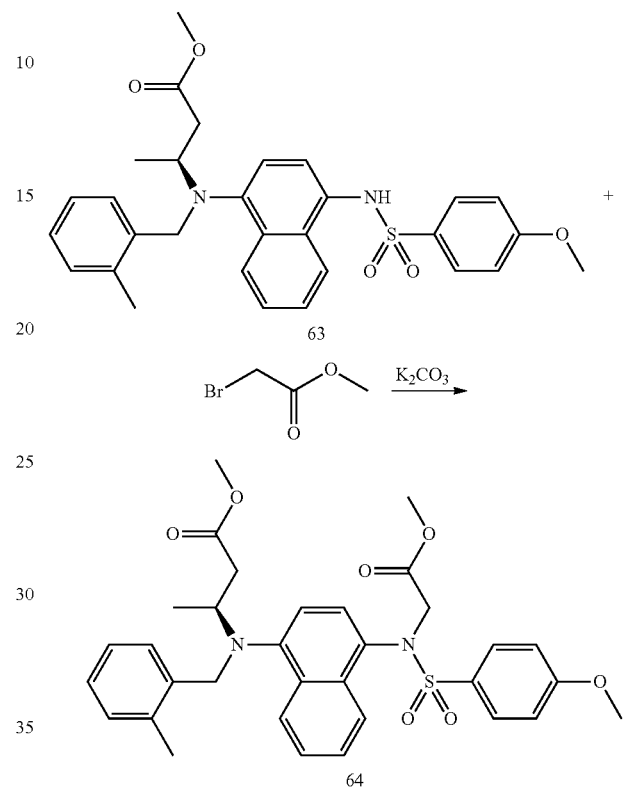

In the same way as the synthesis method of compound 49, reaction is performed on compound 63 (0.10 g, 0.19 mmol), methyl bromoacetate (34.51 mg, 0.26 mmol) and K$_2$CO$_3$ (77.81 mg, 0.56 mmol) as starting materials to obtain a pale yellow solid 64 of 64.16 mg, with yield of 57%. ESI-MS m/z: 605.2 [M+H]$^+$.

Synthesis of (S)-3-((4-((4-methoxyphenyl) sulfonamido) naphthalen-1-yl) (2-methylbenzyl) amino) butanoic acid (DDO-1170)

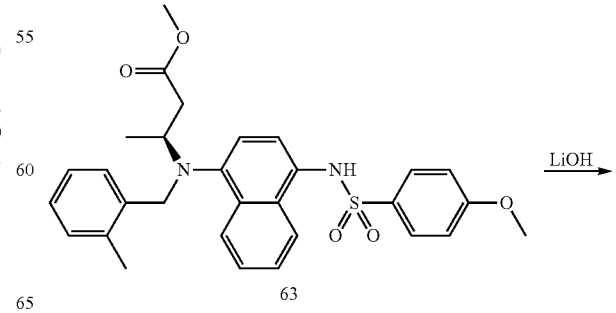

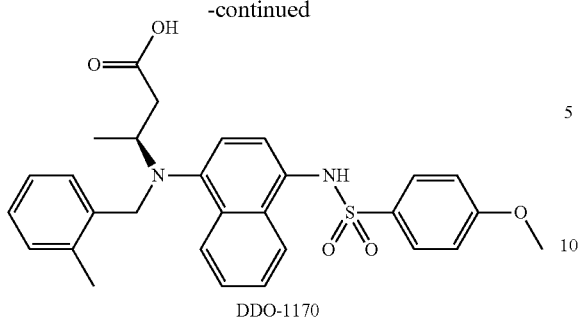

DDO-1170

In the same way as the synthesis method of compound DDO-1160, reaction is performed on compound 63 (0.10 g, 0.19 mmol) and 2M aqueous TAM (1.00 mL, 2.00 mmol) as starting materials to obtain a white solid DDO-1170 of 61.40 mg with yield of 62%; $^1$H NMR (300 MHz, DMSO-$d_6$) δ 12.24 (s, 1H), 8.28 (d, J=8.7 Hz, 1H), 7.97 (d, J=8.6 Hz, 1H), 7.70-7.33 (m, 4H), 7.22 (t, J=8.3 Hz, 2H), 7.16-6.73 (m, 1H), 4.34 (s, 2H), 3.83 (s, 3H), 3.68 (s, 1H), 2.70 (s, 2H), 2.53-2.36 (m, 3H), 1.33 (d, J=16.7 Hz, 3H); HRMS(ESI): found 519.1948 ($C_{29}H_{30}N_2O_5S$, [M+H]$^+$, requires 519.1875); HPLC (85:15 methanol:water with 1% TEN): $t_R$=13.30 min, 96.65%.

Synthesis of (S)-3-((4-((N-(carboxy)-4-methoxyphenyl) sulfonamido) naphthalen-1-yl) (2-methylbenzyl) amino) butanoic acid (DDO-1171)

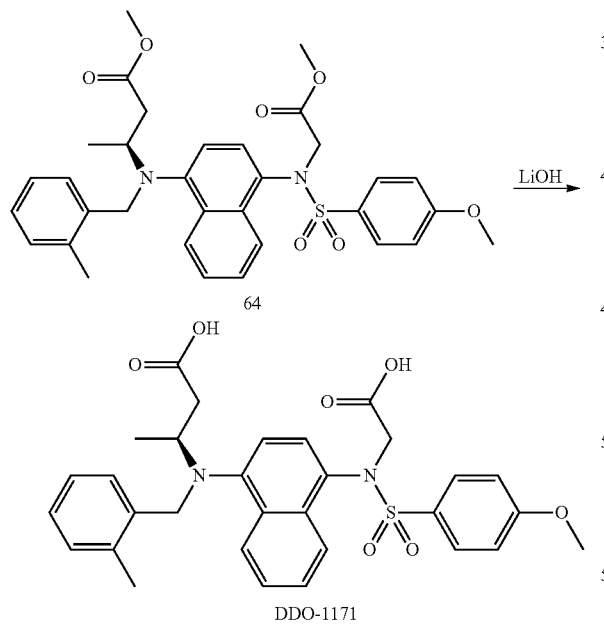

DDO-1171

In the same way as the synthesis method of compound DDO-1161, reaction is performed on compound 64 (64.16 mg, 0.11 ol) and 2M aqueous LiOH (1.00 mL, 2.00 mmol) as starting materials to obtain a white solid DDO-1171 of 43.30 mg with yield of 68%; $^1$H NMR (300 MHz, DMSO-$d_6$) δ 12.48 (s, 2H), 8.30 (d, J=8.4 Hz, 1H), 8.10 (t, J=7.6 Hz, 1H), 7.58-7.39 (m, 4H), 7.23 (dd, J=18.2, 7.7 Hz, 2H), 7.06-6.87 (m, 6H), 4.43-4.25 (m, 4H), 3.83 (t J=2.1 Hz, 3H), 3.77 (s, 1H), 2.74 (d, J=14.8 Hz, 1H), 2.59 (s, 1H), (s, 3H), 1.37-1.26 (m, 3H); HRMS(ESI): found 577.2009. ($C_{31}H_{32}N_2O_7S$, [M+H]$^+$, requires 577.1930); HPLC (85:15 methanol:water with 1‰ TFA): $t_R$=12.91 min 96.44%.

Synthesis of (S)-methyl 3-((4-((tert-butoxycarbonyl) amino) naphthalen-1-yl) (3-chlorobenzyl) amino) butanoate (65)

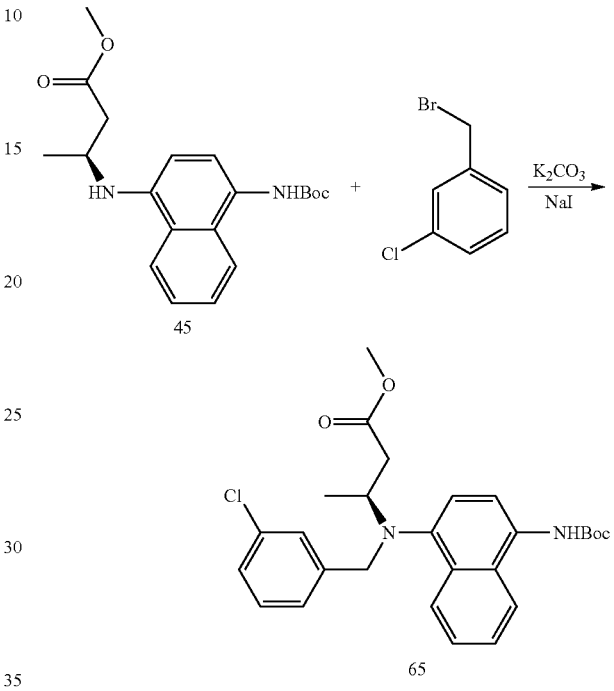

In the same as the synthesis method of compound 46, reaction is performed on compound 45 (0.36 g, 1.00 mmol), 3-chlorobromide (0.61 g, 3.00 mmol), K$_2$CO$_3$ (0.83 g, 5.00 mol) and NaI (0.90 g, 6.00 mmol) as starting materials to obtain a pale yellow liquid 65 of 0.35 g with a yield of 72%; $^1$H NMR (300 MHz, Chloroform-d) δ 8.29 (d, J=8.2 Hz, 1H), 7.78-7.70 (m, 1H), 7.50-7.36 (m, 2H), 7.21 (d, J=15.5 Hz, 2H), 7.13-7.05 (m, 2H), 6.98-6.91 (m, 2H), 6.58 (s, 1H), 4.28 (s, 2H), 3.85-3.76 (m, 1H), 3.52 (s, 3H), 2.71 (s, 1H), 2.41 (dd, J=14.5, 8.8 Hz, 1H) 1.44 (d, J=3.3 Hz, 9H), 1.26-1.20 (m, 3H); ESI-MS m/z: 483.2 [M+H]$^+$.

Synthesis of (S)-methyl 3-((3-chlorobenzyl) (4-((4-methoxyphenyl) sulfonamido) naphthalen-1-yl amino) butanoate (66)

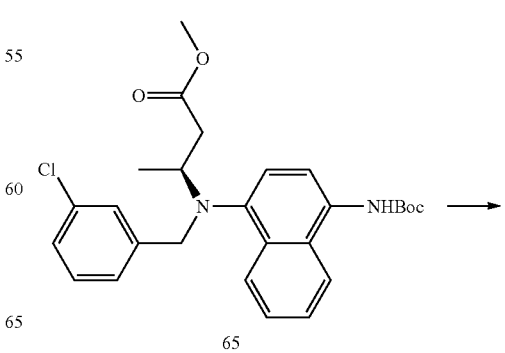

65

-continued

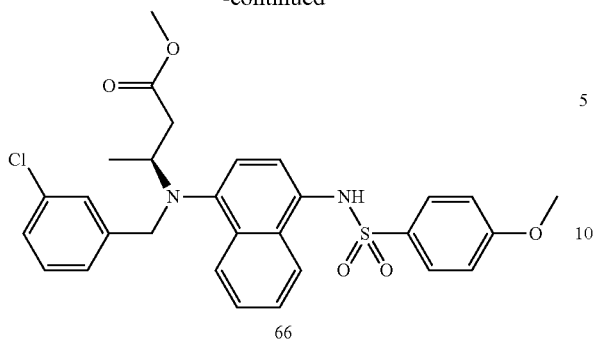

66

In the same way as the synthesis method of compound 48, after BOC removal, compound 65 (0.35 g, 0.72 mmol) reacts with 4-methoxybenzenesulfonyl chloride (0.18 g, 0.86 mmol) and pyridine (0.17 g, 2.16 mmol) to obtain a white solid 66 of 0.26 g with a yield of 65%, $^1$H NMR (300 MHz, Chloroform-d) δ 8.29 (s, 1H), 7.74 (s, 1H), 7.50 (q, J=7.7 Hz, 3H), 7.39 (d, J=7.9 Hz, 1H), 7.27 (d, J=5.9 Hz, 1H), 7.19-6.98 (m, 5H), 6.79-6.71 (m, 2H), 6.62 (s, 1H), 4.37 (d, J=6.6 Hz, 2H). 3.94 (s, 1H), 3.82-3.71 (m, 3H), 3.59 (d, J=6.7 Hz, 3H), 2.79 (s, 1H), 2.49 (t, J=7.7 Hz, 1H), 1.29-1.19 (m, 3H); ESI-MS m/z: 553.1 [M+H]$^+$.

Synthesis of (S)-methyl 3-((3-chlorobenzyl) (4-((4-methoxy-N-(2-methoxy-2-oxoethyl) phenyl) sulfonamido) naphthalen-1-yl) amino) butanoate (67)

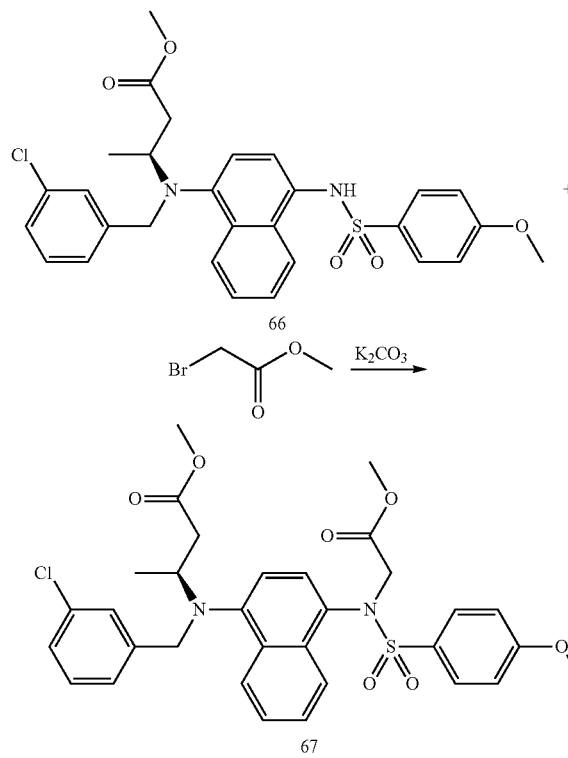

In the same way as the synthesis method of compound 49, reaction is performed on compound 66 (0.10 g, 0.18 mmol), methyl bromoacetate (34.51 mg, 0.22 mmol) and K$_2$CO$_3$ (74.52 mg, 0.54 mmol) as starting materials to obtain a pale yellow solid 67 of 63.50 mg with yield of 57%; ESI-MS m/z: 625.2 [M+H]$^+$.

Synthesis of (S)-3-((3-chlorobenzyl) (4-((4-methoxyphenyl) sulfonamido) naphthalen-1-yl) amino) butanoic acid (DDO-1172)

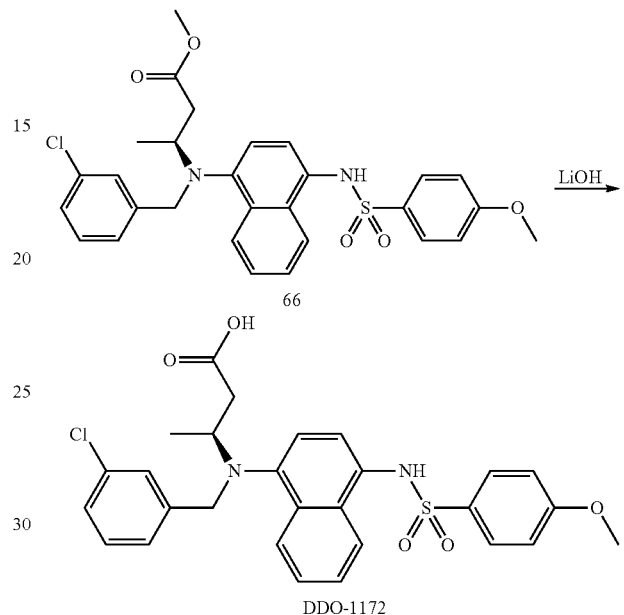

DDO-1172

In the same way as the synthesis method of compound DDO-1160, reaction is performed on compound 66 (0.10 g, 0.18 mmol) and 2M aqueous LiOH (1.00 mL, 2.00 mmol) as starting materials to obtain a white solid DDO-1172 of 56.40 mg with yield of 58%; $^1$H NMR (300 MHz, DMSO-d$_6$) δ 9.79 (s, 1H), 8.30 (d, J=8.5 Hz, 1H), 7.97 (d, J=8.5 Hz, 1H), 7.49 (d, J=8.7 Hz, 3H), 7.44-7.32 (m, 2H), 7.28 (d, J=7.3 Hz, 1H), 7.22 (d, J=8.2 Hz, 1H), 7.17-7.09 (m, 2H), 6.94 (d, J=8.4 Hz, 2H), 6.84 (d, J=8.0 Hz, 1H), 4.34 (t, J=10.4 Hz, 2H), 3.78 (s, 3H), 3.65 (s, 1H), 2.71 (s, 1H), 2.57 (s, 0H), 1.22 (s, 3H); HRMS(ESI): found 539.1408 (C$_{28}$H$_{27}$ClN$_2$O$_5$S, [M+H]$^+$, requires 539.1329); HPLC (85: 15 methanol:water with 1‰ TFA): t$_R$=12.96 min, 96.21%.

Synthesis of (S)-3-((4-((N-(Carboxymethyl)-4-methoxyphenyl) sulfonamido) naphthalen-1-yl) (3-chlorobenzyl) amino) butanoic acid (DDO-1173)

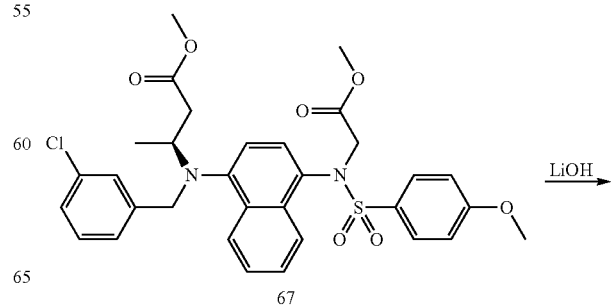

67

-continued

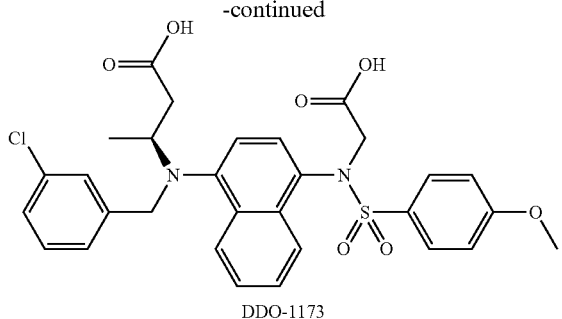

DDO-1173

In the same way as the synthesis method of compound DDO-1161, reaction is performed on compound 67 (63.50 mg, 0.10 mmol) and 2M aqueous LiOH (1.00 mL, 2.00 mmol) as starting materials to obtain a white solid DDO-1173 of 47.30 mg with yield of 78%; $^1$H NMR (300 MHz, DMSO-$d_6$) δ 12.51 (s, 2H), 8.32 (d, J=8.4 Hz, 1H), 8.10 (dd, J=8.5, 4.3 Hz, 1H), 7.59-7.47 (m, 2H), 7.45-7.37 (m, 3H), 7.32 (d, J=7.4 Hz, 1H), 7.22 (dd, J=7.9, 5.0 Hz, 1H), 7.18-7.10 (m, 2H), 7.03-6.87 (m, 3H), 4.49-4.29 (m, 4H), 3.88-3.79 (m, 3H), 3.74 (s, 1H), 2.74 (s, 1H), 2.58 (s, 1H), 1.25 (s, 3H); HRMS(ESI): found 597.1458. ($C_{30}H_{29}ClN_2O_7S$, [M+H]$^+$, requires 597.1384); HPLC (85:15 methanol:water with 1‰ TFA): $t_R$=12.80 min, 98.83%.

Synthesis of (S)-methyl 2-((4-((tert-butoxycarbonyl) amino) naphthalen-1-yl) (3-chlorobenzyl) amino) butanoate (68)

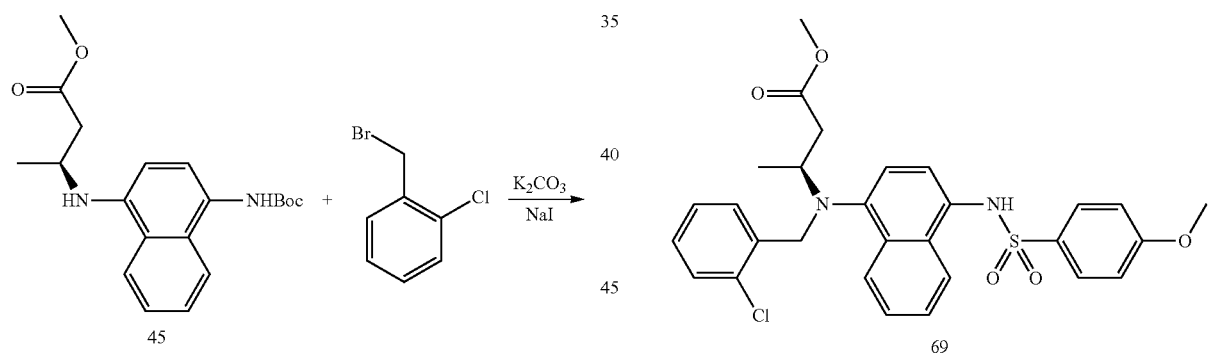

In the same way as the synthesis method of compound 46, reaction is performed on compound 45 (0.36 g, 1.00 mmol), 2-chlorobromide (0.61 g, 3.00 mmol), K$_2$CO$_3$ (0.83 g, 6.00 mmol) and NaI (0.90 g, 6.00 mmol) as starting materials to obtain a pale yellow liquid 68 of 0.36 g with a yield of 75%; $^1$H NMR (300 MHz, Chloroform-d) δ 8.43 (dd, J=8.1, 1.7 Hz, 1H), 7.90-7.82 (m, 1H), 7.67 (d, J=8.1 Hz, 1H), 7.58-7.48 (m, 2H), 7.36 (dd, J=7.6-1.9 Hz, 1H), 7.23 (t, J=7.4 Hz, 2H), 7.05-6.92 (m, 2H), 6.67 (s, 1H), 4.52 (s, 2H), 3.95 (q, J=6.8 Hz, 1H), 3.61 (s, 3H), 2.87 (dt, J=12.9, 6.4 Hz, 1H), 2.56 (dd, J=14.7, 9.1 Hz, 1H), 1.55 (s, 9H), 1.36 (d, J=6.6 Hz, 3H); ESI-MS m/z: 483.2 [M+H]$^+$.

Synthesis of (S)-methyl 2-((3-chlorobenzyl) (4-((4-methoxyphenyl) sulfonamido) naphthalen-1-yl) amino) butanoate (69)

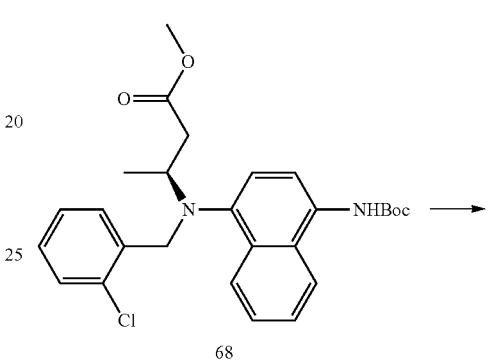

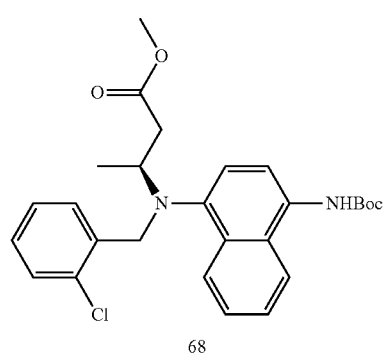

In the same way as the synthesis method of compound 48, after BOC removal, compound 68 (0.36 g, 0.75 mmol) reacts with 4-methoxybenzenesulfonyl chloride (0.19 g, 0.90 mmol) and pyridine (0.18 g, 2.25 mmol) to obtain a white solid 69 of 0.26 g with a yield of 63%; $^1$H NMR (300 MHz, Chloroform-d) δ 8.34 (d, J=10.2 Hz, 1H), 7.83 (t, J=8.3 Hz, 1H), 7.63-7.49 (m, 3H), 7.42 (d, J=7.9 Hz, 1H), 7.28 (t, J=7.6 Hz, 2H), 7.05 (dt, J=22.4, 8.1 Hz, 4H), 6.76 (dt, J=14.8, 7.1 Hz, 3H), 4.51 (d, J=6.8 Hz, 1H), 4.06-3.96 (m, 1H), 3.81 (d. J=6.5 Hz, 3H), 3.59 (d, J=6.6 Hz, 3H), 2.86 (s, 1H), 2.57 (s, 1H), 1.30 (t, J=10.7 Hz, 3H); ESI-MS m/z: 553.1 [M+H]$^+$.

Synthesis of (S)-methyl 2-((3-chlorobenzyl) (4-((4-methoxy-N-(2-methoxy-2-oxoethyl) phenyl) sulfonamide) naphthalen-1-yl) amino) butanoate (70)

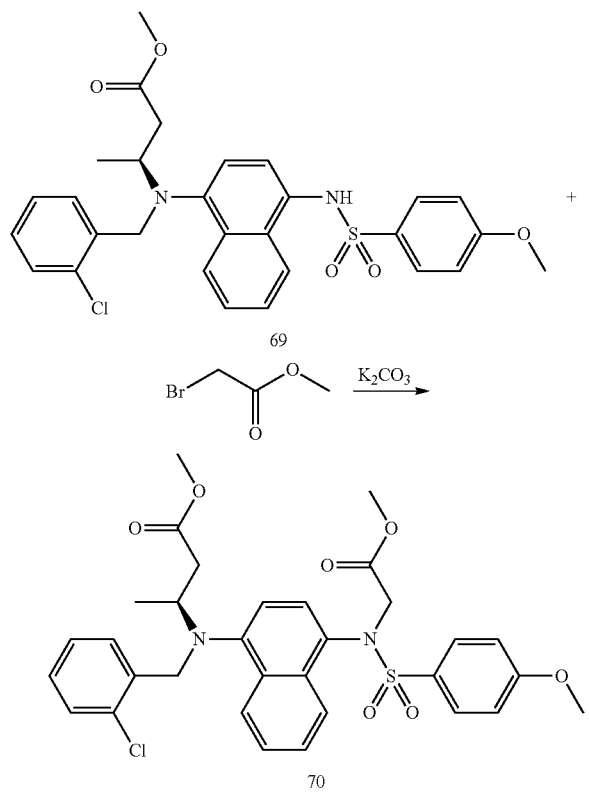

In the same way as the synthesis method of compound 49, reaction is performed on compound 69 (0.10 g, 0.18 mmol), methyl bromoacetate (34.51 mg. 0.22 mmol) and K$_2$CO$_3$ (74.52 mg, 0.54 mmol) as starting materials to obtain a pale yellow solid 70 of 63.20 mg with yield of 56%; ESI-MS m/z: 625.2 [M+H]$^+$.

Synthesis of (S)-3-((2-chlorobenzyl) (4-((4-methoxyphenyl) sulfonamido) naphthalen-1-yl) amino) butanoic acid (DDO-1174)

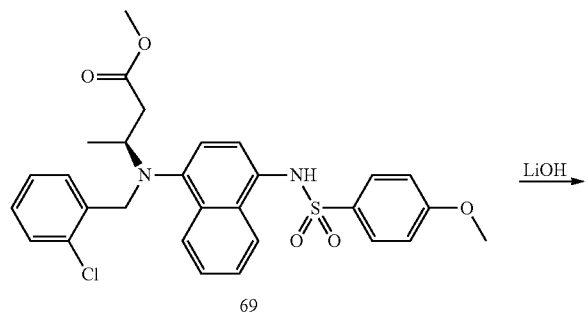

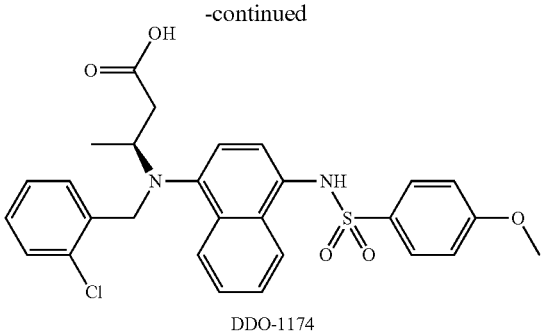

DDO-1174

In the same way as the synthesis method of compound DDO-1160, reaction is performed on compound 69 (0.10 g, 0.18 mmol) and 2M aqueous LiOH (1.00 mL, 2.00 mmol) as starting materials to obtain a white solid DDO-1174 of 53.60 mg with yield of 55%; $^1$H NMR (300 MHz, DMSO-d$_6$) δ 9.81 (s, 1H), 8.31 (d, J=8.5 Hz, 1H), 7.97 (d, J=8.6 Hz, 1H), 7.57-7.45 (m, 3H), 7.42-7.34 (m, 2H), 7.28 (d, 7.8 Hz, 1H), 7.22-7.16 (m, 1H), 7.04 (s, 2H), 6.96-6.79 (m, 3H), 4.44 (d, J=7.0 Hz, 2H), 3.77 (d, J=4.1 Hz, 3H), 3.68 (s, 1H), 2.74 (s, 1H), 2.58 (s, 1H), 1.23 (d, J=15.9 Hz, 3H); HRMS(ESI): found 539.1404. (C$_{28}$H$_{27}$ClN$_2$O$_5$S, [M+H]$^+$, requires 539.1329); HPLC (85:15 methanol:water with 1‰ TFA): t$_R$=13.21 min, 97.20%.

Synthesis of (S)-3-((4-((N-(Carboxymethyl)-4-methoxyphenyl) sulfonamido) naphthalen-1-yl) (2-chlorobenzyl) amino) butanoic acid (DDO-1175)

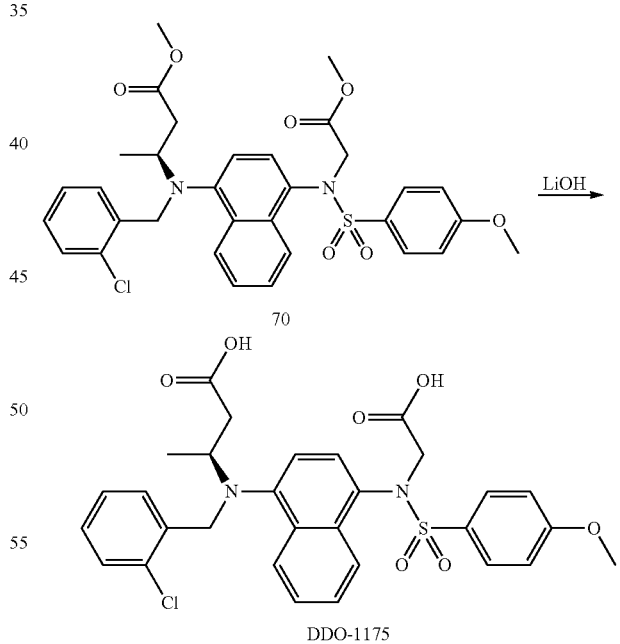

DDO-1175

In the same way as the synthesis method of compound DDO-1161, reaction is performed on compound 70 (63.20 mg, 0.10 mmol) and 2M aqueous LiOH (1.00 mL, 2.00 mmol) as starting materials to obtain a white solid DDO-1175 of 45.60 mg with yield of 75%; $^1$H NMR (300 MHz, DMSO-d$_6$) δ 12.53 (s, 2H), 8.34 (d, J=8.5 Hz, 1H), 8.12 (t, J=7.5 Hz, 1H), 7.52 (d, J=11.3 Hz, 2H), 7.41 (qd, J=7.1, 4.6, 3.4 Hz, 3H), 7.32 (d, J=6.7 Hz, 1H), 7.17 (dd, J=8.9, 3.3 Hz, 1H), 7.11 (dd, J=9.9, 4.4 Hz, 2H), 6.96 (td, J=10.1, 9.2, 4.0 Hz, 3H), 4.54-4.44 (m, 2H), 4.33 (d, J=8.9 Hz, 2H), 3.87-3.81 (m, 3H), 3.77 (s, 1H), 2.78 (s, 1H), 2.61 (d, J=12.2 Hz, 1H), 1.29 (s, 3H); HRMS(ESI): found 597.1459. ($C_{30}H_{29}ClN_2O_7S$, $[M+H]^+$, requires 597.1384); HPLC (85:15 methanol:water 1‰ TFA): $t_R$=12.67 min, 95.45%.

Synthesis of (S)-methyl 3-((4-((tert-butoxycarbonyl) amino) naphthalen-1-yl) (3-fluorobenzyl) amino) butanoate (71)

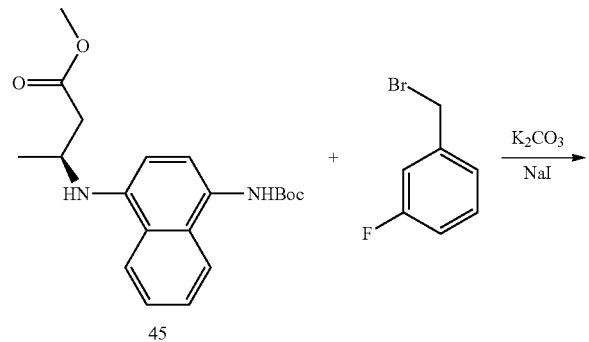

Synthesis of (S)-methyl 3-((3-fluorobenzyl) (4-((4-methoxyphenyl) sulfonamido) naphthalen-1-yl) amino) butanoate (72)

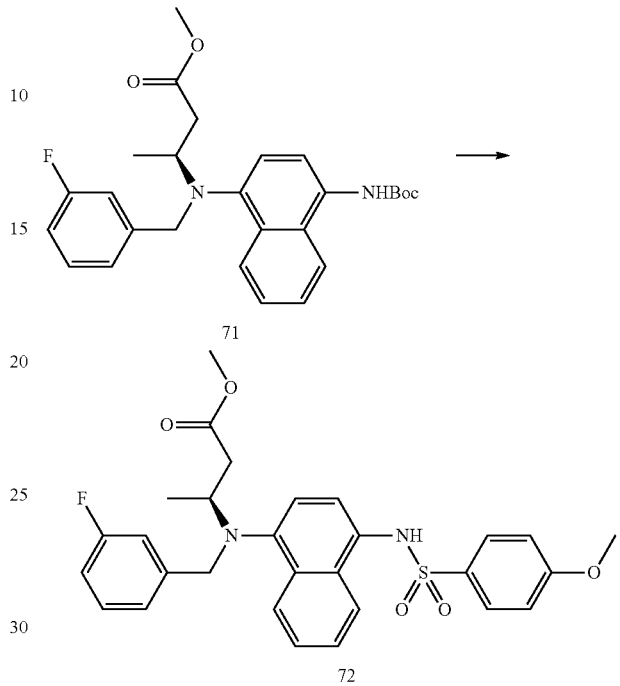

In the same way as the synthesis method of compound 46, reaction is performed on compound 45 (0.36 g, 1.00 mmol), 3-fluorobenzyl bromide (0.57 g, 3.00 mmol), $K_2CO_3$ (0.83 g, 6.00 mmol) and NaI (0.90 g, 6.00 mmol) as starting materials to obtain a pale yellow liquid 71 of 0.33 g with a yield of 71%; ¹H NMR (300 MHz, Chloroform-d) δ 8.30 (d, J=8.1 Hz, 1H), 7.78-7.70 (m, 1H), 7.57 (d, J=8.2 Hz, 1H), 7.48-7.41 (m, 2H), 7.08 (d, J=8.3 Hz, 1H), 7.01-6.94 (m, 3H), 6.71-6.62 (m, 1H), 6.57 (s, 1H), 4.31 (s, 2H), 3.84-3.76 (m, 1H), 3.52 (s, 3H), 2.74 (d, J=13.4 Hz, 1H), 2.41 (dd, J=14.5, 8.9 Hz, 1H), 1.47 (s, 9H), 1.19 (s, 3H); ESI-MS m/z: 467.2 $[M+H]^+$.

In the same way as the synthesis method of compound 48, after BOC removal, compound 71 (0.33 g, 0.71 mmol) reacts with 4-methoxybenzenesulfonyl chloride (0.17 g, 0.85 mmol) and pyridine (0.16 g, 2.03 mmol) to obtain a white solid 72 of 0.23 g with a yield of 61% ¹H NMR (300 MHz, Chloroform-d) δ 8.29 (d, J=8.4 Hz, 1H), 7.74 (d, J=8.4 Hz, 1H), 7.56-7.44 (m, 3H), 7.42-7.37 (m, 1H), 7.27 (s, 1H), 7.19-7.08 (m, 2H), 7.08-6.95 (m, 3H), 6.82-6.70 (m, 3H), 6.64 (s, 1H), 4.40 (s, 2H), 3.95 (q, J=6.6 Hz, 1H), 3.78 (s, 3H), 3.58 (s, 3H), 2.79 (t, J=7.3 Hz, 1H), 2.50 (dd, J=14.5, 8.2 Hz, 1H), 1.29 (d, J=8.7 Hz, 3H); ESI-MS m/z: 537.2 $[M+H]^+$.

Synthesis of (S)-methyl 3-((3-fluorobenzyl) (4-((4-methoxy-N-(2-methoxy-2-oxoethyl) phenyl) sulfonamido) naphthalen-1-yl) amino) butanoate (73)

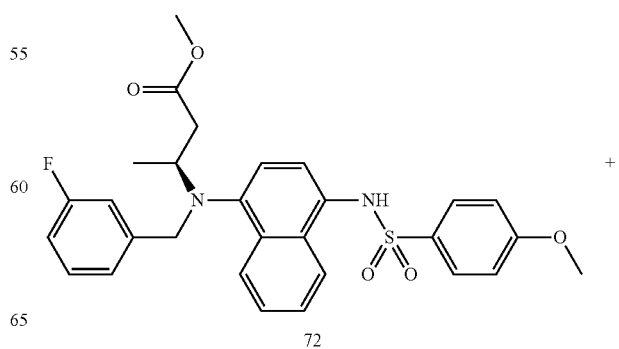

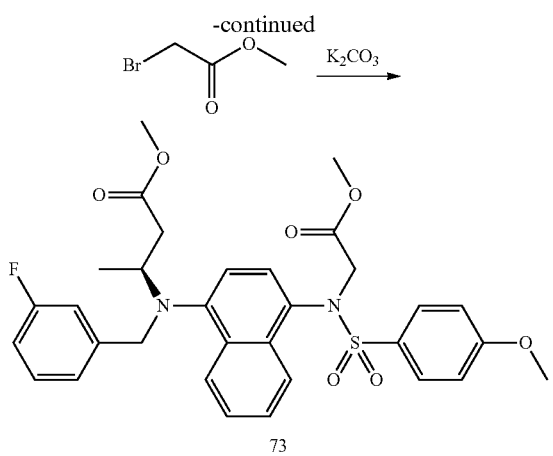

In the same way as the synthesis method of compound 49, reaction is performed on compound 72 (0.10 g, 0.19 mmol), methyl bromoacetate (34.51 mg, 0.26 mmol) and K$_2$CO$_3$ (77.81 mg, 0.56 mmol) as starting materials to obtain a pale yellow solid 73 of 53.30 mg with yield of 46%; ESI-MS m/z: 609.2 [M+H]$^+$.

Synthesis of (S)-3-((3-fluorobenzyl) (4-((4-methoxyphenyl) sulfonamido) naphthalen-1-yl) amino) butanoic acid (DDO-1176)

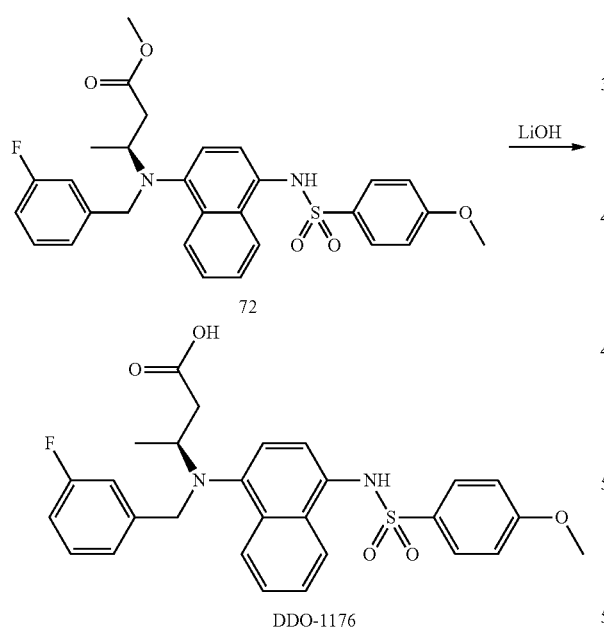

In the same way as the synthesis method of compound DDO-1160, reaction is performed on compound 72 (0.10 g, 0.19 mmol) and 2M aqueous LiOH (1.00 mL, 2.00 mmol) as starting materials to obtain a white solid DDO-1176 of 53.00 mg with yield of 54%; $^1$H NMR (300 MHz, DMSO-d$_6$) δ 9.78 (d, J=3.6 Hz, 1H), 8.31 (d, J=8.5 Hz, 1H), 7.97 (d, J=8.4 Hz, 1H), 7.47 (ddd, J=16.5, 10.8, 6.6 Hz, 4H), 7.23-7.03 (m, 4H), 6.97-6.75 (m, 4H), 4.45-4.28 (m, 2H), 3.77 (d, J=3.4 Hz, 3H), 3.69-3.62 (m, 1H), 2.70 (dd, 2H), 1.22 (s, 3H); FIRMS(ESI): found 523.1702. (C$_{28}$H$_{27}$FN$_2$O$_5$S, [M+H]$^+$, requires 523.1625); HPLC (85:15 methanol:water with 1‰ TFA): t$_R$=11.99 min, 96.23%.

Synthesis of (S)-3-((4-((N-(carboxymethyl)-4-methoxyphenyl) sulfonamido) naphthalen-1-yl) (3-fluorobenzyl) amino) butanoic acid (DDO-1177)

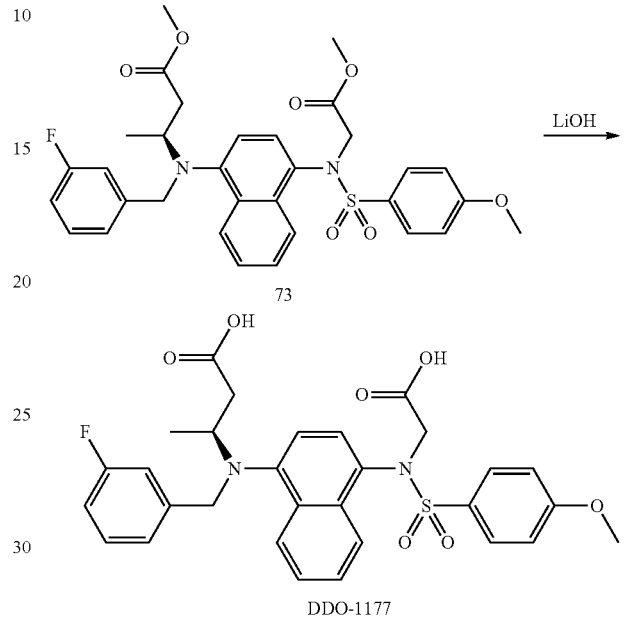

In the same way as the synthesis method of compound DDO-1161, reaction is performed on compound 73 (53.30 mg, 0.10 mmol) and 2M aqueous LiOH (1.00 mL, 2.00 mmol) as starting materials to obtain a white solid DDO-1177 of 44.30 mg with yield of 76%; $^1$H NMR (300 MHz, DMSO-d$_6$) δ 12.50 (s, 2H), 8.33 (d, J=8.4 Hz, 1H), 8.15-8.05 (m, 1H), 7.58-7.37 (m, 4H), 7.24-7.12 (m, 4H), 7.00-6.85 (m, 4H), 4.43-4.26 (m, 4H), 3.86-3.79 (m, 3H), 3.76 (s, 1H), 2.73 (s, 1H), 2.58 (s, 1H), 1.25 (s, 3H); HRMS(ESI): found 5811752 (C$_{30}$H$_{29}$FN$_2$O$_7$S, [M+H]$^+$, requires 581.1680); HPLC (85:15 methanol:water with 1‰ TFA): t$_R$=11.64 min, 95.96%.

Synthesis of (S)-methyl 3-((4-((tert-butoxycarbonyl) amino) naphthalen-1-yl) (2-fluorobenzyl) amino) butanoate (74)

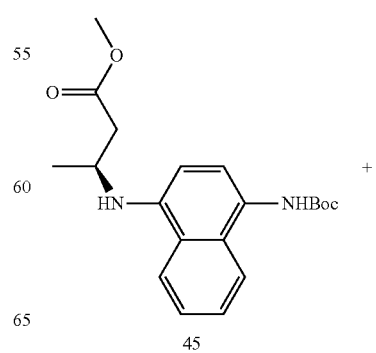

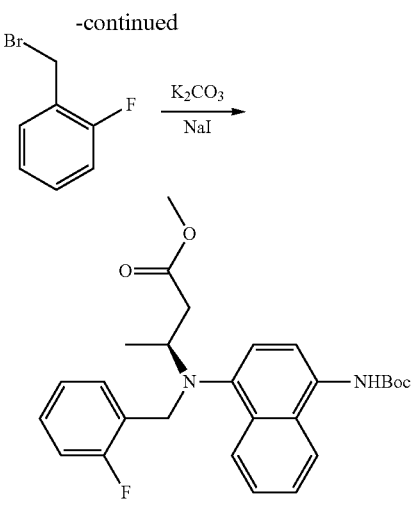

In the same way as the synthesis method of compound 46, reaction is performed on compound 45 (0.36 g, 1.00 mmol), 2-fluorobenzyl bromide (0.57 g, 3.00 mmol), K₂CO₃ (0.83 g, 6.00 mmol) and NaI (0.90 g, 6.00 mmol) as starting materials to obtain a pale yellow liquid 74 of 0.34 g with a yield of 73%; ¹H NMR (300 MHz, Chloroform-d) δ 8.2.9 (s, 7.73 (s, 1H), 7.58 (s, 1H), 7.47-7.36 (m, 2H), 7.22-7.16 (m, 2H), 6.93 (s, 1H), 6.74 (d, J=7.7 Hz, 2H), 6.56 (s, 1H), 4.35 (s, 2H), 3.80 (d, J=9.3 Hz, 1H), 3.51 (d, J=5.2 Hz, 3H), 2.73 (d, J=6.8 Hz, 1H), 2.49-2.40 (m, 1H), 1.44 (s, J=5.6 Hz, 9H), 1.24-1.21 (m, 1H), ESI-MS m/z: 467.2 [M+H]⁺.

Synthesis of (S)-methyl 2-((3-fluorobenzyl) (4-((4-methoxyphenyl) sulfonamido) naphthalen-1-yl) amino) butanoate (75)

In the same way as the synthesis method of compound 48, after BOC removal, compound 74 (0.34 g, 0.73 mmol) reacts with 4-methoxybenzenesulfonyl chloride (0.18 g, 0.88 mmol) and pyridine (0.17 g, 2.19 mmol) to obtain a white solid 75 of 0.24 g with a yield of 62%; ¹H NMR (300 MHz, Chloroform-d) δ 8.34-8.26 (m, 1H), 7.79 (d, J=8.3 Hz, 1H), 7.58-7.51 (m, 2H), 7.49-7.43 (m, 1H), 7.42-7.36 (m, 1H), 7.27-7.21 (m, 1H), 7.10 (dq, J=14.8, 7.6, 7.0 Hz, 3H), 6.95-6.87 (m, 1H), 6.85-6.80 (m, 1H), 6.75 (d, J=9.1 Hz, 3H), 4.43 (s, 2H), 3.93 (m, J=10.5, 4.4 Hz, 1H), 3.79 (s, 3H), 3.59 (s, 3H), 2.89-2.78 (m, 1H), 2.52 (dd, J=14.6, 8.5 Hz, 1H), 1.35 (d, J=6.6 Hz, 3H); ESI-MS m/z: 537.2 [M+H]⁺.

Synthesis of (S)-methyl 2-((3-fluorobenzyl) (4-((4-methoxy-N-(2-methoxy-2-oxoethyl) phenyl) sulfonamido) naphthalen-1-yl) amino) butanoate (76)

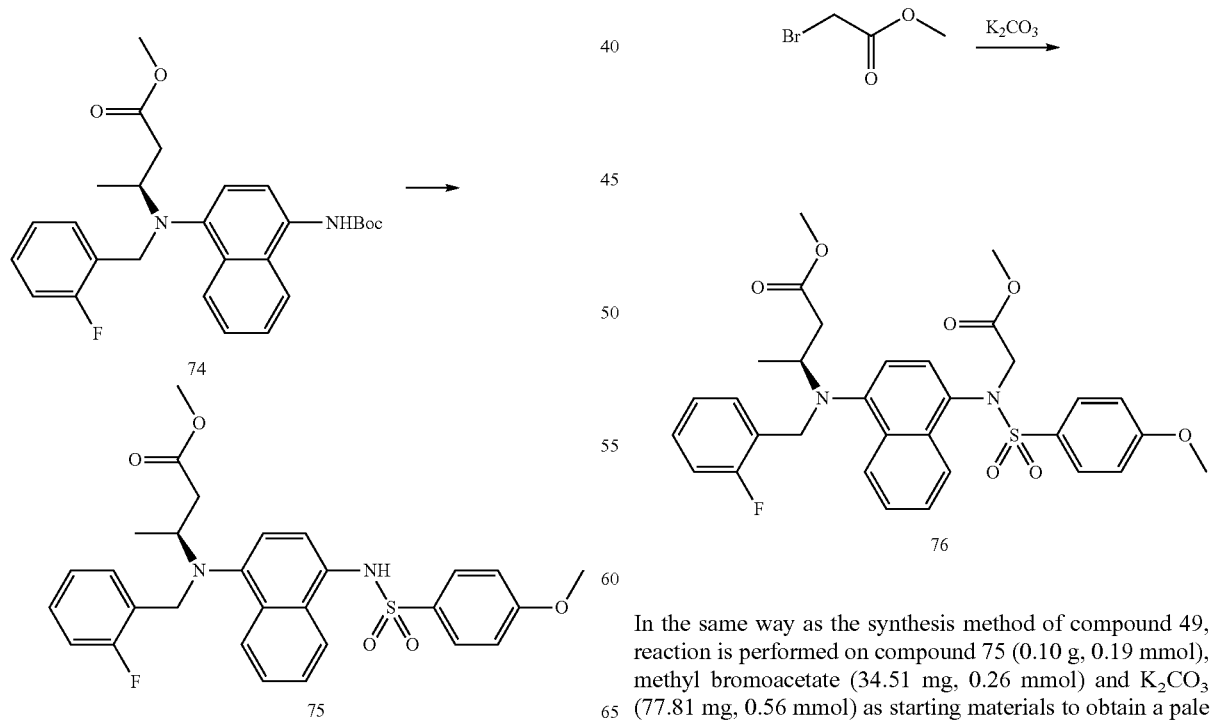

In the same way as the synthesis method of compound 49, reaction is performed on compound 75 (0.10 g, 0.19 mmol), methyl bromoacetate (34.51 mg, 0.26 mmol) and K₂CO₃ (77.81 mg, 0.56 mmol) as starting materials to obtain a pale yellow solid 76 of 64.20 mg with yield of 56%; ESI-MS m/z: 609.2 [M+H]⁺.

Synthesis of (S)-3-((2-fluorobenzyl) (4-((4-methoxyphenyl) sulfonamido) naphthalen-1-yl) amino) butanoic acid (DDO-1178)

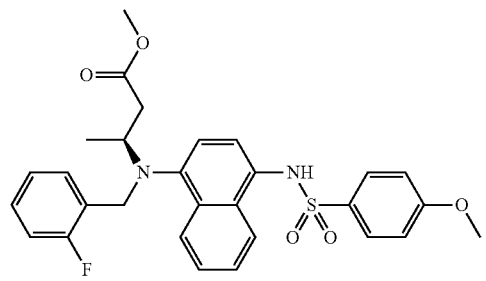

75

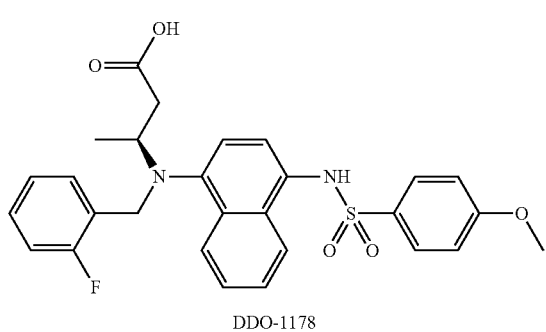

DDO-1178

In the same way as the synthesis method of compound DDO-1160, reaction is performed on compound 75 (0.10 g, 0.19 mmol) and 2M aqueous LiOH (1.00 mL, 2.00 mmol) as starting materials to obtain a white solid DDO-1178 of 53.80 mg with yield of 54%; $^1$H NMR (300 MHz, DMSO-$d_6$) δ 9.77 (s, 1H), 8.24 (d, J=8.3 Hz, 1H), 7.95 (d, J=8.4 Hz, 1H), 7.48 (d, J=8.4 Hz, 3H), 7.38 (t, 7.5 Hz, 1H), 7.31 (s, 1H), 7.23 (d, J=8.0 Hz, 1H), 7.09 (d, J=7.1 Hz, 1H), 7.01 (d, J=9.4 Hz, 1H), 6.91 (dd, J=12.6, 8.1 Hz, 4H), 4.38 (d, J=9.4 Hz, 2H), 3.78 (s, 3H), 3.64 (s, 1H), 2.71 (s, 1H), 2.60 (s, 1H), 1.26 (s, 3H); HRMS(ESI): found 523.1708 ($C_{28}H_{27}FN_2O_5S$, [M+M]$^+$, requires 523.1625); HPLC (85:15 methanol:water with 1% TEA): $t_R$=14.60 min, 97.52%.

Synthesis of (S)-3-(4-((N-(carboxymethyl)-4-methoxyphenyl) sulfonamido) naphthalen-1-yl) (2-fluorobenzyl) amino) butanoic acid (DDO-1179)

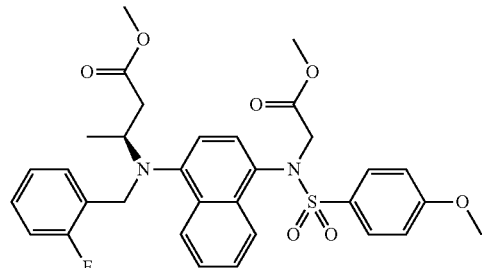

76

LiOH →

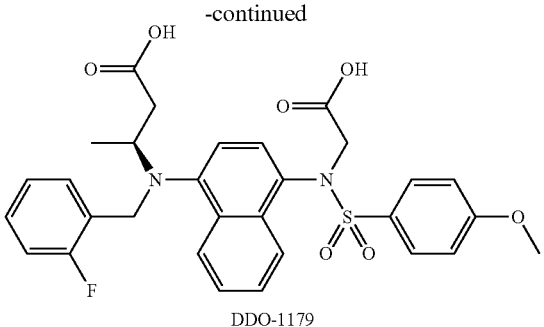

DDO-1179

In the same way as the synthesis method of compound DDO-1161, reaction is performed on compound 76 (64.20 mg, 0.10 mmol) and 2M aqueous LiOH (1.00 mL, 2.00 mmol) as starting materials to obtain a white solid DDO-1179 of 42.10 mg with yield of 72%; $^1$H NMR (300 MHz, DMSO-$d_6$) δ 8.27 (d, J=8.3 Hz, 1H), 8.09 (t, J=7.1 Hz, 1H), 7.61-7.30 (m, 5H), 7.23 (d, J=8.1 Hz, 1H), 7.13 (d, J=6.8 Hz, 1H), 7.10-7.03 (m, 1H), 6.98 (dq, J=9.7, 5.3, 4.0 Hz, 4H), 4.38 (dd, J=26.3, 10.6 Hz, 4H), 3.84 (d, J=1.9 Hz, 3H), 3.73 (s, 1H), 2.74 (s, 1H), 2.60 (d, J=11.4 Hz, 1H), 1.2.9 (s, 3H); HRMS(ESI): found 581.1758. ($C_{30}H_{29}FN_2O_7S$, [M+H]$^+$, requires 581.1680); HPLC (85:15 methanol:water with 1‰ TFA): $t_R$=12.20 min, 100.00%.

IV. Synthesis of Four-Phenyl Ring Electron Isostere-Substituted Compound

Synthesis of (S)-methyl 3-((4-((tert-butoxycarbonyl) amino) naphthalen-1-yl) (prop-2-yn-1-yl) amino) butanoate (77)

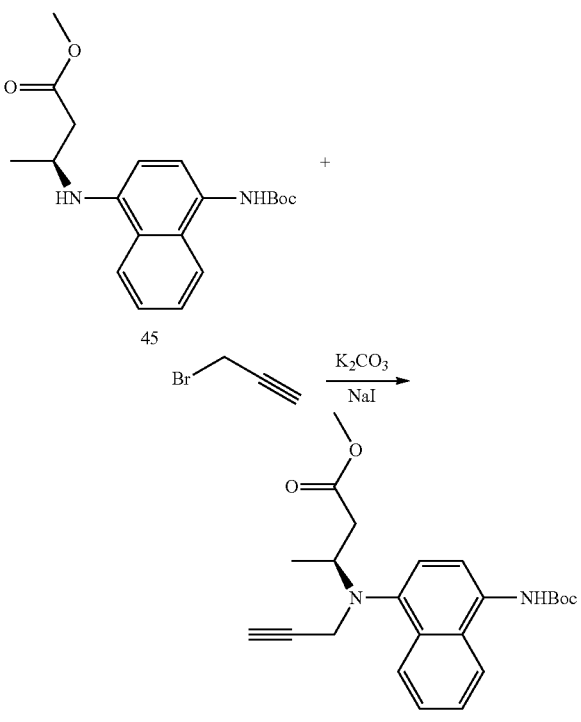

77

In the same way as the synthesis method of compound 46, reaction is performed on compound 45 (0.72 g, 2.00 mmol), 3-bromopropyne (0.71 g, 6.00 mmol), K$_2$CO$_3$ (1.66 g, 12.00 mmol) and NaI (1.80 g, 12.00 mmol) as starting materials to obtain a pale yellow liquid 77 of 0.43 g with a yield of 53%; $^1$H NMR. (300 MHz, Chloroform-d) δ 8.37-8.26 (m, 1H), 7.92-7.75 (m, 2H), 7.59-7.47 (m, 3H), 6.81 (s, 1H), 4.14-3.97 (m, 2H), 3.89 (s, 1H), 3.61 (d, J=1.9 Hz, 3H), 2.69 (dd, J=14.8, 4.6 Hz, 1H), 2.39 (dd, J=14.9, 9.0 Hz, 1H), 2.26-2.16 (m, 1H), 1.57 (s, 9H), 1.36-1.30 (s, 3H); ESI-MS m/z: 397.2 [M+H]$^+$.

VI. Synthesis of Propynyl-Substituted Derivatives

Synthesis of (S)-methyl 3-((4-(phenylsulfonamido) naphthalen-1-yl) (prop-2-yn-1-yl) amino) butanoate (86)

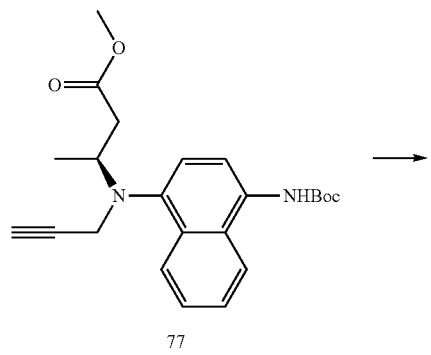

In the same way as the synthesis method of compound 48, after BOC removal, compound 77 (0.28 g, 0.71 mmol) reacts with benzenesulfonyl chloride (0.15 g, 0.85 mmol) and pyridine (0.17 g, 2.13 mmol) to obtain a white solid 86 of 0.22 g with a yield of 71%; $^1$H NMR (300 MHz, Chloroform-d) δ 8.23 (d, J=8.3 Hz, 1H), 7.77 (t, J=8.5 Hz, 3H), 7.53-7.44 (m, 2H), 7.39 (q, J=8.2, 6.8 Hz, 4H), 7.33 (s, 1H), 6.78 (s, 1H), 4.07-4.00 (m, 1H), 3.97-3.81 (m, 2H), 3.60 (s, 3H), 2.67 (dd, J=14.9, 4.8 Hz, 1H), 2.41 (dd, J=14.9, 8.5 Hz, 1H), 2.21 (d, J=2.4 Hz, 1H), 1.34-1.26 (m, 3H); ESI-MS m/z: 437.1 [M+H]$^+$.

Synthesis of (S)-methyl 3-((4-(N-(2-methoxy-2-oxoethyl) benzenesulfonamido) naphthalen-1-yl) (prop-2-yn-1-yl) amino) butanoate (87)

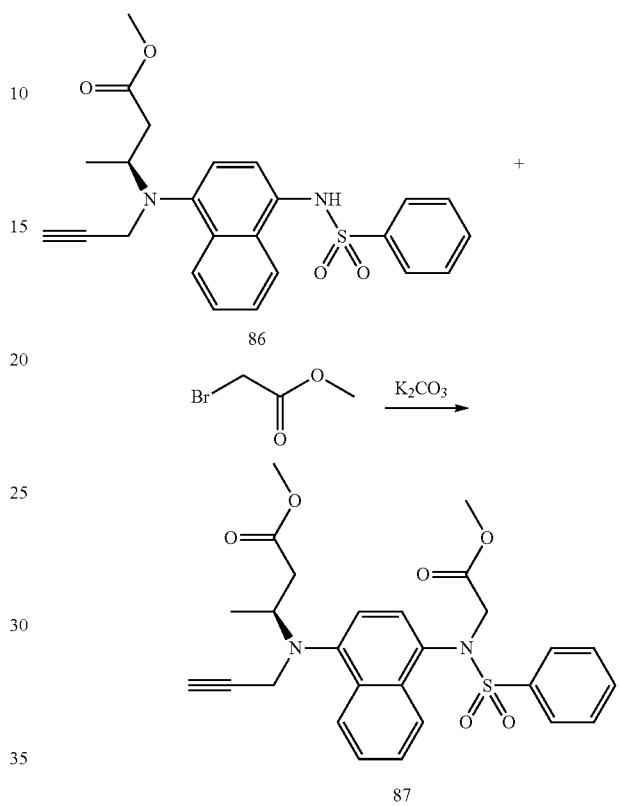

In the same way as the synthesis method of compound 49, reaction is performed on compound 86 (0.10 g, 0.23 mmol), methyl bromoacetate (42.23 mg, 0.27 mmol) and K$_2$CO$_3$ (95.22 mg, 0.69 mmol) as starting materials to obtain a pale yellow solid 87 of 72.40 mg with yield of 59%; ESI-MS m/z: 509.2 [M+H]$^+$.

Synthesis of (S)-3-((4-(phenylsulfonamido) naphthalen-1-yl)(prop-2-yn-1-yl) amino) butanoic acid (DDO-1186)

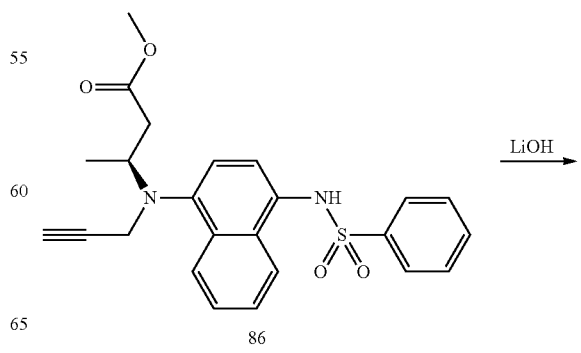

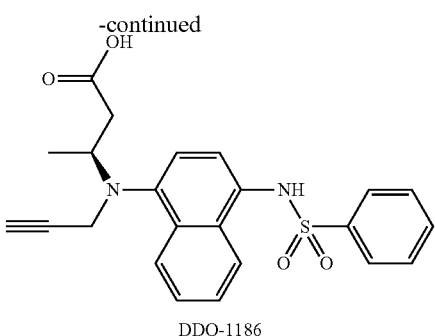

DDO-1186

In the same way as the synthesis method of compound DDO-1160, reaction is performed on compound 86 (0.10 g, 0.23 mmol) and 2M aqueous LiOH (1.00 mL, 2.00 mmol) as starting materials to obtain a white solid DDO-1186 of 53.60 mg with yield of 55%; $^1$H NMR (300 MHz, DMSO-$d_6$) δ 12.23 (s, 1H), 10.11 (s, 1H), 8.14 (d, J=8.3 Hz, 1H), 7.97 (d, J=8.3 Hz, 1H), 7.75-7.63 (m, 2H), 7.58 (d, J=7.1 Hz, 1H), 7.46 (dt, J=20.6, 7.5 Hz, 4H), 7.27 (d, J=8.1 Hz, 1H), 7.03 (d, J=8.0 Hz, 1H), 4.03-3.82 (m, 2H), 3.69 (s, 1H), 2.97 (t, J=2.2 Hz, 1H), 2.57 (s, 1H), 2.40-2.31 (m, 1H), 1.17 (d, J=6.4 Hz, 3H); HRMS(ESI): found 423.1379 ($C_{23}H_{22}N_2O_4S$, [M+H]$^+$, requires 423.1300); HPLC (85:15 methanol:water with 1‰ TFA): $t_R$=9.70 min, 95.72%.

Synthesis of (S)-3-((4-(N-(carboxymethyl) benzenesulfonamido) naphthalen-1-yl) (prop-2-yn-1-yl) amino) butanoic acid (DDO-1187)

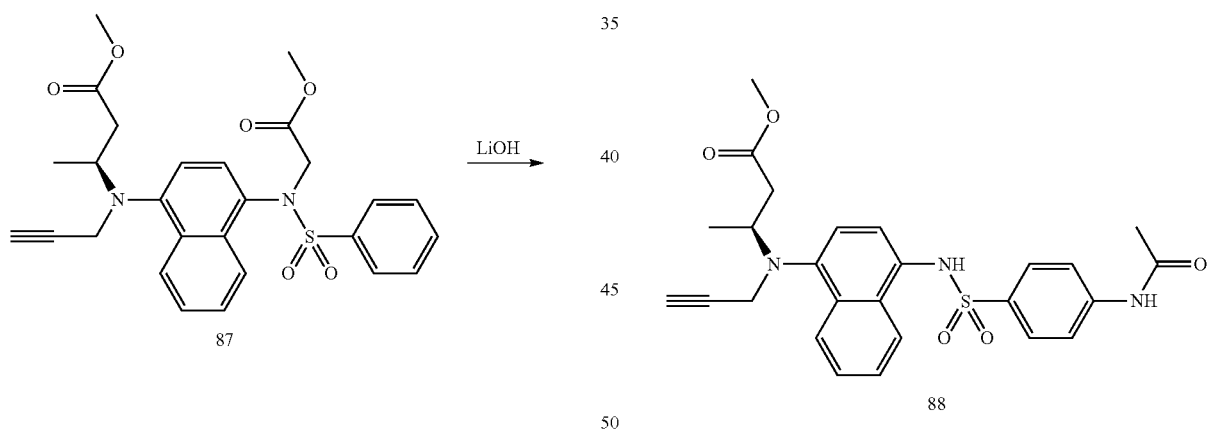

In the same way as the synthesis method of compound DDO-1161, reaction is performed on compound 87 (72.40 mg, 0.14 mmol) and 2M aqueous LiOH (1.50 mL, 3.00 mmol) as starting materials to obtain a white solid DDO-1187 of 47.30 mg with yield of 74%; $^1$H NMR (300 MHz, DMSO-$d_6$) δ 12.64 (s, 2H), 8.23 (d, J=7.9 Hz, 1H), 8.11 (d, J=7.7 Hz, 1H), 7.70 (d, J=3.5 Hz, 5H), 7.58 (s, 2H), 7.35 (d, J=8.1 Hz, 1H), 7.26 (d, J=7.9 Hz, 1H), 4.63 (d, J=17.9 Hz, 1H), 4.42 (dd, J=17.5, 3.3 Hz, 1H), 4.04 (s, 2H), 3.82 (s, 1H), 3.09 (d, J=3.9 Hz, 1H), 2.65 (d, 1H), 2.48 (d, J=4.0 Hz, 1H), 1.31-1.24 (m, 3H); HRMS(ESI): found 481.1436 ($C_{25}H_{24}N_2O_6S$, [M+H]$^+$, requires 481.1355); HPLC (85:15 methanol:water with 1‰ TFA): $t_R$=9.55 min, 100.00%.

Synthesis of (S)-methyl 3-((4-((4-acetamidophenyl) sulfonamido) naphthalen-1-yl) (prop-2-yn-1-yl) amino) butanoate (88)

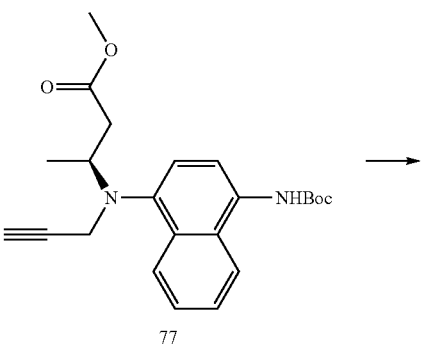

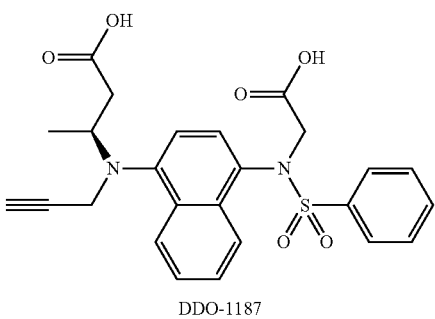

In the same way as the synthesis method of compound 48, after BOC removal, compound 77 (0.28 g, 0.71 mmol) reacts with 4-methoxybenzene sulfonyl chloride (0.20 g, 0.85 mmol) and pyridine (0.17 g, 2.13 mmol) to obtain a white solid 88 of 0.25 g with a yield of 71%; $^1$H NMR (300 MHz, Chloroform-d) δ 8.24 (d, J=8.2 Hz, 1H), 7.88 (d, J=8.0 Hz, 1H), 7.69-7.61 (m, 3H), 7.55 (d, J=8.6 Hz, 3H), 7.47 (s, 1H), 7.45-7.37 (m, 2H), 6.94 (s, 1H), 4.04 (s, 1H), 4.01-3.83 (m, 2H), 3.63 (s, 4H), 2.68 (dd, J=14.9, 4.7 Hz, 1H), 2.50-2.39 (m, 1H), 2.29-2.24 (m, 1H), 2.20 (s, 3H), 1.36 (d, J=6.9 Hz, 3H); ESI-MS m/z: 494.2 [M+H]$^+$.

Synthesis of (S)-methyl 3-((4-((4-acetamido-N-(2-methoxy-2-oxoethyl) phenyl) sulfamido) naphthalen-1-yl)(prop-2-yn-1-yl) aminomethyl) butanoate (89)

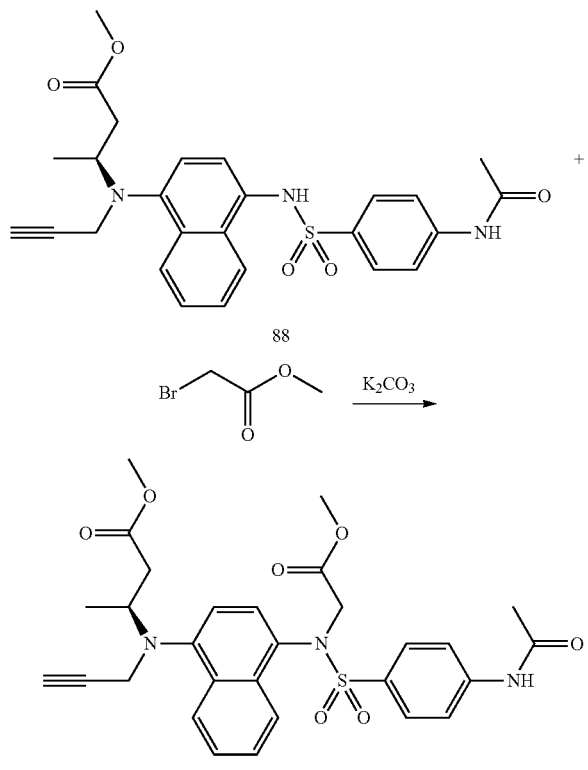

In the same way as the synthesis method of compound 49, reaction is performed on compound 88 (0.10 g, 0.20 mmol), methyl bromoacetate (36.72 mg, 0.24 mmol) and $K_2CO_3$ (82.80 mg, 0.60 mmol) as starting materials to obtain a pale yellow solid 89 of 70.20 mg with yield of 62%; ESI-MS m/z: 566.2 [M+H]$^+$.

Synthesis of (S)-3-((4-((4-acetamidophenyl) sulfonamido) naphthalen-1-yl) (prop-2-yn-1-yl) amino) butanoic acid (DDO-1188)

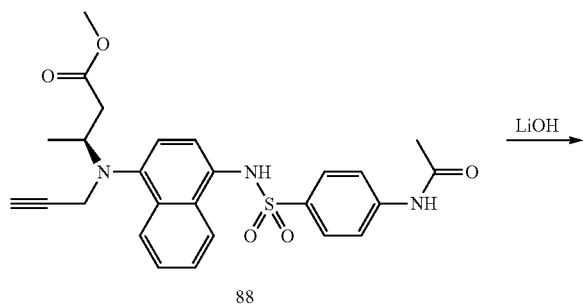

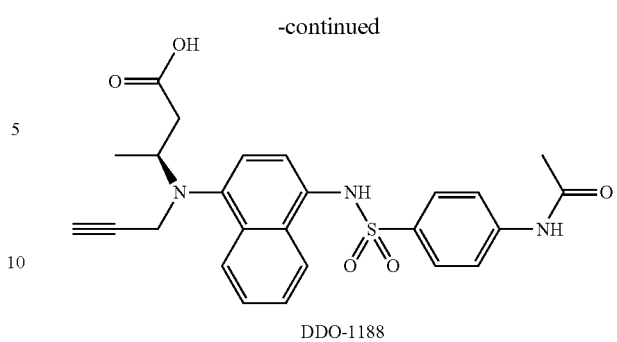

In the same way as the synthesis method of compound DDO-1160, reaction is performed on compound 88 (0.10 g, 0.20 mmol) and 2M aqueous LiOH (1.00 mL, 2.00 mmol) as starting materials to obtain a white solid DDO-1188 of 58.60 mg with yield of 60%; $^1$H NMR (300 MHz, DMSO-d$_6$) δ 10.32 (s, 1H), 9.99 (s, 1H), 8.09 (dd, J=37.2, 7.9 Hz, 2H), 7.65 (d, J=15.3 Hz, 3H), 7.48 (d, J=9.4 Hz, 2H), 7.28 (d, J=8.7 Hz, 1H), 7.04 (s, 1H), 3.93 (s, 2H), 3.71 (s, 1H), 2.96 (s, 1H), 2.59 (s, 1H), 2.37 (d, J=11.1 Hz, 1H), 2.19-1.94 (m, 3H), 1.17 (d, J=6.2 Hz, 3H); HRMS(ESI): found 480.1591. ($C_{25}H_{25}N_3O_5S$, [M+H]$^+$, requires 480.1515); HPLC (85:15 methanol:water with 19.60 TFA): t$_R$=9.44 min, 96.3%.

Synthesis of (S)-3-((4-((4-acetamido-N-(carboxymethyl) phenyl) sulfonamido) naphthalen-1-yl)(prop-2-yn-1-yl) amino) butanoic acid (DDO-1189)

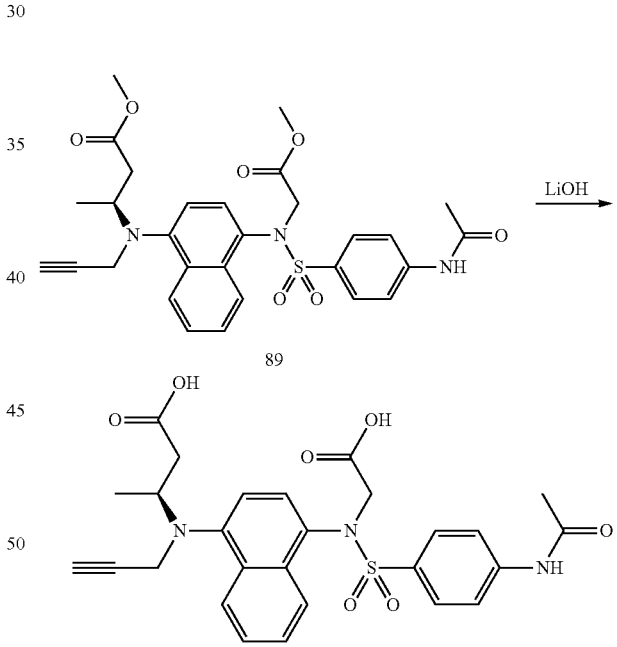

In the same way as the synthesis method of compound DDO-1161, reaction is performed on compound 89 (70.20 mg, 0.12 mmol) and 2M aqueous LiOH (1.50 mL, 3.00 mmol) as starting materials to obtain a white solid DDO-1189 of 46.60 mg with yield of 72%; $^1$H NMR (300 MHz, DMSO-d$_6$) δ 10.39 (s, 1H), 8.16 (s, 2H), 7.82-7.66 (m, 2H), 7.66-7.46 (m, 3H), 7.28 (d, J=8.0 Hz, 1H), 7.13 (s, 1H), 4.44 (d, J=17.8 Hz, 1H), 4.32 (d, J=15.8 Hz, 1H), 3.98 (s, 2H), 3.77 (s, 1H), 2.99 (s, 1H), 2.58 (s, 1H), 2.47-2.37 (m, 1H), 2.11 (s, 3H), 1.20 (s, 3H); HRMS(ESI): found 538.1642. ($C_{27}H_{27}N_3O_7S$, [M+H]$^+$, requires 538.1570); HPLC (85:15 methanol:water with 1‰ TFA): t$_R$=9.38 min, 100.00%.

Synthesis of (S)-methyl 3-((4-((4-fluorophenyl) sulfonamide) naphthalen-1-yl) (prop-2-yn-1-yl) amino) butanoate (90)

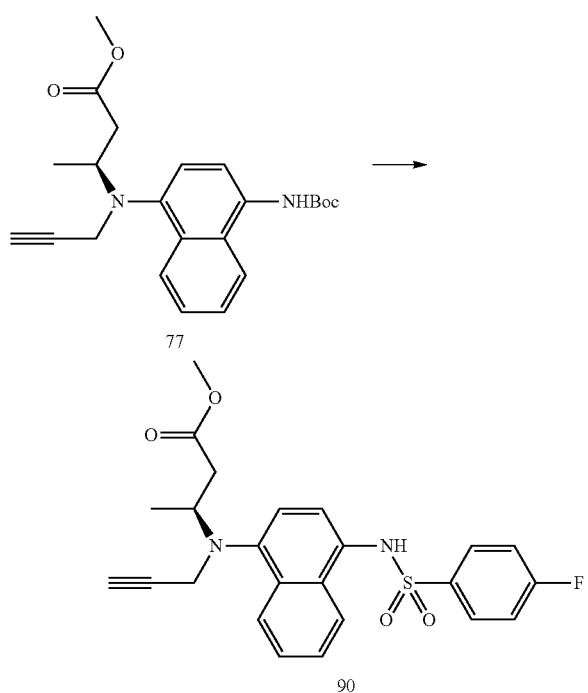

In the same way as the synthesis method of compound 48, after BOC removal, compound 77 (0.28 g, 0.71 mmol) reacts with 4-methoxybenzene sulfonyl chloride (0.14 g, 0.85 mmol) and pyridine (0.17 g, 2.13 mmol) to obtain a white solid 90 of 0.22 g with a yield of 70%; ¹H NMR (300 MHz, Chloroform-d) δ 8.28-8.23 (m, 1H), 7.76 (tt, J=6.9, 2.7 Hz, 3H), 7.54-7.45 (m, 2H), 7.41 (s, 1H), 7.34 (d, J=8.1 Hz, 1H), 7.06 (td, J=9.2, 8.6, 2.5 Hz, 2H), 6.79 (s, 1H), 4.09-4.03 (m, 1H), 3.99-3.86 (m, 2H), 3.62 (s, 3H), 2.68 (dd, J=14.9, 4.8 Hz, 1H), 2.50-2.40 (m, 1H), 2.22 (t, J=2.3 Hz, 1H), 1.36 (d, J=6.4 Hz, 3H). ESI-MS m/z: 454.2 [M+H]⁺.

Synthesis of (S)-methyl 3-((4-((4-fluoro-N-(2-methoxy-2-oxoethyl) phenyl) sulfonamido) naphthalen-1-yl)(prop-2-yn-1-yl) aminomethyl) butanoate (91)

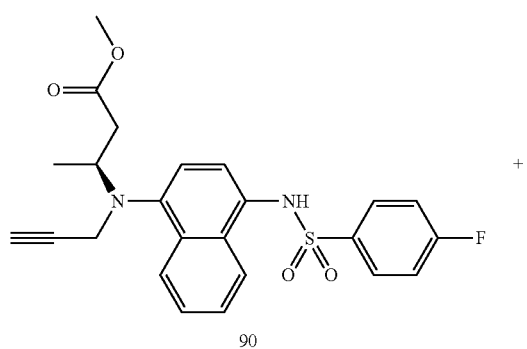

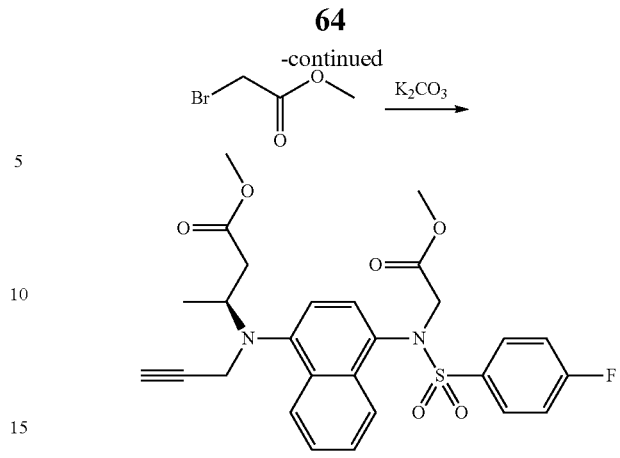

In the same way as the synthesis method of compound 49, reaction is performed on compound 90 (0.10 g, 0.22 mmol), methyl bromoacetate (39.78 mg, 0.26 mmol) and K₂CO₃ (91.08 mg, 0.66 mmol) as starting materials to obtain a pale yellow solid 91 of 74.10 mg with yield of 64%; ESI-MS m/z: 526.2 [M+H]⁺.

Synthesis of (S)-3-((4-((4-fluorophenyl) sulfonamido) naphthalen-1-yl)(prop-2-yn-1-yl) amino) butanoic acid (DDO-1190)

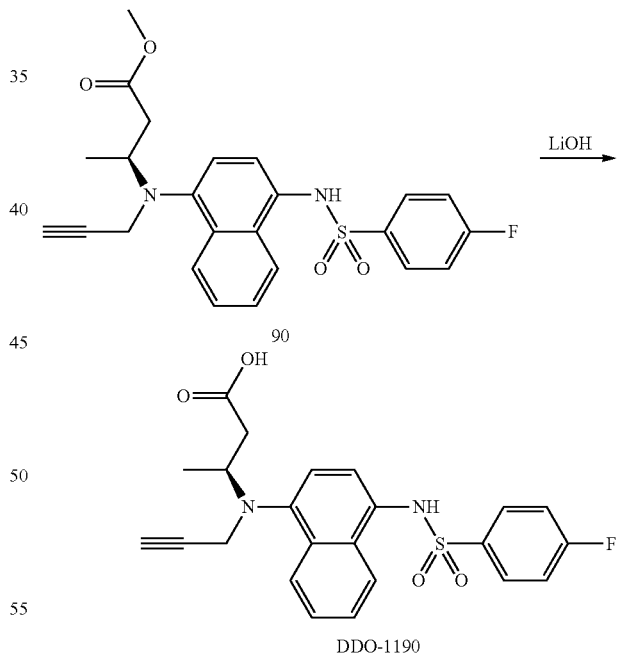

In the same way as the synthesis method of compound DDO-1160, reaction is performed on compound 90 (0.10 mg, 0.21 mmol) and 2M aqueous LiOH (1.00 mL, 2.00 mmol) as starting materials to obtain a white solid DDO-1190 of 56.20 mg with yield of 59%; ¹H NMR (300 MHz, DMSO-d₆) δ 8.28 (dd, J=7.5, 1.4 Hz, 1H), 8.01-7.94 (m, 2H), 7.70-7.60 (m, 2H), 7.52 (td, J=7.4, 1.7 Hz, 1H), 7.38-7.30 (m, 2H), 6.99 (d, J=7.5 Hz, 1H), 6.59 (d, J=7.5 Hz, 1H), 6.29 (s, 1H), 4.29 (dd, J=12.4, 3.0 Hz, 1H), 4.01-3.89

(m, 2H), 2.91 (dd, J=12.4, 7.0 Hz, 1H), 2.65 (t, J=2.9 Hz, 1H), 2.52 (dd, J=12.4, 7.0 Hz, 1H), 1.35 (d, J=6.8 Hz, 3H). HRMS(ESI): found 441.1276. ($C_{23}H_{21}FN_2O_4S$, $[M+H]^+$, requires 441.1206); HPLC (85:15 methanol:water with 1‰ TFA): $t_R$=9.17 min, 98.41%.

Synthesis of (S)-3-((4-((N-(carboxymethyl)-4-fluorophenyl) sulfonamido) naphthalen-1-yl) (prop-2-yn-1-yl) amino) butanoic acid (DDO-1191)

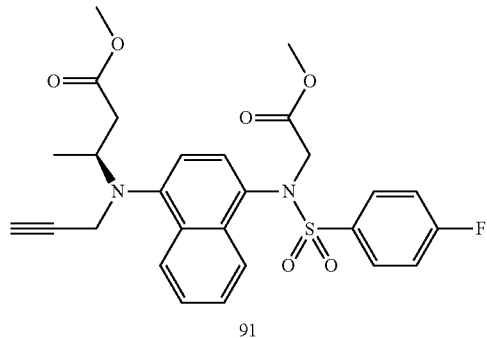

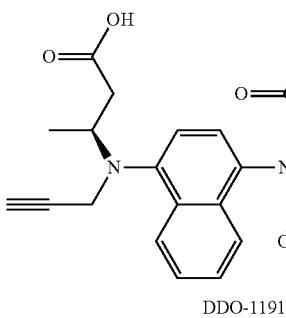

In the same way as the synthesis method of compound DDO-1161, reaction is performed on compound 91 (64.20 mg, 0.12 mmol) and 2M aqueous LiOH (1.50 mL, 3.00 mmol) as starting materials to obtain a white solid DDO-1191 of 46.30 mg with yield of 75%; $^1$H NMR (300 MHz, DMSO-$d_6$) δ 8.25 (dd, J=7.4, 1.6 Hz, 1H), 7.88 (tt, J=8.2, 2.0 Hz, 3H), 7.68 (td, J=7.5, 1.5 Hz, 1H), 7.53 (td, J=7.5, 1.6 Hz, 1H), 7.20-7.12 (m, 2H), 7.03 (d, J=7.4 Hz, 1H), 6.59 (d, J=7.5 Hz, 1H), 4.44 (d, J=17.8 Hz, 1H), 4.32 (d, J=15.8 Hz, 1H), 4.05 (dd, J=12.5, 3.1 Hz, 1H), 3.83 (dd, J=12.5, 2.9 Hz, 1H), 3.75 (h, J=6.9 Hz, 1H), 3.10 (dd, J=12.3, 6.9 Hz, 1H), 2.85-2.76 (m, 2H), 1.35 (d, J=6.8 Hz, 3H). HRMS(ESI): found 499.1333 ($C_{25}H_{23}FN_2O_6S$, $[M+H]^+$, requires 499.1359); HPLC (85:15 methanol:water with 1‰ TFA): tR=9.01 min, 100.00%.

Synthesis of (S)-methyl 3-((4-((4-chlorophenyl) sulfonamido) naphthalen-1-yl) (prop-2-yn-1-yl) amino) butanoate (97)

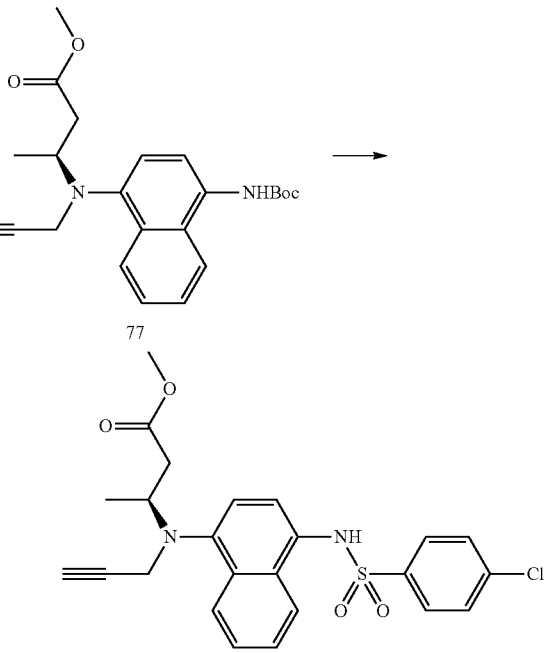

In the same way as the synthesis method of compound 48, after BOC removal, compound 77 (0.28 g, 0.71 mmol) reacts with 4-methoxybenzenesulfonyl chloride (0.18 g, 0.85 mmol) and pyridine (0.17 g, 2.13 mmol) to obtain a white solid 92 of 0.23 g with a yield of 69%; $^1$H NMR (300 MHz, Chloroform-d) δ 8.14 (d, J=8.2 Hz, 1H), 7.68 (d, J=8.1 Hz, 1H), 7.60-7.53 (m, 2H), 7.44-7.31 (m, 3H), 7.25 (s, 1H), 7.20 (d, J=8.5 Hz, 2H), 6.70 (s, 1H), 3.94 (d, J=9.3 Hz, 1H), 3.89-3.74 (m, 2H), 3.51 (s, 3H), 2.63-2.53 (m, 1H), 2.38-2.29 (m, 1H), 2.12 (t, J=2.1 Hz, 1H), 1.25 (d, J=6.3 Hz, 3H), ESI-MS m/z: 471.1 $[M+H]^+$.

Synthesis of (S)-methyl 3-((4-((4-chloro-N-(2-methoxy-2-oxoethyl) phenyl) sulfonamido) naphthalen-1-yl)(prop-2-yn-1-yl) aminomethyl) butanoate (93)

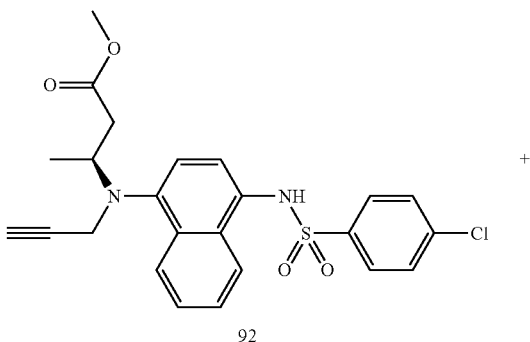

-continued

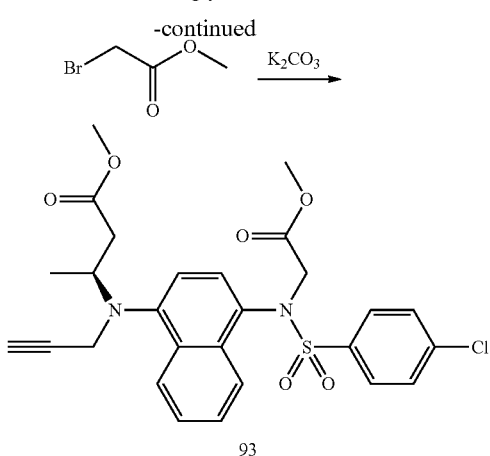

In the same way as the synthesis method of compound 49, reaction is performed on compound 92 (0.10 g, 0.21 mmol), methyl bromoacetate (38.56 mg, 0.25 mmol) and $K_2CO_3$ (86.94 mg, 0.63 mmol) as starting materials to obtain a pale yellow solid 93 of 64.20 mg with yield of 56%; ESI-MS m/z: 543.1 $[M+H]^+$.

Synthesis of (S)-3-((4-((4-chlorophenyl) sulfonamido) naphthalen-1-yl)(prop-2-yn-1-yl) amino) butanoic acid (DDO-1192)

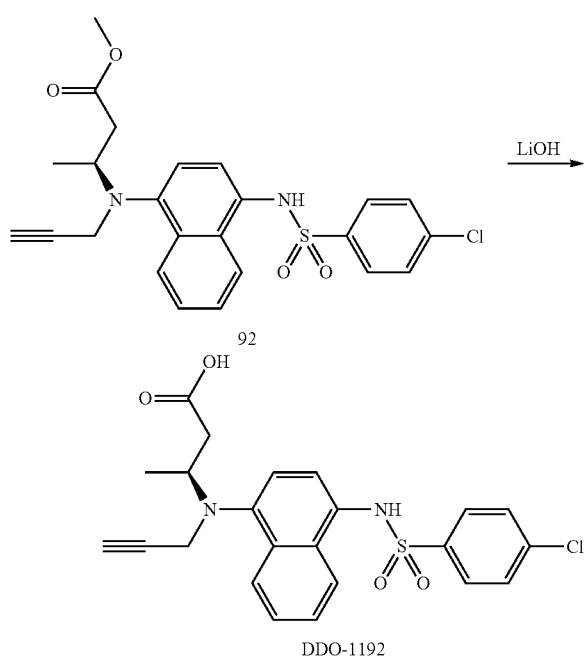

In the same way as the synthesis method of compound DDO-1160, reaction is performed on compound 92 (0.10 g, 0.21 mmol) and 2M aqueous LiOH (1.00 mL, 2.00 mmol) as starting materials to obtain a white solid DDO-1192 of 56.20 mg with yield of 59%; $^1$H NMR (300 MHz, DMSO-$d_6$) δ 10.31 (s, 1H), 8.20 (d, J=8.5 Hz, 1H), 8.02 (d, J=8.2 Hz, 1H), 7.81-7.60 (m, 3H), 7.52 (s, 2H), 7.33 (s, 1H), 7.08 (s, 1H), 3.98 (s, 2H), 3.75 (s, 1H), 3.03 (s, 1H), 2.56 (s, 1H), 2.41 (s, 1H), 1.33-1.12 (m, 3H); HRMS(ESI): found 457.0988. ($C_{23}H_{21}ClN_2O_4S$, $[M+H]^+$, requires 457.0911); HPLC (85:15 methanol:water with 1‰ TFA): $t_R$=10.79 min, 97.06%.

Synthesis of (S)-3-((4-((N-(Carboxymethyl)-4-chlorophenyl) sulfonamido) naphthalen-1-yl)(prop-2-yn-1-yl) amino) butanoic acid (DDO-1193)

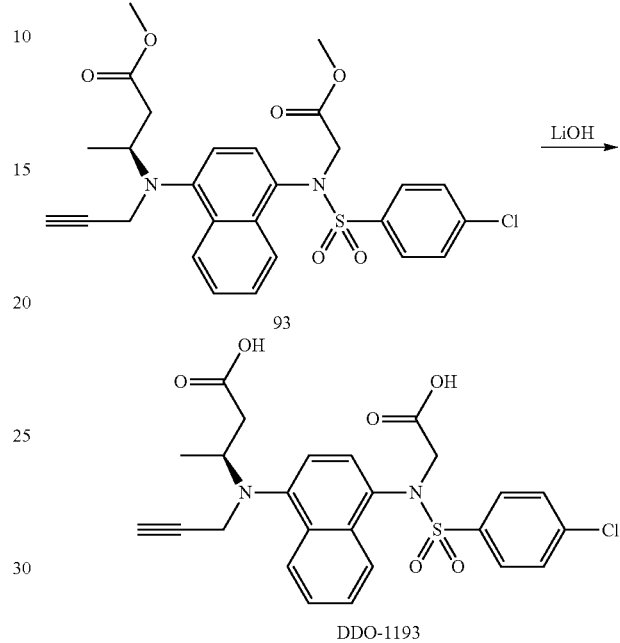

In the same way as the synthesis method of compound DDO-1161, reaction is performed on compound 93 (64.20 mg, 0.12 mmol) and 2M aqueous LiOH (1.50 mL, 3.00 mmol) as starting materials to obtain a white solid DDO-1193 of 46.30 mg with yield of 75%; $^1$H NMR (300 MHz, DMSO-$d_6$) δ 12.58 (s, 2H), 8.16 (d, J=8.1 Hz, 1H), 8.05 (d, J=8.0 Hz, 1H), 7.67 (d, J=17.4 Hz, 3H), 7.54 (dd, J=15.0, 7.7 Hz, 3H), 7.27 (d, J=7.9 Hz, 1H), 7.14 (d, J=8.0 Hz, 1H), 4.53 (d, J=17.9 Hz, 1H), 4.36 (d, J=18.1 Hz, 1H), 3.98 (s, 2H), 3.75 (s, 1H), 3.02 (s, 1H), 2.59 (s, 1H), 2.41 (s, 1H), 1.20 (s, 3H); HRMS(ESI): found 515.1044. ($C_{25}H_{23}ClN_2O_6S$, $[M+H]^+$, requires 515.0965); HPLC (85:15 methanol:water with 1‰ TFA): $t_R$=10.64 min, 95.08%.

Synthesis of (S)-methyl 3-(4-((4-methylphenyl) sulfonamido) naphthalen-1-yl) (prop-2-yn-1-yl) amino) butanoate (94)

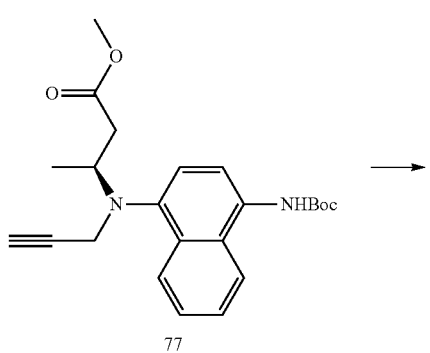

-continued

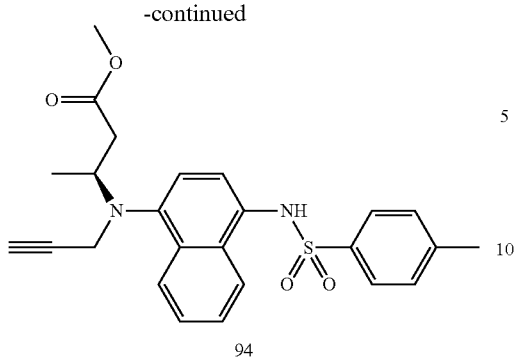

94

In the same way as the synthesis method of compound 48, after BOC removal, compound 77 (0.28 g, 0.71 mmol) reacts with 4-methoxybenzenesulfonyl chloride (0.13 g, 0.85 mmol) and pyridine (0.17 g, 2.13 mmol) to obtain a white solid 94 of 0.24 g with a yield of 75%; $^1$H NMR (300 MHz, Chloroform-d) δ 8.27-8.16 (m, 1H), 7.82 (d, J=8.3 Hz, 1H), 7.62 (dd, J=8.4, 2.3 Hz, 2H), 7.48-7.33 (m, 3H), 7.31 (m, 1H), 7.1.6 (dd, J=8.3, 2.4 Hz, 2H), 6.87-6.79 (m, 1H), 4.00 (d, J=8.6 Hz, 1H), 3.95-3.81 (m, 2H), 3.58 (d, J=2.3 Hz, 3H), 2.71-2.59 (m, 1H), 2.40 (dd, J=8.7, 2.3 Hz, 1H), 2.35 (d, J=2.3 Hz, 3H), 2.18 (q, J=2.3 Hz, 1H), 1.31 (dd, J=6.5, 2.3 Hz, 3H); ESI-MS m/z: 451.2 [M+H]$^+$.

Synthesis of (S)-methyl 3-((4-((N-(2-methoxy-2-oxoethyl)-4-methylphenyl) sulfonamido) naphthalen-1-yl)(prop-2-yn-1-yl) aminomethyl) butanoate (95)

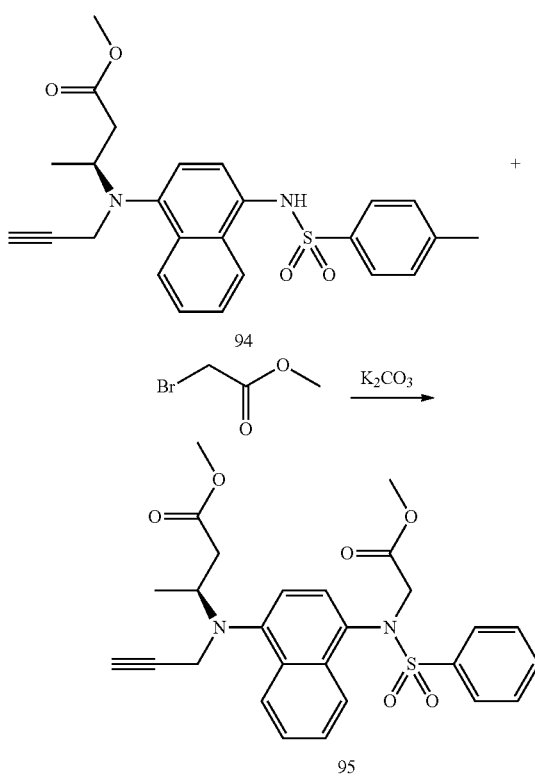

In the same way as the synthesis method of compound 49, reaction is performed on compound 94 (0.10 g, 0.22 mmol), methyl bromoacetate (40.39 mg, 0.26 mmol) and K$_2$CO$_3$ (91.08 mg, 0.66 mmol) as starting materials to obtain a pale yellow solid 95 of 60.16 mg with yield of 52%; ESI-MS m/z: 523.2 [M+H]$^+$.

Synthesis of (S)-3-((4-((4-methylphenyl) sulfonamido) naphthalen-1-yl)(prop-2-yn-1-yl) amino) butanoic acid (DDO-1194)

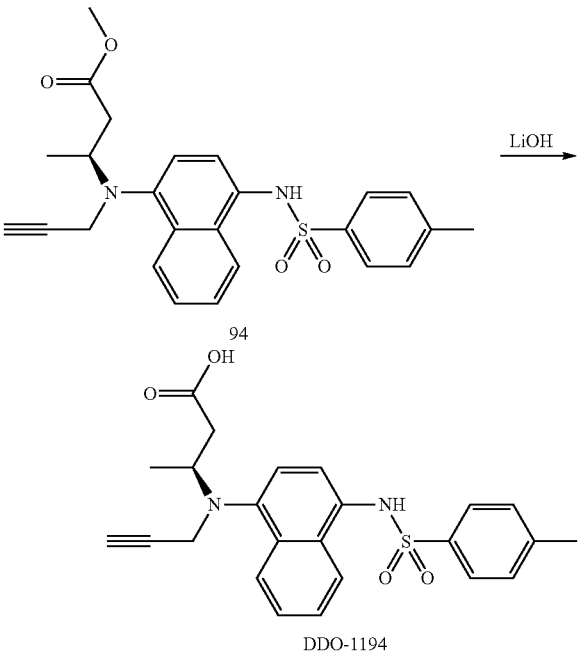

In the same way as the synthesis method of compound DDO-1160, reaction is performed on compound 94 (0.10 g, 0.22 mmol) and 2M aqueous LiOH (1.00 mL, 2.00 mmol) as starting materials to obtain a white solid DDO-1194 of 50.30 mg with yield of 53%; $^1$H NMR (300 Hz, DMSO-d$_6$) δ 12.21 (s, 1H), 10.04 (s, 1H), 8.14 (d, J=8.7 Hz, 1H), 8.01 (d, J=8.2 Hz, 1H), 7.57 (d, J=7.9 Hz, 2H), 7.47 (q, J=8.7, 7.9 Hz, 2H), 7.28 (t, J=9.9 Hz, 3H), 7.02 (d, J=7.9 Hz, 1H), 3.91 (d, J=9.2 Hz, 2H), 3.68 (s, 1H), 2.96 (s, 1H), 2.56 (s, 1H), 2.37 (s, 1H), 2.33 (s, 3H), 1.17 (d, J=6.4 Hz, 3H); HRMS (ESI): found 437.1533. (C$_{24}$H$_{24}$N$_2$O$_4$S, [M+H]$^+$, requires 437.1457); HPLC (85:15 methanol:water with 1‰ TFA): t$_R$=9.21 min, 100.00%.

Synthesis of (S)-3-((4-((N-(Carboxymethyl)-4-methylphenyl) sulfonamide) naphthalen-1-yl)(prop-2-yn-1-yl) amino) butanoic acid (DDO-1195)

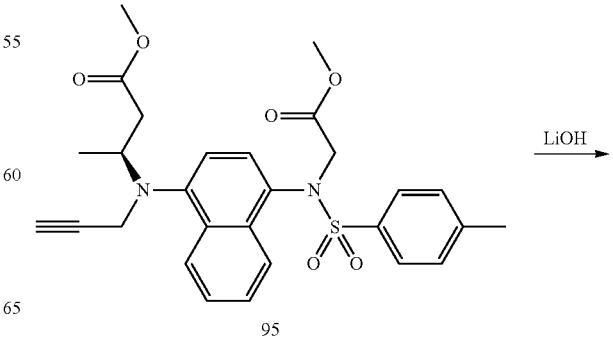

95

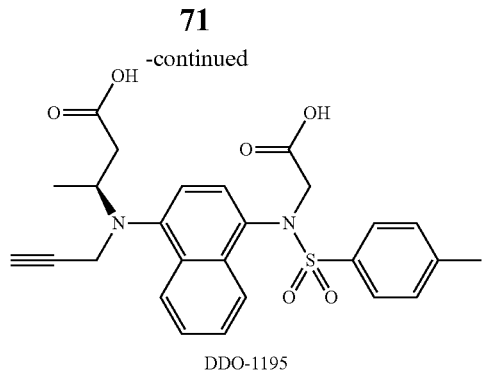

DDO-1195

In the same way as the synthesis method of compound DDO-1161, reaction is performed on compound 95 (60.16 mg, 0.11 mmol) and 2M aqueous LiOH (1.00 mL, 2.00 mmol) as starting materials to obtain a white solid DDO-1195 of 42.30 mg with yield of 77%; $^1$H NMR (300 MHz, DMSO-d$_6$) δ 12.52 (s, 2H), 8.14 (dd, J=15.6, 7.8 Hz, 2H), 7.52 (m, J=8.2 Hz, 4H), 7.36 (d, J=8.0 Hz, 2H), 7.26 (d, J=8.1 Hz, 1H), 7.12 (d, J=8.0 Hz, 1H), 4.47 (d, J=17.8 Hz, 1H), 4.34 (d, J=18.0 Hz, 1H), 3.97 (s, 2H), 3.75 (s, 1H), 3.01 (s, 1H), 2.59 (s, 1H), 2.44 (s, 1H), 2.40 (s, 3H), 1.20 (s, 3H); HRMS(ESI): found 495.1587. (C$_{26}$H$_{26}$N$_2$O$_6$S, [M+H]$^+$, requires 495.1512); HPLC (85:15 methanol:water with 1‰ TFA): t$_R$=9.11 min, 100.00%.

Synthesis of (S)-methyl 3-((4-((4-isopropylphenyl) sulfonamido) naphthalen-1-yl) (prop-2-yn-1-yl) amino) butanoate (96)

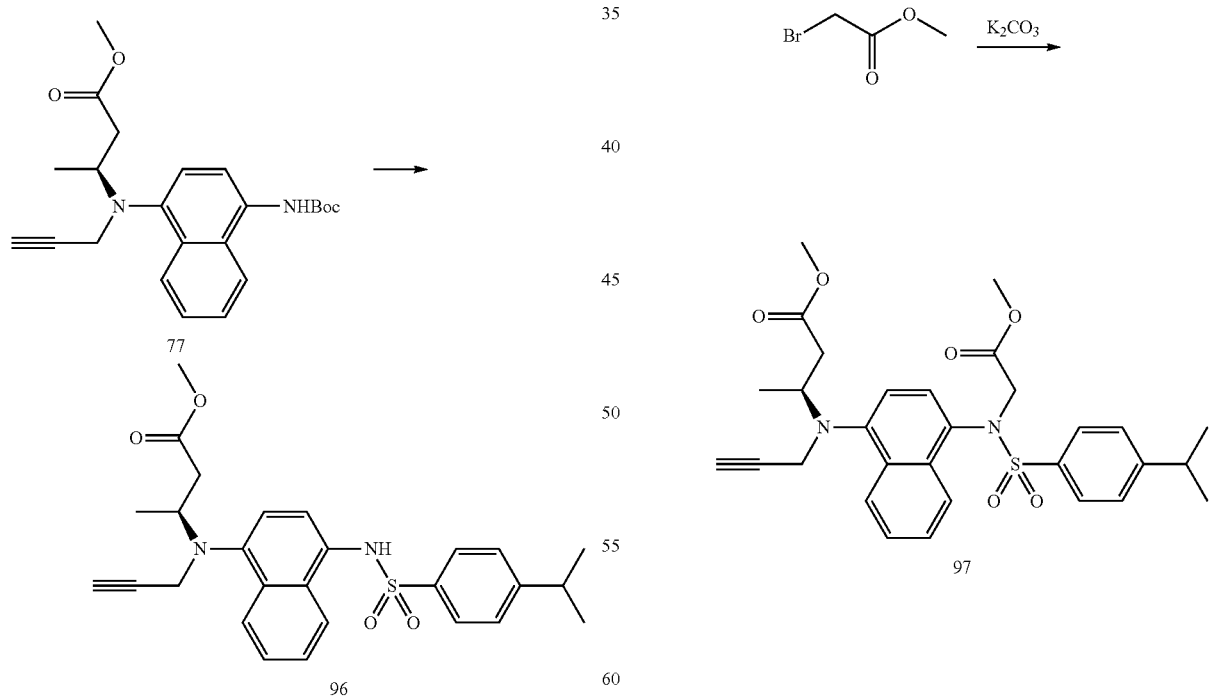

In the same way as the synthesis method of compound 48, after BOC removal, compound 77 (0.28 g, 0.71 mmol) reacts with 4-methoxybenzenesulfonyl chloride (0.18 g, 0.85 mmol) and pyridine (0.18 g, 2.13 mmol) to obtain a white solid 96 of 0.24 g with a yield of 70%; $^1$H NMR (300 MHz, Chloroform-d) δ 8.20 (d, J=8.4 Hz, 1H), 7.72 (d, J=8.3 Hz, 1H), 7.62 (d, J=8.4 Hz, 2H), 7.46-7.31 (m, 4H), 7.22-7.14 (m, 2H), 6.82 (s, 1H), 4.00 (t, J=6.4 Hz, 1H), 3.93-3.78 (m, 2H), 3.58 (s, 3H), 2.89 (p, J=7.0 Hz, 1H), 2.64 (dd, J=14.9, 4.7 Hz, 1H), 2.44-2.34 (m, 1H), 2.18 (d, J=2.5 Hz, 1H), 1.31 (d, J=6.4 Hz, 3H), 1.19 (d, J=6.9 Hz, 6H); ESI-MS m/z: 479.2 [M+H]$^+$.

Synthesis of (S)-methyl 3-((4-((4-isopropyl-N-(2-methoxy-2-oxoethyl) phenyl) sulfonamido) naphthalen-1-yl)(prop-2-yn-1-yl) aminomethyl) butanoate (97)

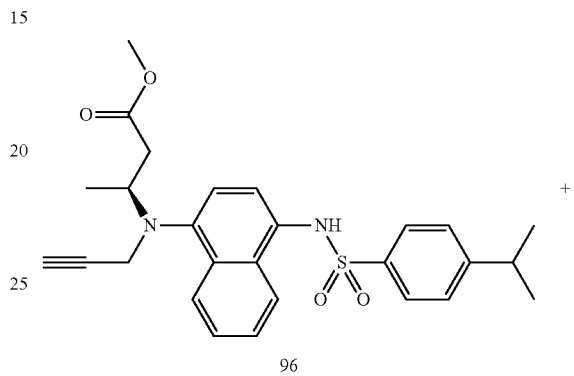

In the same way as the synthesis method of compound 49, reaction is performed on compound 96 (0.10 g, 0.21 mmol), methyl bromoacetate (38.56 mg. 0.25 mmol) and K$_2$CO$_3$ (86.94 mg, 0.63 mmol) as starting materials to obtain a pale yellow solid 97 of 60.40 mg with yield of 52%; ESI-MS m/z: 551.2 [M+H]$^+$.

Synthesis of (S)-3-((4-((4-isopropylphenyl) sulfonamido) naphthalen-1-yl)(prop-2-yn-1-yl) amino) butanoic acid (DDO-1196)

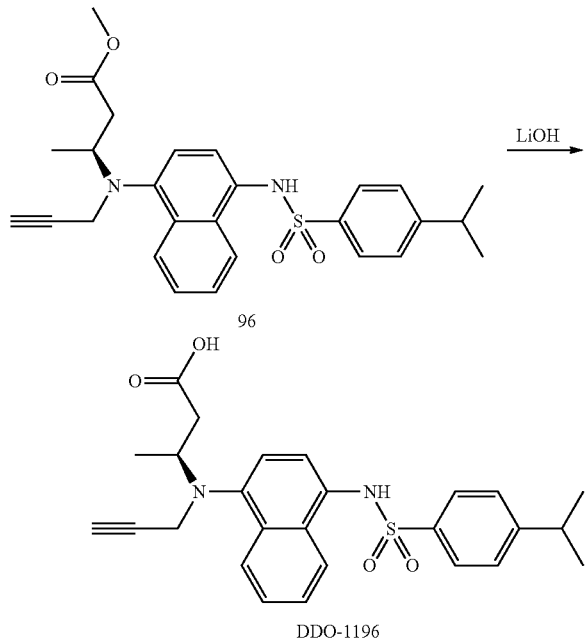

In the same way as the synthesis method of compound DDO-1160, reaction is performed on compound 96 (0.10 mg, 0.21 mmol) and 2M aqueous LiOH (1.00 mL, 2.00 mmol) as starting materials to obtain a white solid DDO-1196 of 52.80 mg with yield of 54%; $^1$H NMR (300 MHz, DMSO-$d_6$) δ 12.23 (s, 1H), 10.03 (s, 1H), 8.14 (d, J=8.4 Hz, 1H), 7.91 (d, J=8.4 Hz, 1H), 7.57 (d, J=8.0 Hz, 2H), 7.45 (d, J=7.9 Hz, 1H), 7.36 (dd, J=11.9, 7.9 Hz, 3H), 7.28 (d, J=8.0 Hz, 1H), 7.08 (d, J=8.0 Hz, 1H), 4.01-3.84 (m, 2H), 3.69 (s, 1H), 2.95 (d, J=8.6 Hz, 1H), 2.90 (d, J=6.9 Hz, 1H), 2.57 (d, J=4.0 Hz, 1H), 2.37-2.29 (m, 1H), 1.16 (d, J=6.8 Hz, 9H); HRMS(ESI): found 465.1846. ($C_{26}H_{28}N_2O_4S$, [M+H]$^+$, requires 465.1770); HPLC (85:15 methanol:water with 1% TEA): $t_R$=10.02 min, 100.00%.

Synthesis of (S)-3-((4-((N-(carboxymethyl)-4-isopropylphenyl) sulfonamido) naphthalen-1-yl)(prop-2-yn-1-yl) amino) butanoic acid (DDO-1197)

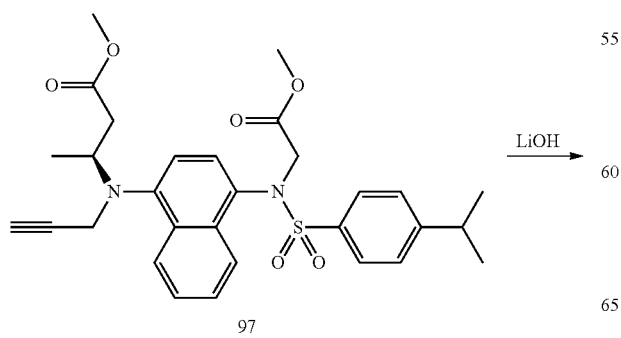

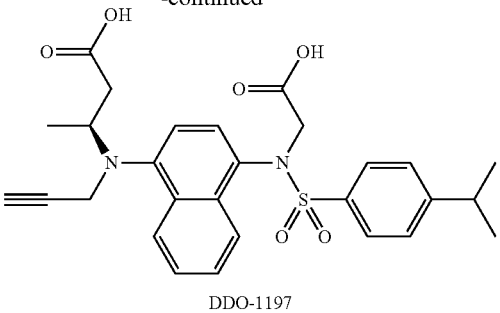

In the same way as the synthesis method of compound DDO-1161, reaction is performed on compound 97 (60.40 mg, 0.11 mmol) and 2M aqueous LiOH (1.00 mL, 2.00 mmol) as starting materials to obtain a white solid DDO-1197 of 46.30 mg with yield of 80%; $^1$H NMR (300 MHz, DMSO-$d_6$) δ 8.05 (s, 1H), 7.93 (s, 1H), 7.47 (s, 2H), 7.44-7.20 (m, 4H), 7.13 (d, J=8.8 Hz, 2H), 4.23 (d, J=13.8 Hz, 1H), 3.99 (d, J=16.0 Hz, 1H), 3.85 (s, 2H), 3.65 (s, 1H), 2.88 (s, 1H), 2.77 (s, 1H), 2.61 (s, 1H), 2.30 (d, J=13.6 Hz, 1H), 1.22-0.87 (m, 9H), HRMS(ESI): found 523.1903. ($C_{28}H_{30}N_2O_6S$, [M+H]$^+$, requires 523.1825); HPLC (85:15 methanol:water with 1‰ TFA): $t_R$=9.91 min, 99.49%.

Synthesis of methyl ((S)-3-((4-((2-methoxyphenyl) sulfonamido) naphthalen-1-yl) (prop-2-yn-1-yl) amino) butanoate (98)

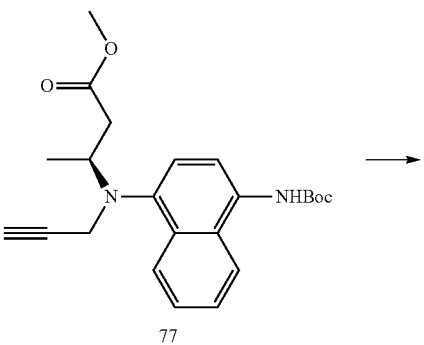

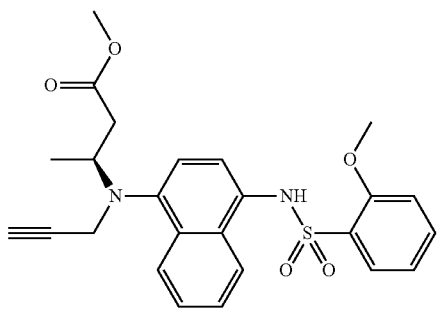

In the same way as the synthesis method of compound 48, after BOC removal, compound 77 (0.27 g, 0.68 mmol) reacts with 2-methoxybenzenesulfonyl chloride (0.17 g, 0.82 mmol) and pyridine (0.16 g, 2.04 mmol) to obtain a white solid 98 of 0.22 g with a yield of 69%, $^1$H NMR (300 MHz, Chloroform-d) δ 8.19 (d, J=8.3 Hz, 1H, 2H), 7.81 (s, 1H), 7.52 (t, J=8.5 Hz, 3H), 7.19 (m, J=8.2, 6.8 Hz, 4H), 7.02 (s, 2H), 4.10 (m, 1H), 4.03 (s, 3H), 3.97-3.81 (m, 2H), 3.56 (s, 3H), 2.61 (s, 1H), 2.37 (dd, J=14.9, 8.5 Hz, 1H), 2.17 (d, J=2.4 Hz, 1H), 1.30 (s, 3H); ESI-MS m/z: 467.2 [M+H]$^+$.

Synthesis of (S)-methyl 3-((4-((2-methoxy-N-(2-methoxy-2-oxoethyl) phenyl) sulfonamido) naphthalen-1-yl)(prop-2-yn-1-yl) amino methyl) butanoate (99)

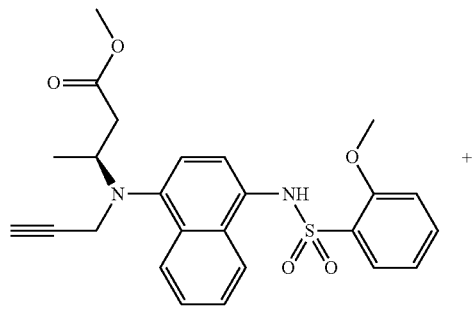

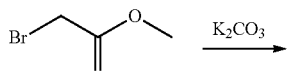

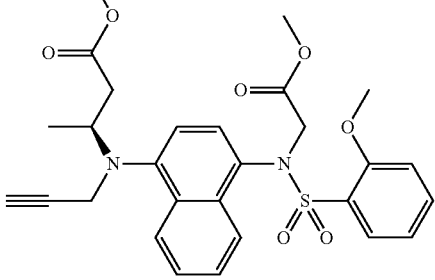

In the same way as the synthesis method of compound 49, reaction is performed on compound 98 (0.10 g, 0.21 mmol), methyl bromoacetate (38.56 mg, 0.25 mmol) and K$_2$CO$_3$ (86.94 mg, 0.63 mmol) as starting materials to obtain a pale yellow solid 99 of 70.26 mg with yield of 62%; ESI-MS m/z: 539.2 [M+H]$^+$.

Synthesis of (S)-3-((4-((4-acetamidophenyl) sulfonamido) naphthalen-1-yl) (prop-2-yn-1-yl) amino) butanoic acid (DDO-1198)

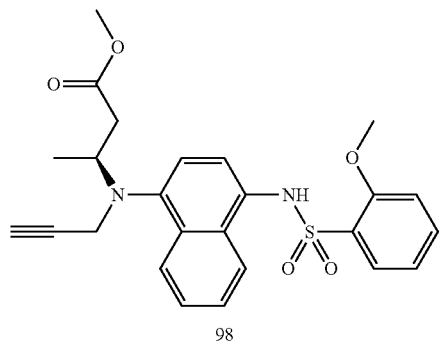

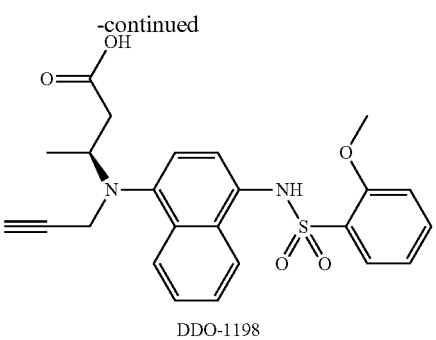

DDO-1198

In the same way as the synthesis method of compound DDO-1160, reaction is performed on compound 98 (0.10 mg, 0.21 mmol) and 2M aqueous LiOH (1.00 mL, 2.00 mmol) as starting materials to obtain a white solid DDO-1198 of 60.20 mg with yield of 63%; $^1$H NMR (300 MHz, DMSO-d$_6$) δ 9.87 (d, J=3.4 Hz, 1H), 8.12 (d, J=8.4 Hz, 2H), 7.63-7.43 (m, 4H), 7.27 (d, J=8.4 Hz, 1H), 7.14 (s, 2H), 6.94 (d, J=8.7 Hz, 1H), 3.91 (d, J=9.8 Hz, 2H), 3.75 (d, J=3.4 Hz, 3H), 3.68 (s, 1H), 2.95 (s, 1H), 2.51 (s, 1H), 2.33 (t, J=12.1 Hz, 1H), 1.16 (d, J=6.3 Hz, 3H), HRMS(ESI): found 453.1486. (C$_{24}$H$_{24}$N$_2$O$_5$S, [M+H]$^+$, requires 453.1406); HPLC (85:15 methanol:water with 1‰ TFA): t$_R$=8.67 min, 96.78%.

Synthesis of (S)-3-((4-((N-(Carboxy)-2-methoxyphenyl) sulfonamido) naphthalen-1-yl) (prop-2-yn-1-yl) amino) butanoic acid (DDO-1199)

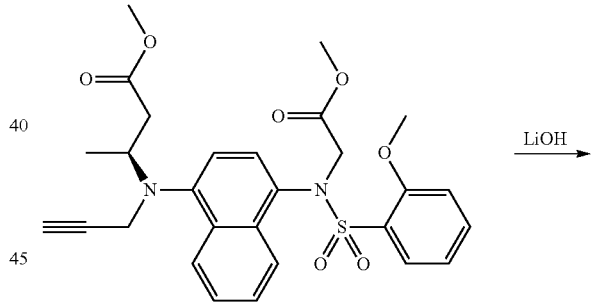

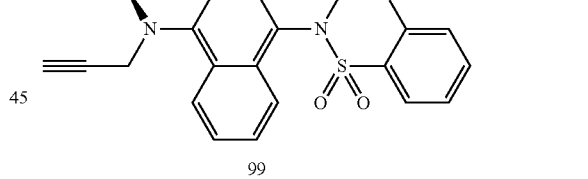

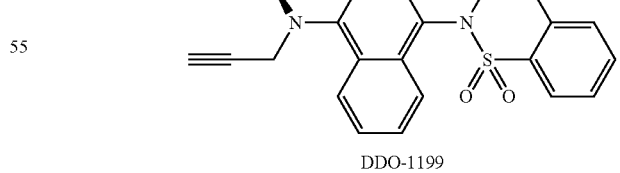

DDO-1199

In the same way as the synthesis method of compound DDO-1161, reaction is performed on compound 99 (70.26 mg, 0.13 mmol) and 2M aqueous LiOH (1.50 mL, 3.00 mmol) as starting materials to obtain a white solid DDO-1199 of 50.30 mg with yield of 75%; $^1$H NMR (300 MHz, DMSO-d$_6$) δ 8.12 (d, J=8.0 Hz, 1H), 8.01 (dd, J=8.6, 4.7 Hz, 1H), 7.57 (t, J=7.9 Hz, 1H), 7.46-7.38 (m, 3H), 7.26 (d, J=6.6 Hz, 2H), 6.89 (t, J=7.6 Hz, 1H), 4.67 (d, J=18.4 Hz, 1H), 4.40 (dd, J=18.0, 7.5 Hz, 1H), 4.05-3.94 (m, 2H), 3.90 (d, J=9.8 Hz, 3H), 3.73 (s, 1H), 2.95 (s, 1H), 2.57 (s, 1H), 2.43-2.32 (m, 1H), 1.16 (dt, J=7.0, 3.6 Hz, 3H); HRMS (ESI): found 511.1534. ($C_{26}H_{26}N_2O_7S$, [M+H]$^+$, requires 511.1561); HPLC (85:15 methanol:water with 1‰ TFA): $t_R$=8.59 min, 100.00%.

Synthesis of methyl ((S)-3-((4-((3-methoxyphenyl) sulfonamido) naphthalen-1-yl) (prop-2-yn-1-yl) amino) butanoate (100)

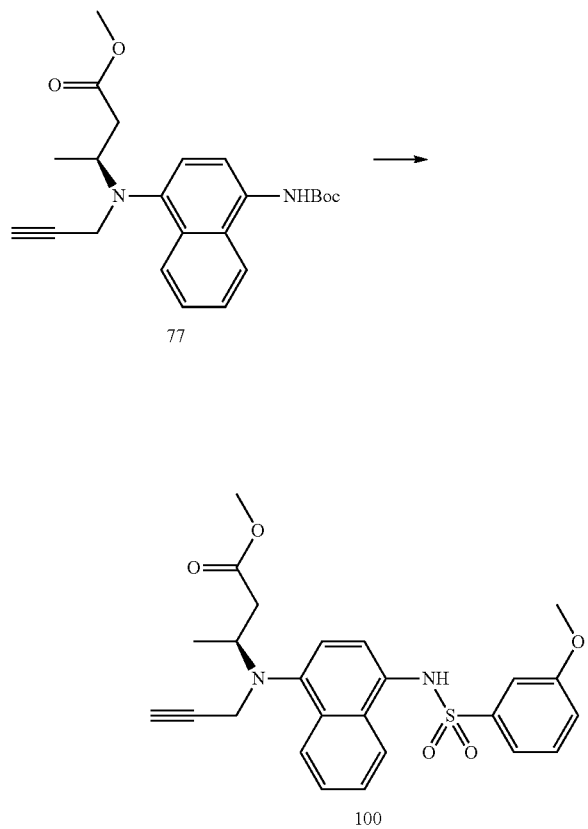

In the same way as the synthesis method of compound 48, after BOC removal, compound 77 (0.27 g, 0.68 mmol) reacts with 3-methoxybenzene sulfonyl chloride (0.17 g, 0.82 mmol) and pyridine (0.16 g, 2.04 mmol) to obtain a white solid 100 of 0.22 g with a yield of 69%; $^1$H NMR (300 MHz, Chloroform-d) δ 8.25 (d, J=8.3 Hz, 1H), 7.82 (d, J=8.2 Hz, 1H), 7.49 (d, J=7.8 Hz, 1H), 7.41 (dd, J=8.0, 3.4 Hz, 3H), 7.35-7.28 (m, 3H), 7.15 (d, J=4.0 Hz, 1H), 7.07-7.03 (m, 1H), 6.91 (s, 1H), 4.05 (q, J=5.6, 4.8 Hz, 1H), 3.99-3.89 (m, 1H), 3.68 (s, 1H), 3.64 (s, 3H), 3.62 (s, 3H), 2.67 (dd, J=15.0, 4.7 Hz, 1H), 2.42 (dd, J=15.0, 8.6 Hz, 1H), 2.22 (s, 1H), 1.30 (d, J=9.2 Hz, 3H); ESI-MS m/z: 466.2 [M+H]$^+$.

Synthesis of (S)-methyl 3-((4-((3-methoxy-N-(2-methoxy-2-oxoethyl) phenyl) sulfonamido) naphthalen-1-yl)(prop-2-yn-1-yl) aminomethyl) butanoate (101)

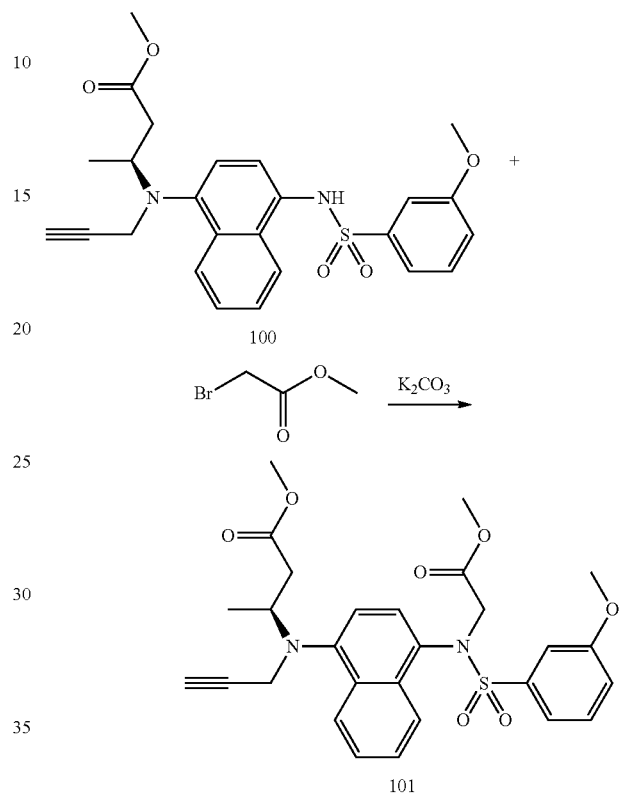

In the same way as the synthesis method of compound 49, reaction is performed on compound 100 (0.10 g, 0.21 mmol), methyl bromoacetate (38.56 mg, 0.25 mmol) and K$_2$CO$_3$ (86.94 mg, 0.63 mmol) as starting materials to obtain a pale yellow solid 101 of 70.26 mg with yield of 62%; ESI-MS m/z: 539.2 [M+H]$^+$.

Synthesis of (S)-3-((4-((3-methoxyphenyl) sulfonamido) naphthalen-1-yl)(prop-2-yn-1-yl) amino) butanoic acid (DDO-1200)

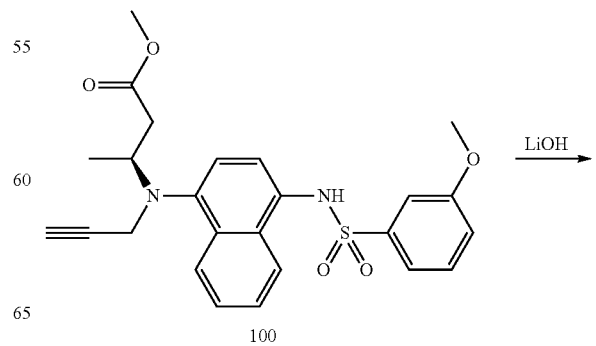

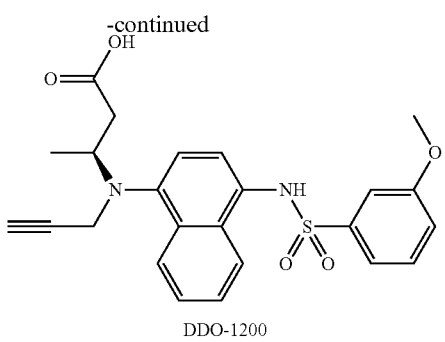

DDO-1200

In the same way as the synthesis method of compound DDO-1160, reaction is performed on compound 100 (0.10 mg, 0.21 mmol) and 2M aqueous LiOH (1.00 mL, 2.00 mmol) as starting materials to obtain a white solid DDO-1200 of 60.20 mg with yield of 63%; $^1$H NMR (300 MHz, DMSO-d$_6$) δ 9.87 (d, J=3.4 Hz, 1H), 8.12 (d, J=8.4 Hz, 2H), 7.63-7.43 (m, 4H), 7.27 (d, J=8.4 Hz, 1H), 7.14 (s, 2H), 6.94 (d, J=8.7 Hz, 1H), 3.91 (d, J=9.8 Hz, 2H), 3.75 (d, J=3.4 Hz, 3H), 3.68 (s, 1H), 2.95 (s, 1H), 2.51 (s, 1H), 2.33 (t, J=12.1 Hz, 1H), 1.16 (d, J=6.3 Hz, 3H); HRMS(ESI): found 453.1486. (C$_{24}$H$_{24}$N$_2$O$_5$S, [M+H]$^+$, requires 453.1406); HPLC (85:15 methanol:water with 1‰ TFA): 9.63 min, 95.03%.

Synthesis of (S)-3-((4-((N-(Carboxy)-3-methoxyphenyl) sulfonamido) naphthalen-1-yl) (prop-2-yn-1-yl) amino) butanoic acid (DDO-1201)

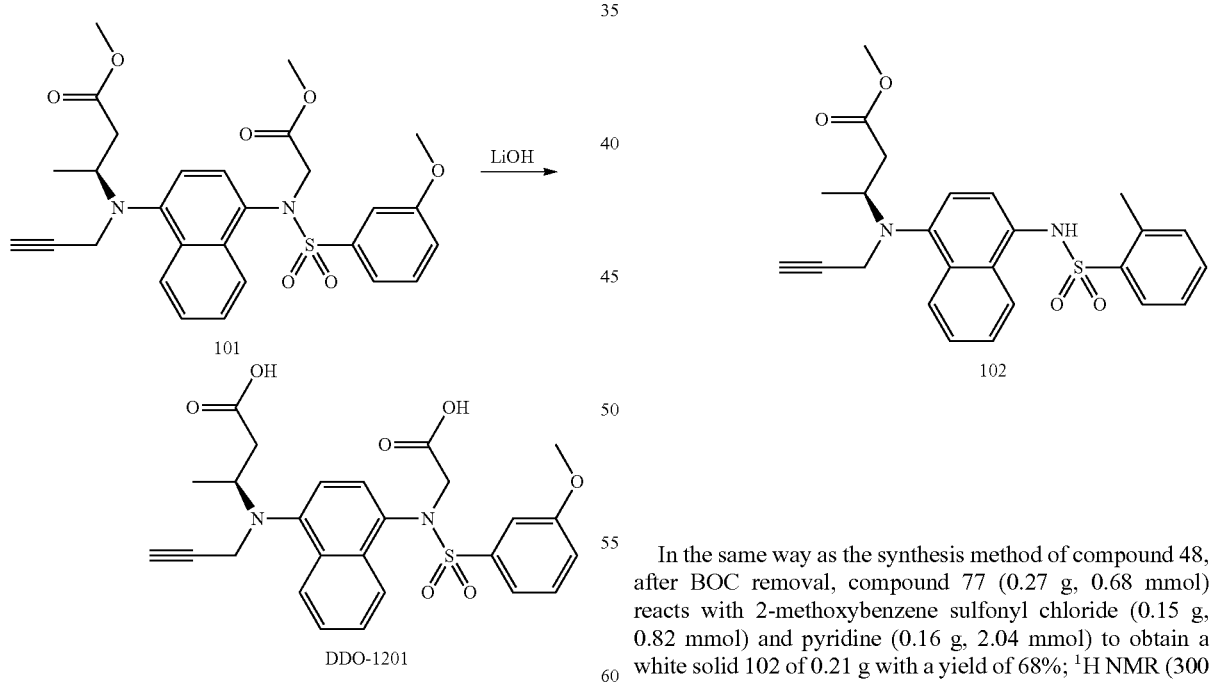

DDO-1201

In the same way as the synthesis method of compound DDO-1161, reaction is performed on compound 101 (70.26 mg, 0.13 mmol) and 2M aqueous LiOH (1.50 mL, 3.00 mmol) as starting materials to obtain a while solid DDO-1201 of 50.30 mg with yield of 75%; $^1$H NMR (300 MHz, DMSO-d$_6$) δ 8.38 (dd, J=7.5, 1.5 Hz, 1H), 8.04 (dd, J=7.4, 1.6 Hz, 1H), 7.66 (ddd, J=8.5, 5.2, 1.7 Hz, 2H), 7.57-7.46 (m, 3H), 7.13 (dt, J=7.5, 2.0 Hz, 1H), 6.86 (d, J=7.5 Hz, 1H), 6.59 (d, J=7.5 Hz, 1H), 4.52 (d, J=12.3 Hz, 1H), 4.35 (d, J=12.5 Hz, 1H), 4.14 (dd, J=12.4, 3.0 Hz, 1H), 4.07 (dd, J=12.4, 3.0 Hz, 1H), 3.81 (s, 3H), 3.68 (s, 1H), 2.95 (dd, J=12.5, 6.9 Hz, 1H), 2.83 (t, J=3.0 Hz, 1H), 2.74 (dd, J=12.4, 7.0 Hz, 1H), 1.23 (d, J=6.8 Hz, 3H). HRMS(ESI): found 511.1534. (C$_{26}$H$_{26}$N$_2$O$_7$S [M+H]$^+$, requires 511.1461); HPLC (85:15 methanol:water with 1‰ TFA): t$_R$=8.84 min, 99.04%.

Synthesis of (S)-methyl 3-((4-((2-methylphenyl) sulfonamide) naphthalen-1-yl) (prop-2-yn-1-yl) amino) butanoate (102)

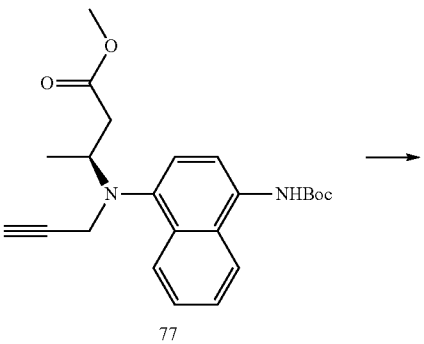

In the same way as the synthesis method of compound 48, after BOC removal, compound 77 (0.27 g, 0.68 mmol) reacts with 2-methoxybenzene sulfonyl chloride (0.15 g, 0.82 mmol) and pyridine (0.16 g, 2.04 mmol) to obtain a white solid 102 of 0.21 g with a yield of 68%; $^1$H NMR (300 MHz, Chloroform-d) δ 8.27-8.21 (m, 1H), 7.93 (dd, J=8.2, 1.5 Hz, 2H), 7.49 (ddd, J=7.0, 4.3, 1.7 Hz, 2H), 7.42 (dd, J=7.5, 1.6 Hz, 1H), 7.33 (d, J=8.0 Hz, 1H), 7.24 (d, J=6.5 Hz, 2H) 7.16-7.10 (m, 1H), 6.95 (d, J=5.9 Hz, 1H), 4.00 (dt, J=7.5, 3.8 Hz, 1H), 3.96-3.86 (m, 2H), 3.59 (s, 3H), 2.63 (s, 1H), 2.58 (s, 3H), 2.45-2.37 (m, 1H), 2.18 (t, J=2.4 Hz, 1H), 1.33-1.30 (m, 3H); ESI-MS m/z: 451.2 [M+H]$^+$.

Synthesis of (S)-methyl 3-((4-((N-(2-methoxy-2-oxoethyl)-2-methylphenyl) sulfonamido) naphthalen-1-yl)(prop-2-yn-1-yl) aminomethyl) butanoate (103)

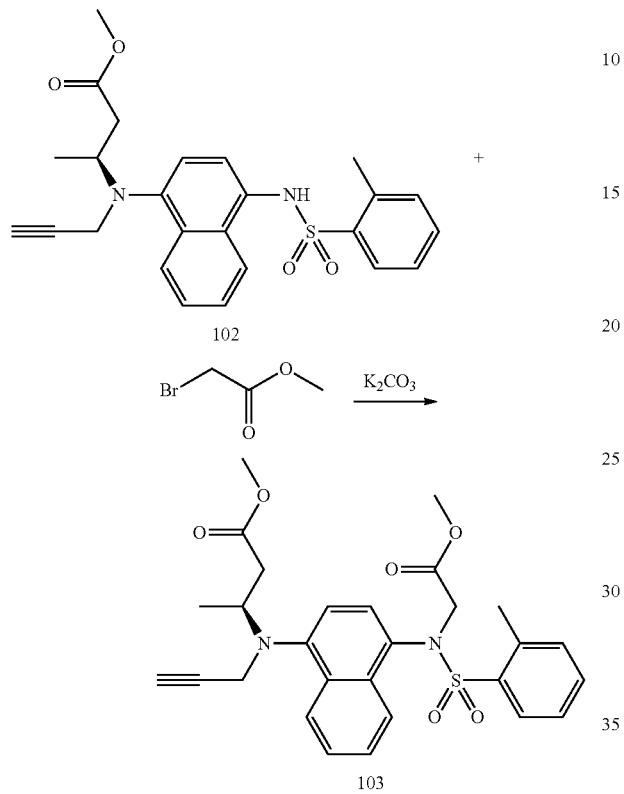

In the same way as the synthesis method of compound 49, reaction is performed on compound 102 (0.10 g, 0.22 mmol), methyl bromoacetate (40.80 mg, 0.2.6 mmol) and K₂CO₃ (91.08 mg, 0.66 mmol) as starting materials to obtain a pale yellow solid 103 of 72.26 mg with yield of 63%; ESI-MS m/z: 523.2 [M+H]⁺.

Synthesis of (S)-3-((4-((2-methylphenyl) sulfonamido) naphthalen-1-yl)(prop-2-yn-1-yl) amino) butanoic acid (DDO-1202)

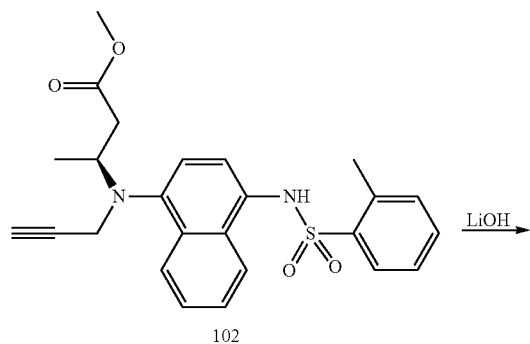

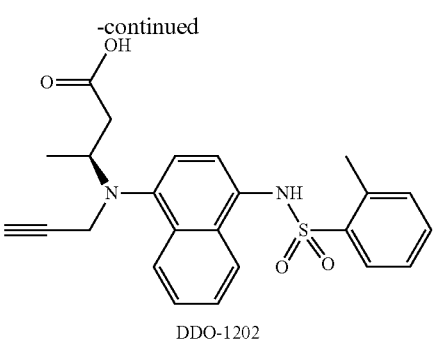

In the same way as the synthesis method of compound DDO-1160, reaction is performed on compound 102 (0.10 mg, 0.22 mmol) and 2M aqueous LiOH (1.00 mL, 2.00 mmol) as starting materials to obtain a white solid DDO-1202 of 61.30 mg with yield of 64%; ¹H NMR (300 MHz, DMSO-d₆) δ 10.07 (s, 1H), 8.15 (d, J=8.4 Hz, 1H), 8.04-7.99 (m, 1H), 7.71 (d, J=7.9 Hz, 1H), 7.46 (tt, J=11.3, 6.2 Hz, 3H), 7.32 (d, J=8.1 Hz, 1H), 7.27 (d, J=7.0 Hz, 1H), 6.99 (d, J=8.0 Hz, 1H), 3.99-3.83 (m, 2H), 3.72-3.67 (m, 1H), 2.93 (s, 1H), 2.54 (dd, J=13.8, 3.4 Hz, 1H), 2.45 (s, 3H), 2.33 (dd, J=15.0, 9.4 Hz, 1H), 1.13 (dd, J=16.2, 6.5 Hz, 3H); HRMS(ESI): found 437.1536. (C₂₄H₂₄N₂O₄S, [M+H]⁺, requires 437.1457); HPLC (85:15 methanol:water with 1‰ TFA): t_R=9.99 min, 97.94%.

Synthesis of (S)-3-((4-((N-(Carboxymethyl)-methylphenyl) sulfonamido) naphthalen-1-yl)(prop-2-yn-1-yl) amino) butanoic acid (DDO-1203)

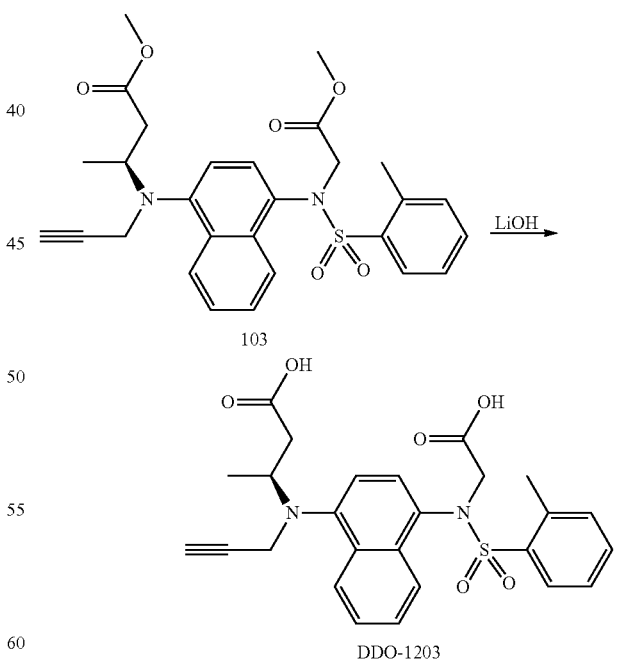

In the same way as the synthesis method of compound DDO-1161, reaction is performed on compound 103 (72.26 mg, 0.14 mmol) and 2M aqueous LiOH (1.50 mL, 3.00 mmol) as starting materials to obtain a white solid DDO-1203 of 52.80 mg with yield of 75%; ¹H NMR (300 MHz, DMSO-d$_6$) δ 8.20-8.10 (m, 1H), 7.97 (dd, J=22.9, 8.3 Hz, 1H), 7.81 (t, J=6.5 Hz, 1H), 7.47 (dt, J=14.0, 7.6 Hz, 3H), 7.41-7.33 (m, 1H), 7.24 (dd, J=9.5, 3.9 Hz, 2H), 7.04 (d, J=8.1 Hz, 1H), 4.53 (d, J=17.9 Hz 1H), 4.35 (d, J=18.1 Hz, 1H), 4.06-3.84 (m, 2H), 3.75 (s, 1H), 2.71 (s, 1H), 2.58 (dd, J=15.0, 5.0 Hz, 1H), 2.40 (td, J=9.9, 9.5, 5.0 Hz, 1H), 2.03 (d, J=8.0 Hz, 1H), 1.95 (d, J=8.4 Hz, 2H), 1.26-1.14 (m, 3H); HRMS(ESI): found 495.1594. (C$_{26}$H$_{26}$N$_2$O$_6$S, [M+H]$^+$, requires 495.1512); HPLC (85:15 methanol:water with 1% TFA): t$_R$=9.22 min, 100.00%.

Synthesis of (S)-methyl 3-((4-((2,4-dimethylphenyl) sulfonamido) naphthalen-1-yl) (prop-2-yn-1-yl) amino) butanoate (104)

In the same way as the synthesis method of compound 48, after BOC removal, compound 77 (0.27 g, 0.68 mmol) reacts with 2,4-dimethylbenzenesulfonyl chloride (0.17 g, 0.82 mmol) and pyridine (0.16 g, 2.04 mmol) to obtain a white solid 104 of 0.22 g with a yield of 69%; $^1$H NMR (300 MHz, Chloroform-d) δ 8.26-8.22 (m, 1H), 7.96 (d, J=2.6 Hz, 1H), 7.80 (d, J=4.2 Hz, 1H), 7.50 (dd, J=6.8, 2.8 Hz, 2H), 7.33 (d, J=8.0 Hz, 1H), 7.13 (d, J=8.0 Hz, 1H), 7.07 (s, 2H), 6.82 (s, 1H), 3.99 (s, 1H), 3.92 (dd, J=14.3, 7.3 Hz, 2H), 3.59 (s, 3H), 2.66 (dd, J=10.3, 4.6 Hz, 1H), 2.56 (d, J=4.1 Hz 3H), 2.44-2.40 (m, 1H), 2.36 (s, 3H), 2.19 (s, 1H), 1.31 (s, 3H); ESI-MS m/z: 465.2 [M+H]$^+$.

Synthesis of (S)-methyl 3-((4-((N-(2-methoxy-2-oxoethyl)-2,4-dimethylphenyl) sulfonamido) naphthalen-1-yl)(prop-2-yn-1-yl) amino) butanoate (105)

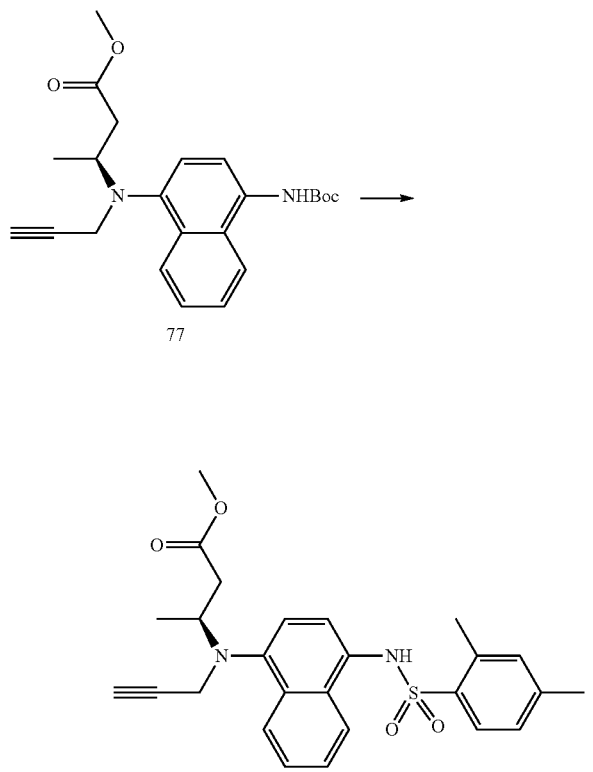

In the same way as the synthesis method of compound 49, reaction is performed on compound 104 (0.10 g, 0.21 mmol), methyl bromoacetate (38.56 mg, 0.2.5 mmol) and K$_2$CO$_3$ (86.94 mg, 0.63 mmol) as starting materials to obtain a pale yellow solid 105 of 74.06 mg with yield of 66%; ESI-MS m/z: 537.2 [M+H]$^+$.

Synthesis of (S)-3-((4-((2,4-dimethylphenyl) sulfonamido) naphthalen-1-yl) (prop-2-yn-1-yl) amino) butanoic acid (DDO-1204)

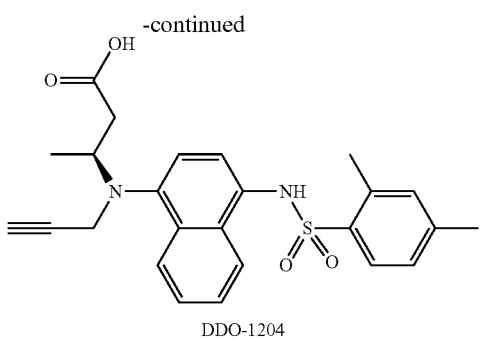

DDO-1204

In the same way as the synthesis method of compound DDO-1160, reaction is performed on compound 104 (0.10 mg, 0.21 mmol) and 2M aqueous LiOH (1.00 mL, 2.00 mmol) as starting materials to obtain a white solid DDO-1204 of 59.80 mg with yield of 63%; $^1$H NMR (300 MHz, DMSO-$d_6$) δ 10.00 (s, 1H), 8.19-8.13 (m, 1H), 8.05 (dd, J=5.9, 3.2 Hz, 1H), 7.63-7.58 (m, 1H), 7.49-7.43 (m, 2H), 7.25 (d, J=8.1 Hz, 1H), 7.15 (s, 1H), 7.09 (d, J=7.5 Hz, 1H), 6.99 (d, J=7.8 Hz, 1H), 3.99-3.84 (m, 2H), 3.71 (d, J=8.6 Hz, 1H), 2.93 (s, 1H), 2.58-2.51 (m, 1H), 2.44 (d, J=8.3 Hz, 3H), 2.36 (d, J=9.4 Hz, 1H), 2.29 (s, 3H), 1.16 (d, J=6.5 Hz, 3H); HRMS(ESI): found 451.1690. ($C_{25}H_{26}N_2O_4S$, [M+H]$^+$, requires 451.1613); HPLC (85:15 methanol:water with 1% TEA): $t_R$=9.55 min, 100.00%.

Synthesis of (S)-3-((4-((N-(Carboxy)-2,4-dimethylphenyl sulfonamido) naphthalen-1-yl) (prop-2-yn-1-yl) amino) butanoic acid (DMO-1205)

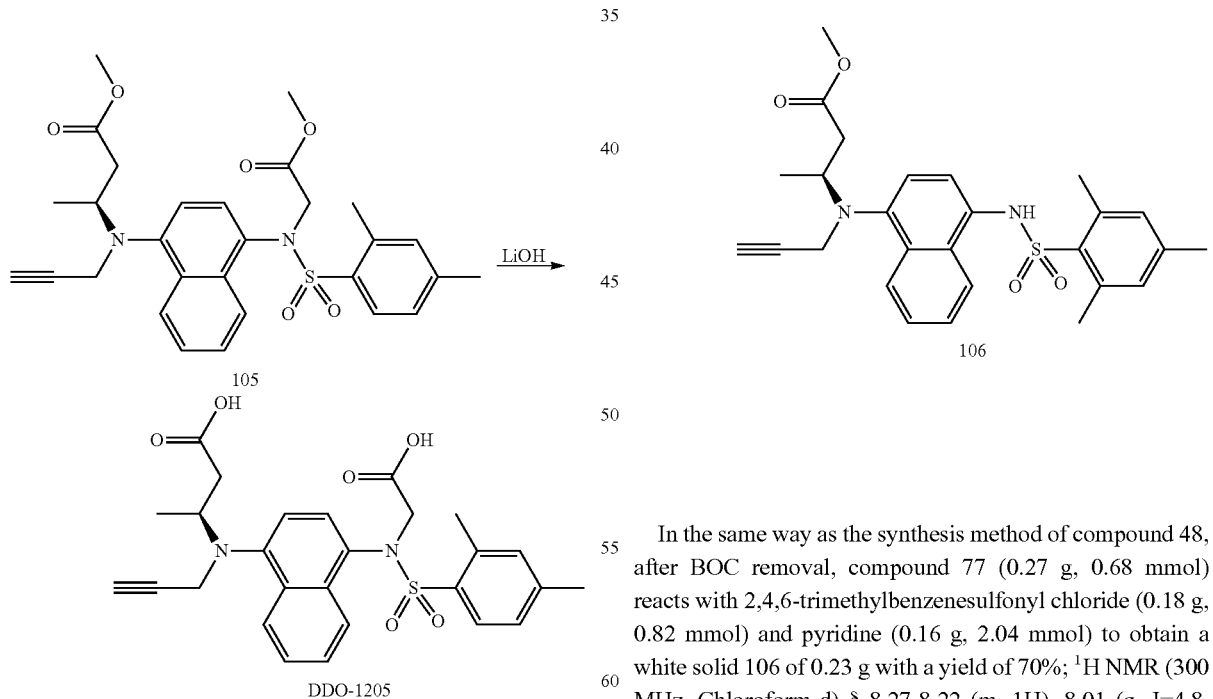

In the same way as the synthesis method of compound DDO-1161, reaction is performed on compound 105 (74.06 mg, 0.14 mmol) and 2M aqueous LiOH (1.50 mL, 3.00 mmol) as starting materials to obtain a white solid DDO-1205 of 50.20 mg with yield of 70%; $^1$H NMR (300 MHz, DMSO-$d_6$) δ 12.49 (s, 2H), 8.19-8.14 (m, 1H), 8.07 (d, J=8.2 Hz, 1H), 7.70 (d, J=8.1 Hz, 1H), 7.48 (p, J=7.1 Hz, 2H), 7.28 (d, J=8.1 Hz, 1H), 7.20 (dd, J=10.5, 6.4 Hz, 2H), 7.06 (d, J=4.5 Hz, 1H), 4.55-4.33 (m, 2H), 3.97 (s, 2H), 3.75 (s, 1H), 2.97 (s, 1H), 2.57 (d, J=15.2 Hz, 1H), 2.45-2.36 (m, 1H), 2.32 (s, 3H), 1.94 (dd, J=21.6, 8.0 Hz, 3H), 1.21 (d, J=10.7 Hz, 3H); HRMS(ESI): found 509.1744. ($C_{27}H_{28}N_2O_6S$, [M+H]$^+$, requires 509.1668); HPLC (85:15 methanol:water with 1‰ TFA): $t_R$=9.48 min, 97.95%.

Synthesis of (S)-methyl 3-(prop-2-yn-1-yl) (4-((2,4,6-trimethylphenyl) sulfonamidyl) naphthalen-1-yl) amino) butanoate (106)

In the same way as the synthesis method of compound 48, after BOC removal, compound 77 (0.27 g, 0.68 mmol) reacts with 2,4,6-trimethylbenzenesulfonyl chloride (0.18 g, 0.82 mmol) and pyridine (0.16 g, 2.04 mmol) to obtain a white solid 106 of 0.23 g with a yield of 70%; $^1$H NMR (300 MHz, Chloroform-d) δ 8.27-8.22 (m, 1H), 8.01 (q, J=4.8, 2.9 Hz, 1H), 7.49 (dt, J=8.5, 5.1 Hz, 1H), 6.98 (d, J=7.8 Hz, 1H), 6.92 (s, 2H), 6.73 (s, 1H), 4.00 (s, 1H), 3.91 (d, J=14.2 Hz, 2H), 3.60 (s, 3H), 2.68-2.62 (m, 1H), 2.49 (s, 6H), 2.44-2.37 (m, 1H), 2.31 (s, 3H), 2.17 (d, J=2.4 Hz, 1H), 1.31 (d, J=1.6 Hz, 3H); ESI-MS m/z: 479.2 [M+H]$^+$.

Synthesis of (S)-methyl 3-((4-((N-(2-methoxy-2-oxoethyl)-2,4,6-trimethylphenyl) sulfonamido) naphthalen-1-yl)(prop-2-yn-1-methyl) yl) amino) butanoate (107)

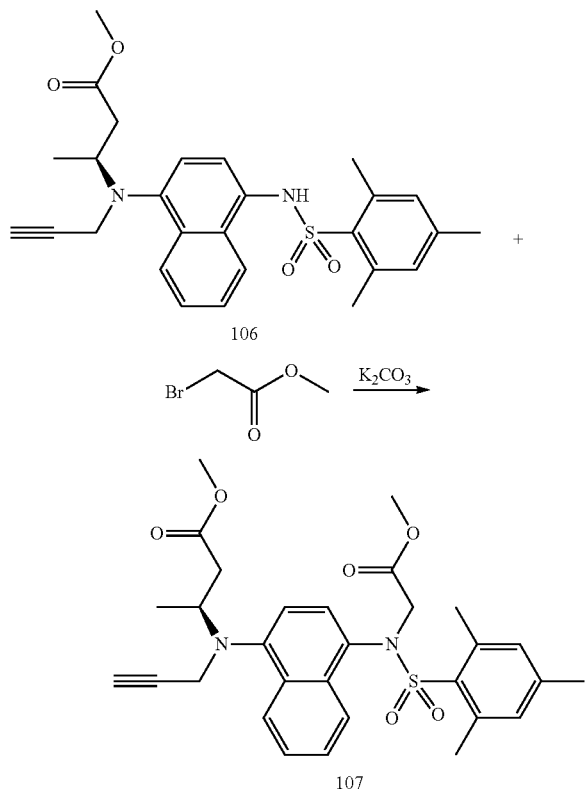

In the same way as the synthesis method of compound 49, reaction is performed on compound 106 (0.10 g, 0.21 mmol), methyl bromoacetate (38.56 mg, 0.25 mmol) and K$_2$CO$_3$ (86.94 mg, 0.63 mmol) as starting materials to obtain a pale yellow solid 107 of 70.20 mg with yield of 61%; ESI-MS m/z: 551.2 [M+H]$^+$.

Synthesis of (S)-3-(prop-2-yn-1-yl(4-((2,4,6-trimethylphenyl) sulfonamido) naphthalen-1-yl) amino) butanoic acid (DDO-1206)

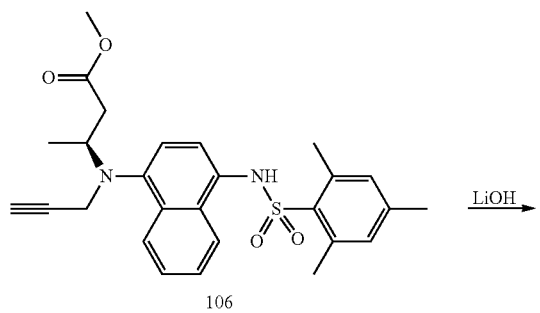

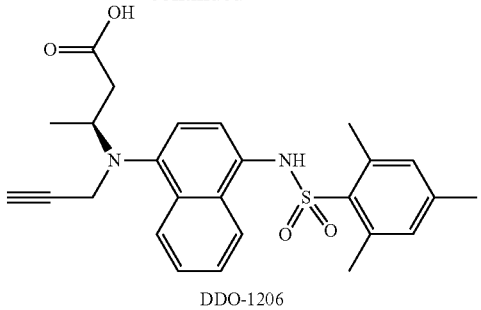

In the same way as the synthesis method of compound DDO-1161, reaction is performed on compound 106 (0.10 mg, 0.21 mmol) and 2M aqueous LiOH (1.00 mL, 2.00 mmol) as starting materials to obtain a white solid DDO-1206 of 60.20 mg with yield of 64%; $^1$H NMR (300 MHz, DMSO-d$_6$) δ 12.20 (s, 1H), 9.86 (s, 1H), 8.14 (t, J=6.9 Hz, 1H), 8.03-7.95 (m, 1H), 7.45 (td, J=8.3, 4.0 Hz, 2H), 7.24 (d, J=8.0 Hz, 1H), 6.93 (d, J=1.9 Hz, 3H), 4.04-3.85 (m, 2H), 3.69 (s, 1H), 2.92 (d, J=2.4 Hz, 1H), 2.56 (d, J=4.3 Hz, 1H), 2.47-2.37 (m, 1H), 2.31 (s, 6H), 2.22 (s, 3H), 1.16 (d, J=6.5 Hz, 3H); $^{13}$C NMR (75 MHz, DMSO-d$_6$) δ 172.82, 144.89, 141.53, 138.53, 131.48, 128.39, 125.82, 125.75, 124.07, 123.74, 123.59, 119.54, 80.93, 74.49, 54.48, 38.67, 38.49, 37.33, 22.55, 20.35, 17.00; HRMS(ESI): found 465.1848. (C$_{26}$H$_{28}$N$_2$O$_4$S, [M+H]$^+$, requires 465.1770); HPLC (85:15 methanol:water with 1% TFA): t$_R$=11.81 min, 100.00%.

Synthesis of (S)-3-((4-((N-(Carboxymethyl)-2,4,6-trimethylphenyl) sulfonamidyl) naphthalen-1-yl) (prop-2-yn-1-yl) amino) butanoic acid (DDO-1207)

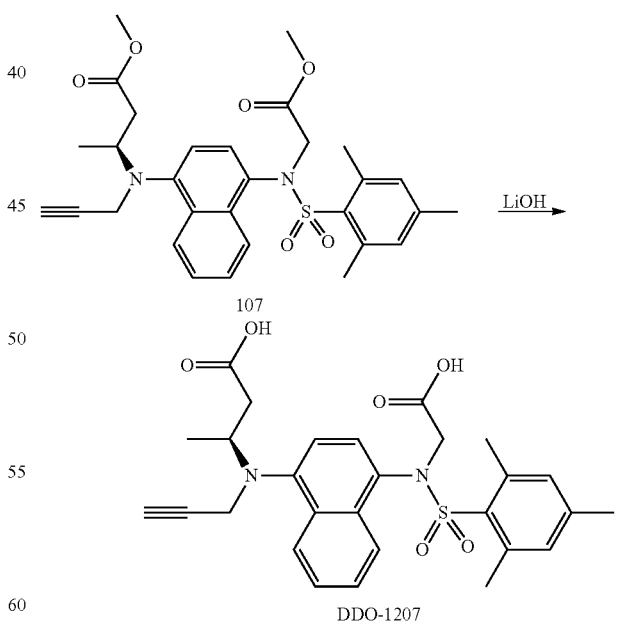

In the same way as the synthesis method of compound DDO-1161, reaction is performed on compound 107 (7.20 mg, 0.13 mmol) and 2M aqueous LiOH (1.50 mL, 3.00 mmol) as starting materials to obtain a white solid DDO-1207 of 50.10 mg with yield of 73%; $^1$H NMR (300 MHZ, DMSO-$d_6$) δ 8.13 (t, J=7.6 Hz, 1H), 7.86 (d, J=8.6 Hz, 1H), 7.52-7.41 (m, 2H), 7.38-7.25 (m, 2H), 6.85 (d, J=6.3 Hz, 2H), 4.70 (d, J=17.7 Hz, 1H), 4.38 (d, J=17.4 Hz, 1H), 3.95 (s, 2H), 3.72 (s, 1H), 2.95 (s, 1H), 2.57 (dd, J=15.3, 4.4 Hz, 1H), 2.42-2.32 (m, 1H), 2.17 (s, 3H), 2.14 (d, J=4.0 Hz, 6H), 1.25-1.13 (m, 3H), $^{13}$C NMR (75 MHz, DMSO-$d_6$) δ 172.77, 170.22, 146.84, 142.07, 139.23, 132.29, 131.57, 130.78, 129.29, 126.02, 125.73, 123.72, 123.64, 119.29, 119.15, 74.57, 54.75, 54.61, 52.89, 38.66, 38.10, 36.99, 36.82, 22.82, 20.31, 17.15, 16.67; HRMS(ESI): found 523.1897. ($C_{28}H_{30}N_2O_6S$, [M+H]$^+$, requires 523.1825); HPLC (85:15 methanol:water with 1‰ TFA): $t_R$=10.15 min, 99.20%.

Synthesis of (S)-methyl 3-(prop-2-yn-1-yl) (4-((2,3,5,6-tetramethoxyphenyl) sulfonamido) naphthalen-1-yl) amino) butanoate (108)

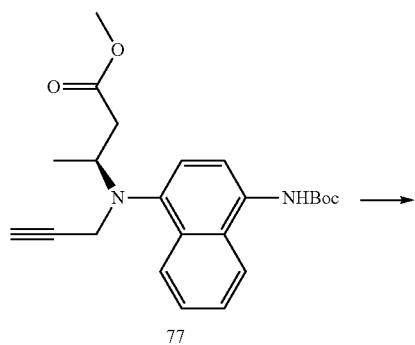

77

In the same way as the synthesis method of compound 48, after BOC removal, compound 77 (027 g, 0.68 mmol) reacts with 2,3,5,6-tetra methylbenzenesulfonyl chloride (0.19 g, 0.82 mmol) and pyridine (0.16 g, 2.04 mmol) to obtain a white solid 108 of 0.22 g with a yield of 65%; $^1$H NMR (300 MHz, Chloroform-d) δ 8.28-8.24 (m, 1H), 8.14-8.08 (m, 1H), 7.56-7.51 (m, 2H), 7.33 (s, 1H), 7.17 (s, 1H), 6.99 (d, J=8.0 Hz, 1H), 6.71 (s, 1H), 4.02 (s, 1H), 3.93 (d, J=14.4 Hz, 2H), 3.61 (s, 3H), 2.63 (d, J=4.4 Hz, 1H), 2.44 (s, 6H), 2.38 (d, J=9.1 Hz, 1H), 2.27 (s, 6H), 2.19 (d, J=2.4 Hz, 1H), 1.33 (s, 3H); ESI-MS m/z: 493.2 [M+H]$^+$.

Synthesis of (S)-methyl 3-((4-((N-(2-methoxy-2-oxoethyl)-2,3,5,6-tetramethylphenyl) sulfonamido) naphthalen-1-yl)(prop-2-yn-1-methyl) yl) amino) butanoate (109)

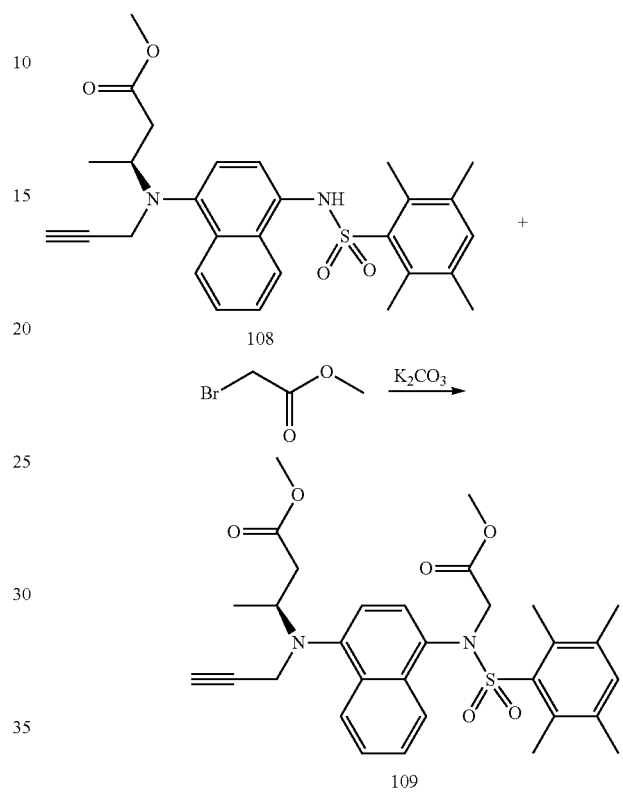

In the same way as the synthesis method of compound 49, reaction is performed on compound 108 (0.10 g, 0.20 mmol), methyl bromoacetate (36.72 mg, 0.24 mmol) and $K_2CO_3$ (82.80 mg, 0.60 mmol) as starting materials to obtain a pale yellow solid 109 of 68.20 mg with yield of 61%; ESI-MS m/z: 565.2 [M+H]$^+$.

Synthesis of (S)-3-(prop-2-yn-1-yl(4-((2,3,5,6-tetramethoxyphenyl) sulfonamido) naphthalen-1-yl) amino) butanoic acid (DDO-1208)

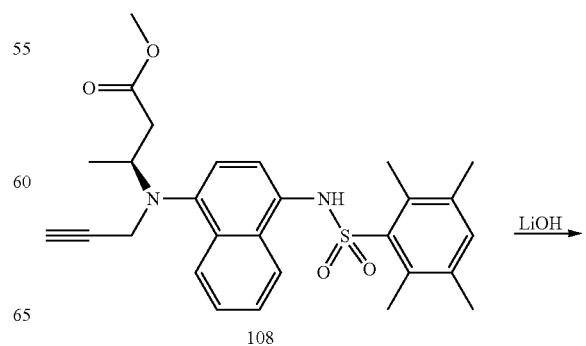

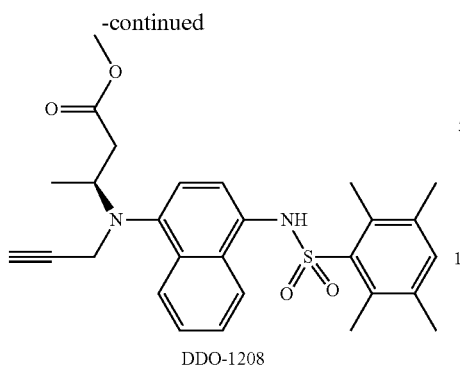

DDO-1208

In the same way as the synthesis method of compound DDO-1160, reaction is performed on compound 108 (0.10 mg, 0.20 mmol) and 2M aqueous LiOH (1.00 mL, 2.00 mmol) as starting materials to obtain a white solid DDO-1208 of 60.10 mg with yield of 63%; $^1$H NMR (300 MHz, DMSO-$d_6$) δ 9.90 (s, 1H), 8.18-8.08 (m, 2H), 7.48 (td, J=6.1, 5.3, 2.5 Hz, 2H), 7.25 (d, J=8.0 Hz, 1H), 7.17 (s, 1H), 6.97 (d, J=8.0 Hz, 1H), 4.00-3.85 (m, 2H), 3.69 (s, 1H), 2.92 (s, 1H), 2.54 (d, J=3.9 Hz, 1H), 2.38-2.30 (m, 1H), 2.23 (s, 6H), 2.15 (s, 6H), 1.14 (dd, J=16.5, 6.5 Hz, 3H); HRMS (ESI): found 479.1996. ($C_{27}H_{30}N_2O_4S$, [M+H]$^+$, requires 479.1999); HPLC (85:15 methanol:water with 1‰ TFA): $t_R$=12.68 min, 96.84%.

Synthesis of (S)-3-((4-((N-(Carboxymethyl)-2,3,5,6-tetramethylphenyl) sulfonamido) naphthalen-1-yl) (prop-2-yn-1-yl) amino) butanoic acid (DDO-1209)

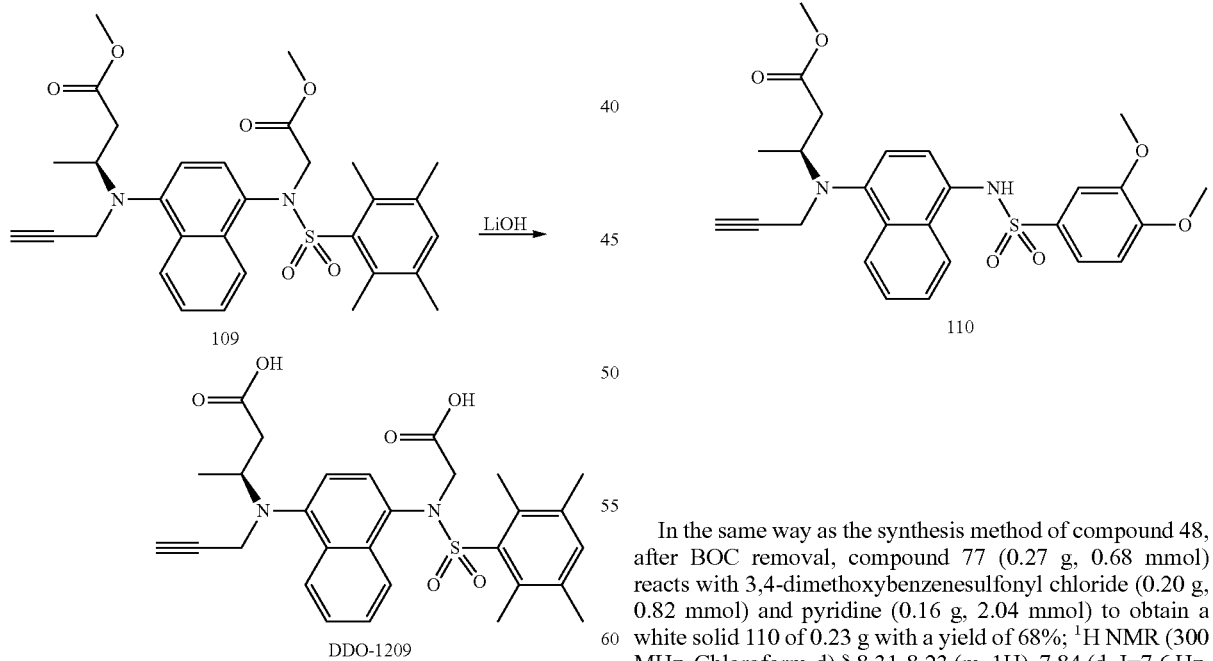

In the same way as the synthesis method of compound DDO-1161, reaction is performed on compound 109 (68.20 mg, 0.12 mmol) and 2M aqueous LiOH (1.50 mL, 3.00 mmol) as starting materials to obtain a white solid DDO-1209 of 48.30 mg with yield of 75%; $^1$H NMR (300 MHz, DMSO-$d_6$) δ 12.52 (s, 2H), 8.16-8.02 (m, 1H), 7.89 (dd, J=11.9, 8.4 Hz, 1H), 7.58 (t, J=7.9 Hz, 1H), 7.44 (t, J=7.5 Hz, 1H), 7.34 (dd, J=8.2, 5.0 Hz, 2H), 7.12 (d, J=3.8 Hz, 1H), 4.73 (ddd, J=17.7, 5.0, 2.5 Hz, 1H), 4.47 (d, J=17.4 Hz, 1H), 4.07-3.83 (m, 2H), 3.76-3.66 (m, 1H), 2.96 (dd, J=5.0, 2.5 Hz, 1H), 2.62-2.53 (m, 1H), 2.40-2.31 (m, 1H), 2.07 (dd, J=6.8, 3.3 Hz, 12H), 1.28-1.21 (m, 3H); HRMS(ESI): found 537.2051 ($C_{29}H_{32}N_2O_6S$, [M+H]$^+$, requires 537.2053); HPLC (85:15 methanol:water with 1‰ TFA): $t_R$=10.67 min, 100.00%.

Synthesis of (S)-methyl 3-((4-((3,4-dimethoxyphenyl) sulfonamido) naphthalen-1-yl) (prop-2-yn-1-yl) amino) butanoate (110)

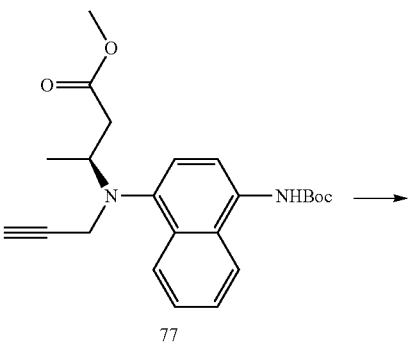

In the same way as the synthesis method of compound 48, after BOC removal, compound 77 (0.27 g, 0.68 mmol) reacts with 3,4-dimethoxybenzenesulfonyl chloride (0.20 g, 0.82 mmol) and pyridine (0.16 g, 2.04 mmol) to obtain a white solid 110 of 0.23 g with a yield of 68%; $^1$H NMR (300 MHz, Chloroform-d) δ 8.31-8.23 (m, 1H), 7.84 (d, J=7.6 Hz, 1H), 7.47-7.41 (m, 4H), 7.38 (d, J=4.1 Hz, 1H), 7.08 (d, J=2.2 Hz, 1H), 6.92 (s, 1H), 6.85 (d, J=5.8 Hz, 1H), 4.09-3.99 (m, 2H), 3.96 (d, J=2.4 Hz, 1H), 3.91 (s, 3H), 3.65 (s, 3H), 3.62 (s, 3H), 2.72-2.65 (m, 1H), 2.42 (dd, J=14.9, 8.6 Hz, 1H), 2.21 (t, J=2.3 Hz, 1H), 1.33 (d, J=5.0 Hz, 3H); ESI-MS m/z: 496.2 [M+H]$^+$.

Synthesis of (S)-methyl 3-((4-(3,4-dimethoxy-N-(2-methoxy-2-oxoethyl) phenyl) sulfonamido) naphthalen-1-yl)(prop-2-yn-1) yl) amino) butanoate (111)

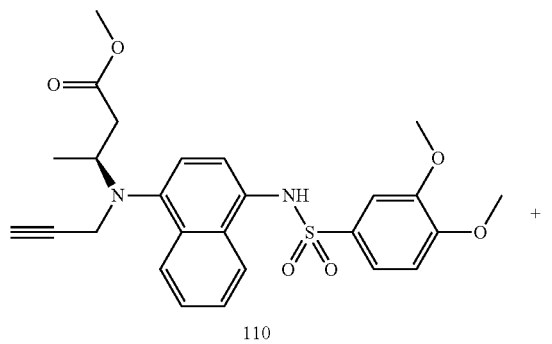

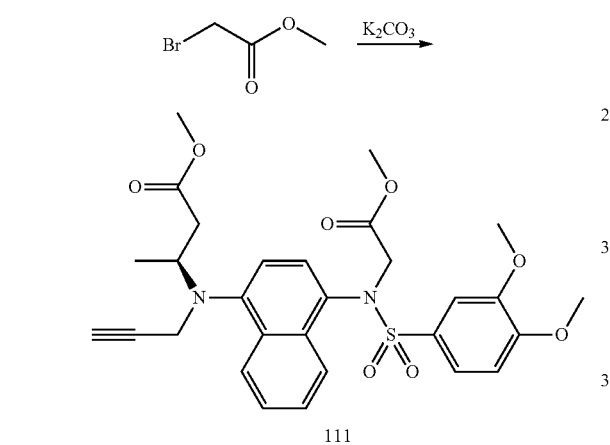

In the same way as the synthesis method of compound 49, reaction is performed on compound 110 (0.10 g, 0.20 mmol), methyl bromoacetate (36.72 mg, 0.24 mmol) and K₂CO₃ (82.80 mg, 0.60 mmol) as starting materials to obtain a pale yellow solid 111 of 60.20 mg with yield of 53%; ESI-MS m/z: 541.2 [M+H]⁺.

Synthesis of (S)-3-((4-((3,4-dimethoxyphenyl) sulfonamido) naphthalen-1-yl) (prop-2-yn-1-yl) amino) butanoic acid (DDO-1210)

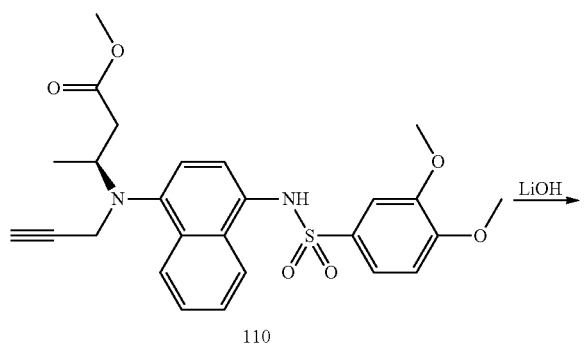

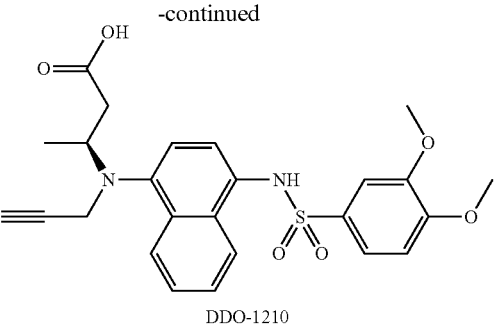

In the same way as the synthesis method of compound DDO-1160, reaction is performed on compound 110 (0.10 g, 0.20 mmol) and 2M aqueous LiOH (1.00 mL, 2.00 mmol) as starting materials to obtain a white solid DDO-1210 of 60.80 mg with yield of 62%; ¹H NMR (300 MHz, DMSO-d₆) δ 12.19 (s, 1H), 9.89 (s, 1H), 8.16 (d, J=8.3 Hz, 1H), 7.98 (d, J=8.3 Hz, 1H), 7.51-7.38 (m, 2H), 7.35-7.27 (m, 2H), 7.11-7.03 (m, 2H), 6.98 (d, J=2.2 Hz, 1H), 4.02-3.84 (m, 2H), 3.81 (s, 3H), 3.70 (t, J=9.9 Hz, 1H), 3.54 (s, 3H), 2.94 (d, J=2.2 Hz, 1H), 2.59-2.53 (m, 1H), 2.41-2.31 (m, 1H), 1.18 (d, J=6.4 Hz, 3H); HRMS(ESI): found 483.1583 (C₂₅H₂₆N₂O₆S, [M+H]⁺, requires 483.1584); HPLC (85:15 methanol:water with 1‰ TFA) t_R=8.62 min, 98.71%.

Synthesis of (S)-3-((4-((N-(Carboxymethyl)-3,4-dimethoxyphenyl) sulfonamido) naphthalen-1-yl) (prop-2-yn-1-yl) amino) butanoic acid (DDO-1211)

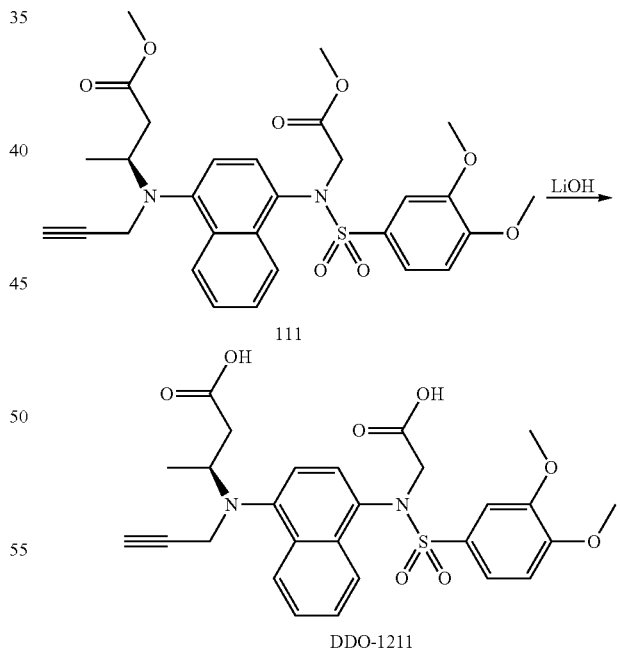

In the same way as the synthesis method of compound DDO-1161, reaction is performed on compound 111 (60.20 mg, 0.10 mmol) and 2M aqueous LiOH (1.00 mL, 2.00 mmol) as starting materials to obtain a white solid DDO-1211 of 40.30 mg with yield of 74%; ¹H NMR (300 MHz, DMSO-d₆) δ 12.47 (s, 2H), 8.22-8.08 (m, 2H), 7.58-7.47 (m, 2H), 7.31 (d, J=8.1 HZ, 2H), 7.13 (td, J=8.2, 2.8 Hz, 2H), 6.94 (dd, J=4.6, 2.2 Hz, 1H), 4.50-4.32 (m, 2H), 4.07-3.88 (m, 2H), 3.85 (s, 3H), 3.77 (d, J=7.5 Hz, 1H), 3.69-3.58 (m, 3H), 2.98 (d, J=2.3 Hz, 1H), 2.62-2.54 (m, 1H), 2.44-2.34 (m, 1H), 1.26-1.18 (m, 3H); HRMS(ESI): found 541.1637. ($C_{27}H_{25}N_2O_8S$, [M+H]$^+$, requires 541.1639); HPLC (85:15 methanol:water with 1% TFA): $t_R$=8.13 min, 99.27%.

Synthesis of (S)-methyl 3-((4-((3-fluoro-4-methoxyphenyl) sulfonamido) naphthalen-1-yl) (prop-2-yn-1-yl) amino) butanoate (112)

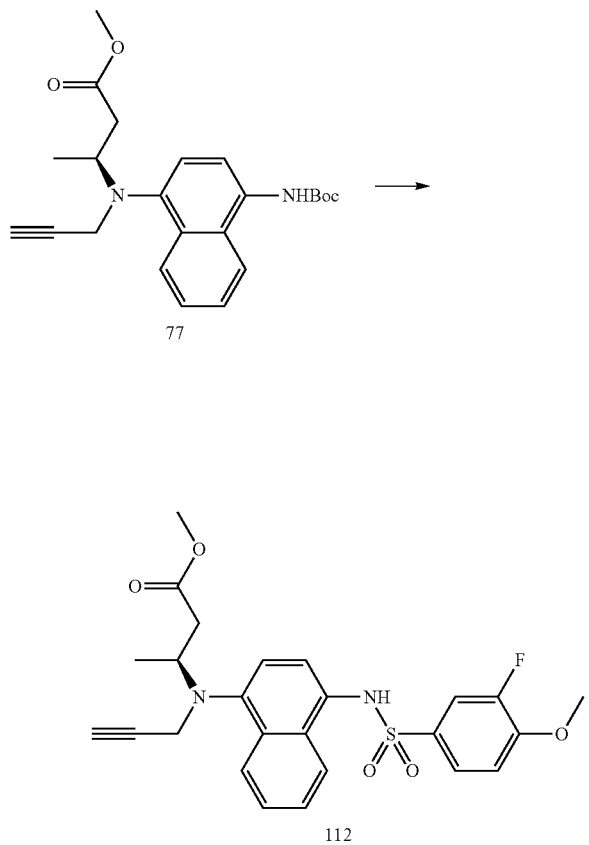

In the same way as the synthesis method of compound 48, after BOC removal, compound 77 (0.27 g, 0.68 mmol) reacts with 3-fluoro-4-methoxybenzenesulfonyl chloride (0.18 g, 0.82 mmol) and pyridine (0.16 g, 2.04 mmol) to obtain a white solid 112 of 0.21 g with a yield of 64%; $^1$H NMR (300 MHz, Chloroform-d) δ 8.26 (dd, J=7.8, 1.9 Hz, 1H), 7.85 (dd, J=8.7, 6.9 Hz, 1H), 7.49 (tdd, J=7.3, 5.3, 1.9 Hz, 4H), 7.42 (d, J=7.9 Hz, 1H), 7.37-7.30 (m, 1H), 6.95 (d, J=9.8 Hz, 1H), 6.92-6.87 (m, 1H), 4.03 (d, J=3.0 Hz, 1H), 4.01-3.92 (m, 2H), 3.91 (s, 3H), 3.61 (d, J=5.6 Hz, 3H), 2.70 (dt, J=14.9, 5.8 Hz, 1H), 2.51-2.40 (m, 1H), 2.22 (t, J=2.3 Hz, 1H), 1.35 (d, J=6.5 Hz, 3H); ESI-MS m/z: 485.1 [M+H]$^+$.

Synthesis of (S)-methyl 3-((4-((3-fluoro-4-methoxy-N-(2-methoxy-2-oxoethyl) phenyl) sulfonamido) naphthalen-1-yl)(prop-2-yn-1) yl) amino) butanoate (113)

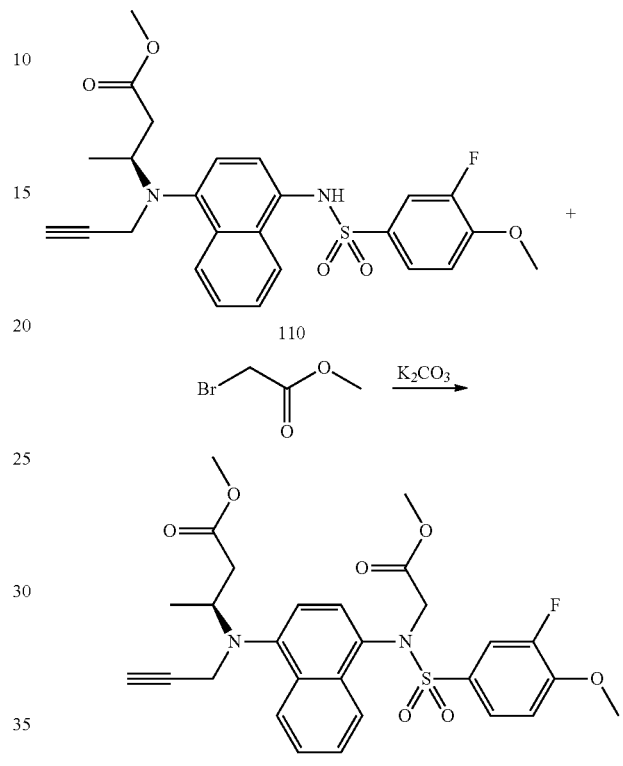

In the same way as the synthesis method of compound 49, reaction is performed on compound 112 (0.10 g, 0.20 mmol), methyl bromoaceate (36.72 mg, 0.24 mmol) and $K_2CO_3$ (82.80 mg, 0.60 mmol) as starting materials to obtain a pale yellow solid 113 of 64.80 mg with yield of 58%; ESI-MS m/z: 557.2 [M+H]$^+$.

Synthesis of (S)-3-((4-((3-fluoro-4-methoxyphenyl) sulfonamido) naphthalen-1-yl) (prop-2-yn-1-yl) amino) butanoic acid (DDO-1212)

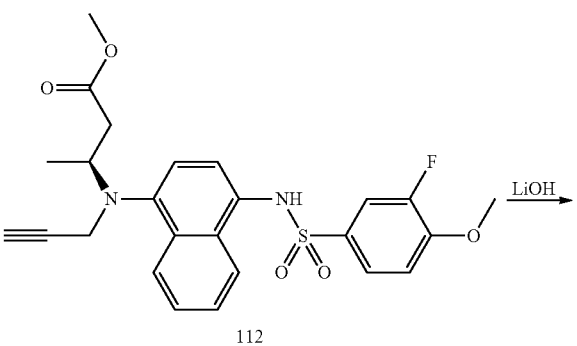

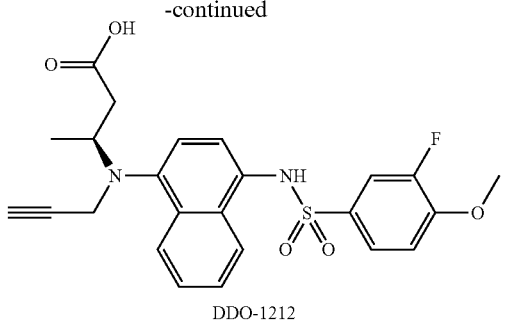

DDO-1212

In the same way as the synthesis method of compound DDO-1160, reaction is performed on compound 112 (0.10 g, 0.20 mmol) and 2M aqueous LiOH (1.00 mL, 2.00 mmol) as starting materials to obtain a white solid DDO-1212 of 56.80 mg with yield of 60%; $^1$H NMR (300 MHz, DMSO-$d_6$) δ 8.25-7.90 (m, 2H), 7.44 (s, 6H), 7.03 (s, 1H), 3.89 (d, J=16.3 Hz, 5H), 3.70 (s, 1H), 2.92 (s, 1H), 2.68 (s, 1H), 2.33 (s, 1H), 1.18 (d, J=14.8 Hz, 3H); HRMS(ESI): found 471.1382. ($C_{24}H_{23}FN_2O_5S$, [M+H]$^+$, requires 471.1384); HPLC (85:15 methanol:water with 1‰ TFA): $t_R$=8.33 min, 96.08%.

Synthesis of (S)-3-((4-((N-(Carboxy)-3-fluoro-4-methoxyphenyl) sulfonamide) naphthalen-1-yl) (prop-2-yn-1-yl) amino) butanoic acid (DDO-1213)

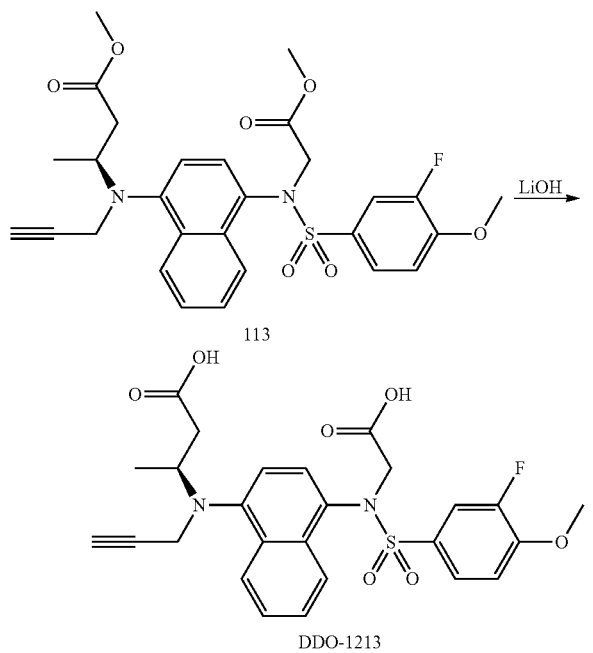

DDO-1213

In the same way as the synthesis method of compound DDO-1161, reaction is performed on compound 113 (64.80 mg, 0.12 mmol) and 2M aqueous LiOH (1.50 mL, 3.00 mmol) as starting materials to obtain a while solid DDO-1213 of 46.30 mg with yield of 73% $^1$H NMR (300 MHz, DMSO $d_6$) δ 8.21-8.13 (m, 1H), 8.11-8.05 (m, 1H), 7.54-7.45 (m, 3H), 7.40 (d, J=8.6 Hz, 1H), 7.28 (dd, J=7.6, 3.6 Hz, 2H), 7.17 (d, J=8.0 Hz, 1H), 4.52 (d, J=17.8 Hz, 1H), 4.41-4.32 (m, 1H), 3.97 (d, J=3.5 Hz, 1H), 3.91 (s, 3H), 3.75 (s, 2H), 2.96 (d, J=2.5 Hz, 1H), 2.59 (dd, J=15.2, 4.9 Hz, 1H), 2.38 (dq, J=11.9, 4.6, 2.7 Hz, 1H), 1.22-1.12 (m, 3H); HRMS(ESI): found 529.1436. ($C_{26}H_{25}FN_2O_7S$, [M+H]$^+$, requires 529.1439); HPLC (85:15 methanol:water with 1‰ TFA): $t_R$=8.22 min, 95.96%.

Synthesis of (S)-methyl 3-((4-((3-chloro-4-methoxyphenyl) sulfonamido) (naphthalen-1-yl) (prop-2-yn-1-yl) amino) butanoate (114)

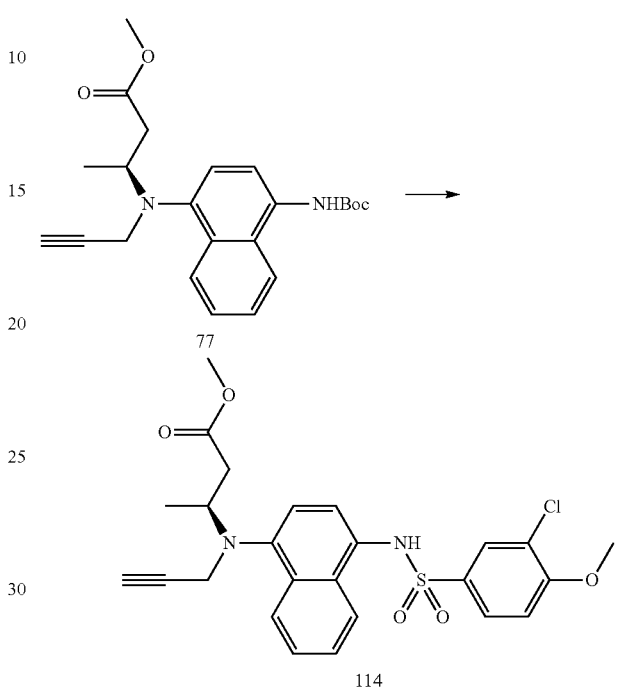

114

In the same way as the synthesis method of compound 48, after BOC removal, compound 77 (0.27 g, 0.68 mmol) reacts with 3-chloro-4-methoxybenzenesulfonyl chloride (0.20 g, 0.82 mmol) and pyridine (0.16 g, 2.04 mmol) to obtain a white solid 114 of 0.24 g with a yield of 70%; $^1$H NMR (300 MHz, Chloroform-d) δ 8.29-8.16 (m, 1H), 7.91-7.83 (m, 1H), 7.81-7.74 (m, 1H), 7.65-7.58 (m, 1H), 7.55-7.40 (m, 3H), 7.31 (d, J=8.8 Hz, 1H), 6.92-6.82 (m, 2H), 4.05 (d, J=9.4 Hz, 2H), 3.97 (s, 1H), 3.93 (s, 3H), 3.61 (d. J=5.7 Hz, 3H), 2.84 (s, 1H), 2.69 (dd, J=14.8, 4.8 Hz, 1H), 2.49-2.38 (m, 1H), 1.33 (d, J=5.9 Hz, 3H); ESI-MS m/z: 501.1 [M+H]$^+$.

Synthesis of (S)-methyl 3-((4-((3-chloro-4-methoxy-N-(2-methoxy-2-oxoethyl) phenyl) sulfonamido) naphthalen-1-yl)(prop-2-yn-1) yl) amino) butanoate (115)

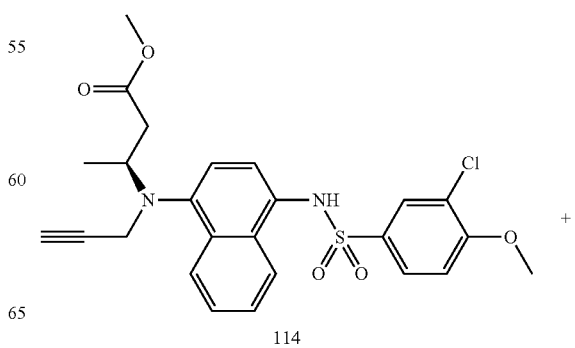

114

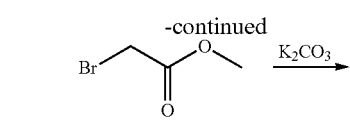

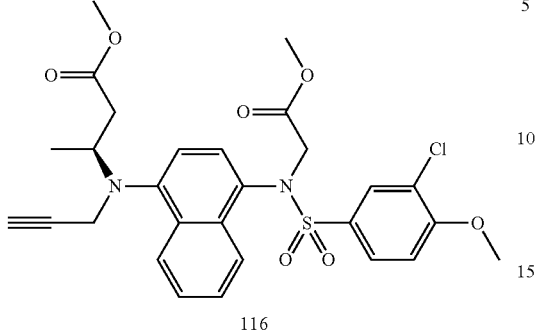

116

In the same way as the synthesis method of compound 49, reaction is performed on compound 114 (0.10 g, 0.20 mmol), methyl bromoacetate (36.72 mg, 0.24 mmol) and K$_2$CO$_3$ (82.80 mg, 0.60 mmol) as starting materials to obtain a pale yellow solid 115 of 60.26 mg with yield of 52%; ESI-MS m/z: 573.1 [M+H]$^+$.

Synthesis of (S)-3-((4-(((3-chloro-4-methoxyphenyl) sulfonamido) naphthalen-1-yl) (prop-2-yn-1-yl) amino) butanoic acid (DDO-1214)

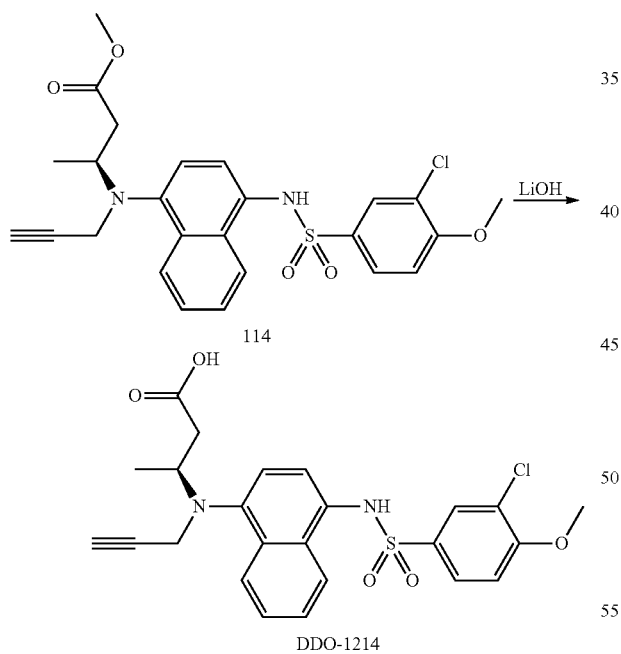

DDO-1214

In the same way as the synthesis method of compound DDO-1160, reaction is performed on compound 114 (0.10 g, 0.20 mmol) and 2M aqueous LiOH (1.00 mL, 2.00 mmol) as starting materials to obtain a white solid DDO-1214 of 58.00 mg with yield of 59%; NMR (300 MHz, DMSO-d$_6$) δ 10.07 (s, 1H), 8.16 (d, J=8.2 Hz, 1H), 8.00 (t, J=7.7 Hz, 1H), 7.61 (dd, J=6.1, 2.3 Hz, 2H), 7.47 (p, J=7.1 Hz, 2H), 7.26 (dd, J=16.9, 8.6 Hz, 2H), 7.02 (d, J=8.1 Hz, 1H), 3.97 (d, J=18.2 Hz, 2H), 3.90 (s, 3H), 3.71 (s, 1H), 2.94 (s, 1H), 2.59-2.51 (m, 1H), 2.35 (dd, J=15.1, 9.3 Hz, 1H), 1.19 (t, J=9.2 Hz, 3H); HRMS(ESI): found 487.1078 (C$_{24}$H$_{23}$ClN$_2$O$_5$S, [M+H]$^+$, requires 487.1089); HPLC (85:15 methanol:water with 1‰ TFA): t$_R$=9.98 min, 96.16%.

Synthesis of (S)-3-((4-((N-(Carboxy)-3-chloro-4-methoxyphenyl) sulfonamido) naphthalen-1-yl) (prop-2-yn-1-yl) amino) butanoic acid (DDO-1215)

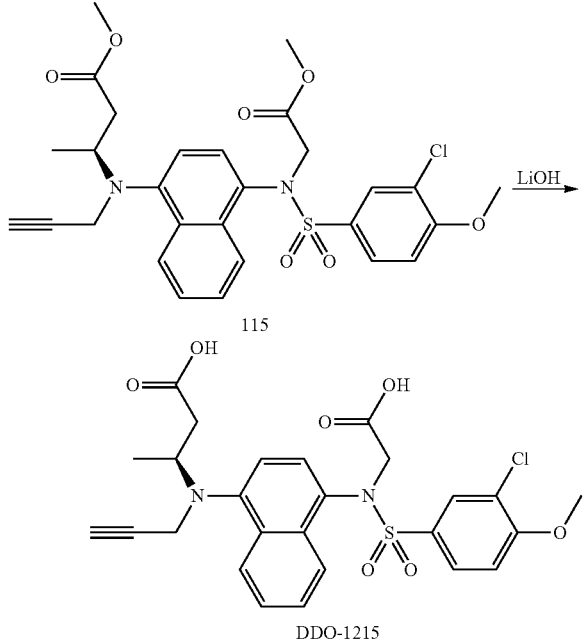

DDO-1215

In the same way as the synthesis method of compound DDO-1161, reaction is performed on compound 115 (60.26 mg, 0.10 mmol) and 2M aqueous LiOH (1.00 mL, 2.00 mmol) as starting materials to obtain a white solid DDO-1215 of 44.30 mg with yield of 81%; $^1$H NMR (300 MHz, DMSO-d$_6$) δ 8.14 (ddd, J=13.9, 7.7, 2.9 Hz, 2H), 7.63-7.55 (m, 2H), 7.49 (tt, J=9.2, 3.9 Hz, 2H), 7.30-7.22 (m, 2H), 7.15 (d, J=7.9 Hz, 1H), 4.51 (d, J=17.7 Hz, 1H), 4.39-4.29, (m, 1H), 3.97 (s, 1H), 3.93 (s, 3H), 3.75 (s, 2H), 2.99-2.91 (m, 1H), 2.59 (dd, J=14.8, 4.1 Hz, 1H), 2.38 (dd, J=15.8, 9.1 Hz, 1H), 1.23-1.15 (m, 3H); HRMS(ESI): found 545.1143 (C$_{26}$H$_{25}$ClN$_2$O$_7$S, [M+H]$^+$, requires 545.1143); HPLC (85:15 methanol:water with 1‰ TFA): tR=9.96 min, 98.99%.

Synthesis of (S)-methyl 3-((4-((4-methoxy-3-methylphenyl) sulfonamido) naphthalen-1-yl) (prop-2-yn-1-yl) amino) butanoate (116)

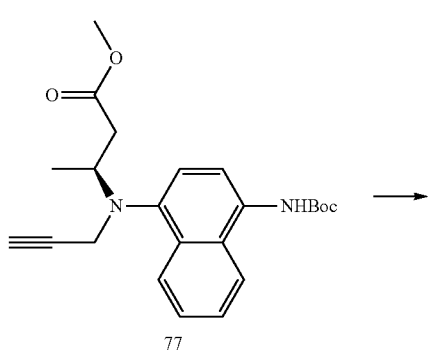

77

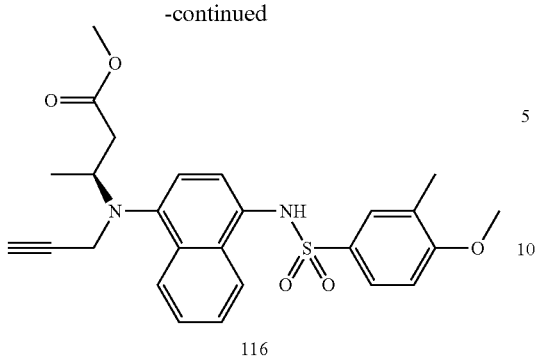

116

In the same way as the synthesis method of compound 48, after BOC removal, compound 77 (0.27 g, 0.68 mmol) reacts with 3-methyl-4-methoxybenzenesulfonyl chloride (0.18 g, 0.82 mmol) and pyridine (0.16 g, 2.04 mmol) to obtain a white solid 116 of 0.22 g with a yield of 67%; $^1$H NMR (300 MHz, Chloroform-d) δ 8.33-8.21 (m, 1H), 7.88 (dd, J=15.4, 8.0 Hz, 1H), 7.61 (dd, J=8.7, 2.4 Hz, 1H), 7.47 (ddd, J=21.5, 11.3, 6.4 Hz, 4H), 7.30 (d, J=3.5 Hz, 1H), 6.89 (s, 1H), 6.77 (dd, J=9.4, 3.9 Hz, 1H), 4.12-4.00 (m, 1H), 4.00-3.88 (m, 2H), 3.86 (s, 3H), 3.60 (d, J=7.2 Hz, 3H), 2.68 (dd, J=15.0, 4.7 Hz, 1H), 2.42 (dd, J=15.1, 8.7 Hz, 1H), 2.21 (t, J=2.3 Hz, 1H), 2.13 (d, J=3.1 Hz, 314), 1.35 (q, J=3.9, 3.0 Hz, 314), ESI-MS m/z: 481.2 [M+H]$^+$.

Synthesis of (S)-methyl 3-((4-((4-methoxy-N-(2-methoxy-2-oxoethyl)-3-methylphenyl) sulfonamido) naphthalen-1-yl)(prop-2-yn-1-methyl) yl) amino) butanoate (117)

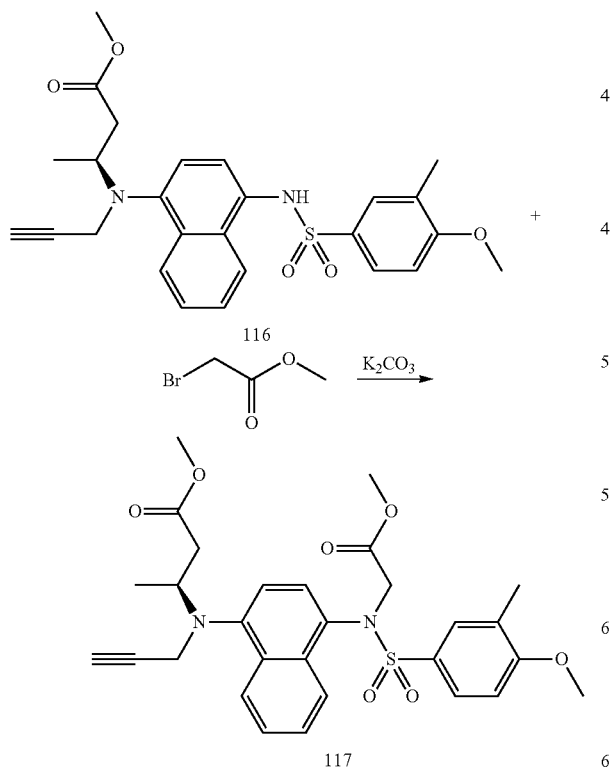

In the same way as the synthesis method of compound 49, reaction is performed on compound 116 (0.10 g, 0.21 mmol), methyl bromoacetate (38.56 mg, 0.25 mmol) and K$_2$CO$_3$ (86.94 mg, 0.63 mmol) as starting materials to obtain a pale yellow solid 117 of 70.40 mg with yield of 64%; ESI-MS m/z: 553.2 [M+H]$^+$.

Synthesis of (S)-3-((4-((4-methoxy-3-methylphenyl) sulfonamido) naphthalen-1-yl) (prop-2-yn-1-yl) amino) butanoic acid (DDO-1216)

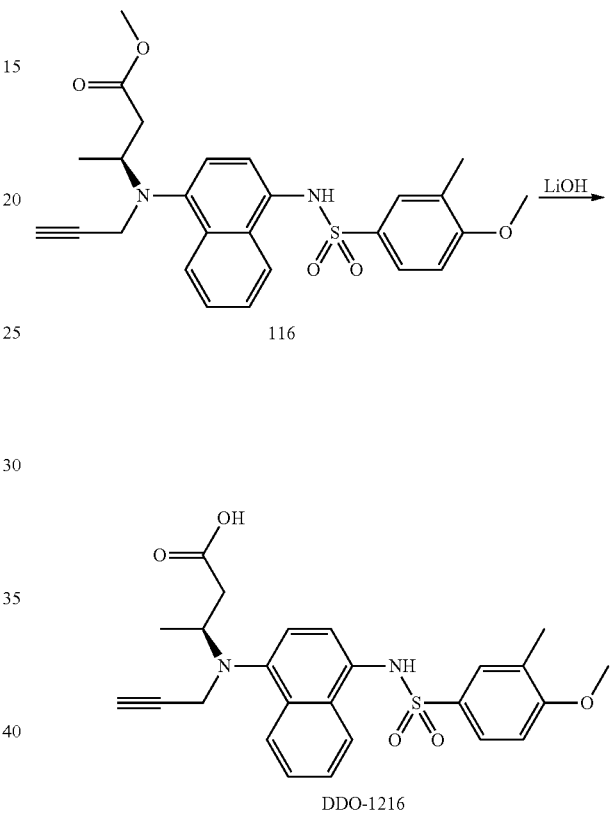

In the same way as the synthesis method of compound DDO-1160, reaction is performed on compound 116 (0.10 g, 0.21 mmol) and 2M aqueous LiOH (1.00 mL, 100 mmol) as starting materials to obtain a white solid DDO-1216 of 58.00 mg with yield of 60%; $^1$H NMR (300 MHz, DMSO-d$_6$) δ 9.87 (s, 1H), 8.15 (d, J=8.2 Hz, 1H), 8.04 (d, J=8.0 Hz, 1H), 7.55-7.36 (m, 4H), 7.27 (d, J=8.0 Hz, 1H), 7.06-6.97 (m, 2H), 3.92 (d, J=9.1 Hz, 2H), 3.82 (s, 3H), 3.70 (s, 1H), 2.95 (d. J=2.2 Hz, 1H), 2.61-2.53 (m, 1H), 2.33 (dd, J=15.2, 9.3 Hz, 1H), 2.08 (s, 3H), 1.24-1.11 (m, 3H); HRMS(ESI): found 467.1640. (C$_{25}$H$_{26}$N$_2$O$_5$S, [M+H]$^+$, requires 467.1635); HPLC (85:15 methanol:water 1‰ TFA): t$_R$=8.51 min, 99.41%.

Synthesis of (S)-3-((4-((N-(Carboxymethyl)-4-methoxy-3-methylphenyl) sulfonamido) naphthalen-1-yl)(prop-2-yn-1-yl) amino) butanoic acid (DDO-1217)

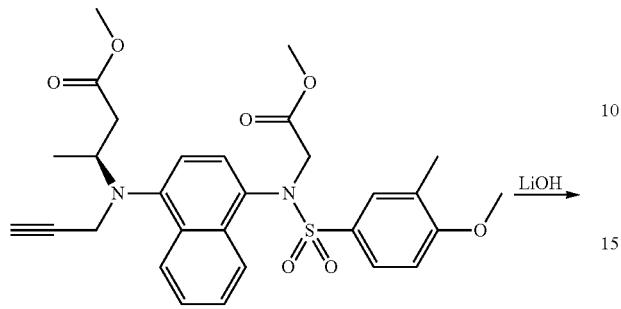

116

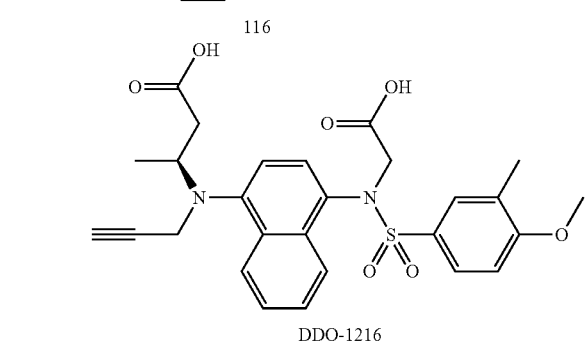

DDO-1216

In the same way as the synthesis method of compound DDO-1161, reaction is performed on compound 117 (70.40 mg, 0.13 mmol) and 2M aqueous LiOH (1.50 mL, 3.00 mmol) as starting materials to obtain a white solid DDO-1217 of 48.30 mg with yield of 70%; $^1$H NMR (300 MHz, DMSO-$d_6$) δ 8.16 (dt, J=6.8, 3.4 Hz, 2H), 7.51 (dt, J=15.9, 7.9 Hz, 3H), 7.35 (s, 1H), 7.27 (d. J=8.1 Hz, 1H), 7.07 (dd, J=8.2, 4.0 Hz, 2H), 4.40 (s. 2H), 3.96 (d, J=10.5 Hz, 2H), 3.87 (s, 3H), 3.76 (s, 1H), 2.99 (s, 1H), 2.59 (d, J=14.5 Hz, 1H), 2.46-2.35 (m, 1H), 2.13 (s, 3H), 1.20 (dd, J=7.2, 4.4 Hz, 3H); HRMS(ESI): found 525.1699. ($C_{27}H_{28}N_2O_7S$, [M+H]$^+$, requires 525.1699); HPLC (85:15 methanol:water with 19.60 TFA): $t_R$=8.42 min, 99.45%.

Synthesis of (S)-methyl 3-((4-((4-methoxy-2,3,6-trimethylphenyl) sulfonamido) naphthalen-1-yl)(prop-2-yn-1-yl) amino) butanoate (118)

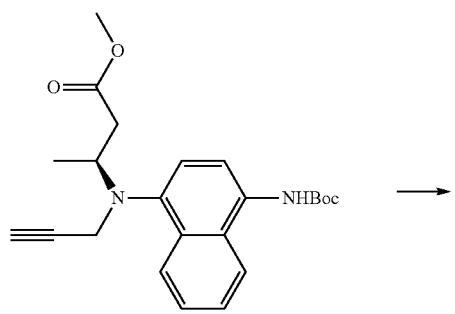

77

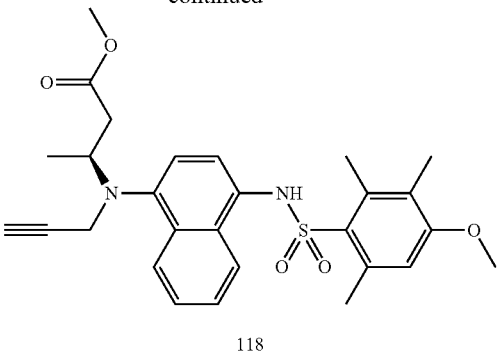

118

In the same way as the synthesis method of compound 48, after BOC removal, compound 77 (0.27 g. 0.68 mmol) reacts with 4-methoxy-2,3,6-trimethylbenzenesulfonyl chloride (0.20 g, 0.82 mmol) and pyridine (0.16 g, 2.04 mmol) to obtain a white solid 118 of 0.24 g with a yield of 69%; $^1$H NMR (300 MHz, Chloroform-d) δ 8.28-8.22 (m, 1H), 8.08-8.02 (m, 1H), 7.55-7.47 (m, 2H), 7.32 (s, 1H), 7.00 (d, J=8.0 Hz, 1H), 6.70 (s, 1H), 6.53 (s, 1H), 4.05-3.97 (m, 1H), 3.95-3.88 (m, 2H), 3.86 (s, 3H), 3.59 (s, 3H), 2.67-2.60 (m, 1H), 2.56 (s, 3H), 2.45 (s, 3H), 2.42-2.32 (m, 1H), 2.17 (d, J=2.3 Hz, 1H), 2.15 (s, 3H), 1.33-1.29 (m, 3H); ESI-MS m/z: 509.2 [M+H]$^+$.

Synthesis of (S)-methyl 3-((4-((4-methoxy-N-(2-methoxy-2-oxoethyl)-2,3,6-trimethylphenyl) sulfonamidyl) naphthalen-1-yl)(prop-2-one) yn-1-yl) amino) butanoate (119)

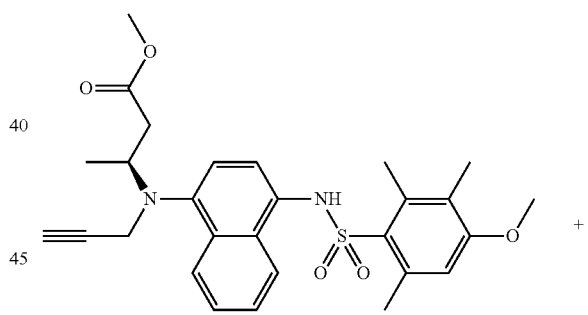

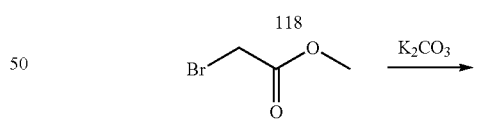

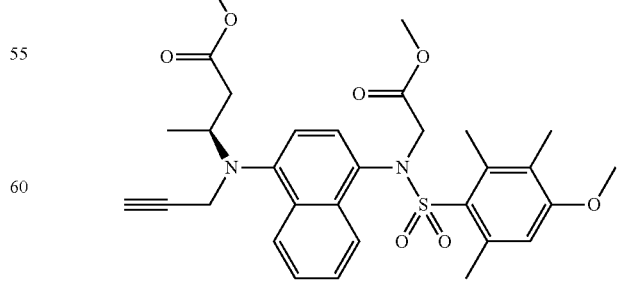

119

In the same way as the synthesis method of compound 49, reaction is performed on compound 118 (0.10 g, 0.20 mmol), methyl bromoacetate (36.72 mg, 0.24 mmol) and K$_2$CO$_3$ (82.80 mg, 0.60 mmol) as starting materials to obtain a pale yellow solid 119 of 71.06 mg with yield of 61%; ESI-MS m/z: 581.2 [M+H]$^+$.

Synthesis of (S)-3-((4-((4-methoxy-2,3,6-trimethylphenyl) sulfonamido) naphthalen-1-yl) (prop-2-yn-1-yl) amino) butanoic acid (DDO-1218)

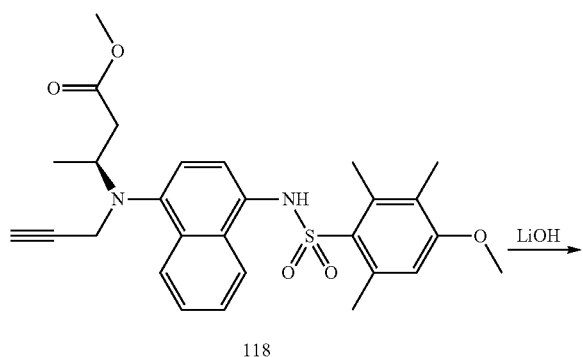

In the same way as the synthesis method of compound DDO-1160, reaction is performed on compound 118 (0.10 g, 0.20 mmol) and 2M aqueous LiOH (1.00 mL, 2.00 mmol) as starting materials to obtain a white solid DDO-1218 of 60.60 mg with yield of 60%; $^1$H NMR (300 MHz, DMSO-d$_6$) δ 12.28 (s, 1H), 9.86 (s, 1H), 8.21 (d, J=8.1 Hz, 1H), 8.13 (d, J=8.1 Hz, 1H), 7.52 (dq, J=13.4, 6.6 Hz, 2H), 7.30 (d, J=8.0 Hz, 1H), 7.02 (d, J=7.9 Hz, 1H), 6.74 (s, 1H), 3.98 (d, J=9.1 Hz, 2H), 3.84 (s, 3H), 3.74 (s, 1H), 2.98 (s, 1H), 2.61 (s, 1H), 2.41 (s, 3H), 2.36 (s, 1H), 2.33 (s, 3H), 2.08 (s, 3H), 1.22 (d, J=6.4 Hz, 3H); HRMS(ESI): found 495.1946 (C$_{27}$H$_{30}$N$_2$O$_5$S, [M+H]$^+$, requires 495.1948); HPLC (85:15 methanol:water with 1‰ TFA): t$_R$=10.17 min, 97.3%.

Synthesis of (S)-3-((4-((N-(Carboxymethyl)-4-methoxy-2,3,6-trimethylphenyl) sulfonamidyl) naphthalen-1-yl)(prop-2-yn-1-yl) amino) butanoic acid (DDO-1219)

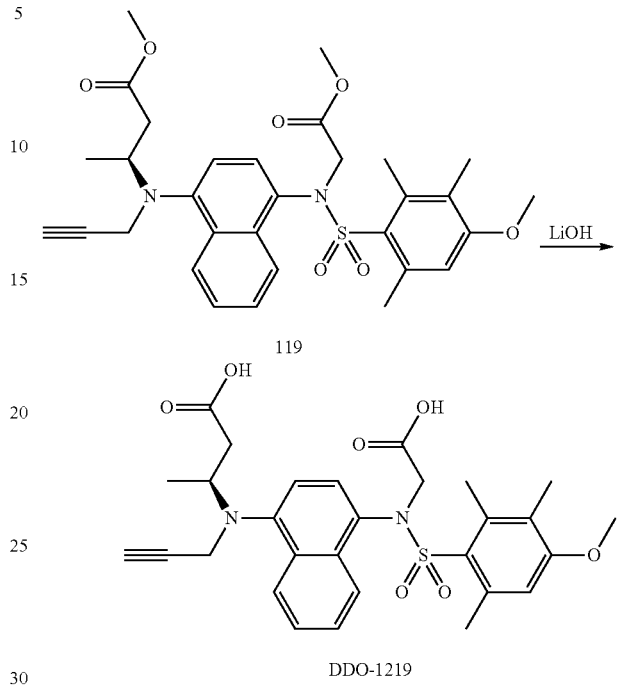

In the same way as the synthesis method of compound DDO-1161, reaction is performed on compound 119 (71.06 mg, 0.12 mmol) and 2M aqueous LiOH (1.50 mL, 3.00 mmol) as starting materials to obtain a white solid DDO-1219 of 47.20 mg with yield of 70%; $^1$H NMR (400 MHz, DMSO-d$_6$) δ 12.50 (s, 2H), 8.17-8.09 (m, 1H), 7.92 (t, J=8.0 Hz, 1H), 7.54 (d, J=8.0 Hz, 1H), 7.47-7.41 (m, 1H), 7.38-7.34 (m, 1H), 7.32 (dd, J=8.2, 2.0 Hz, 1H), 6.57 (d, J=10.4 Hz, 1H), 4.66 (d. J=17.7 Hz, 1H), 4.43 (d, J=17.7 Hz, 1H), 4.02-3.86 (m, 2H), 3.74 (d, J=3.0 Hz, 3H), 3.71 (s, 1H), 2.96 (dt, J=4.7, 2.3 Hz, 1H), 2.56 (dd, J=15.3, 4.3 Hz, 1H), 2.42-2.34 (m, 1H), 2.20 (d, J=14.3 Hz, 3H), 2.13 (d, J=2.6 Hz, 3H), 1.96 (d, J=7.0 Hz, 3H), 1.22 (d, J=5.6 Hz, 3H); HRMS(ESI): found 553.2000. (C$_{29}$H$_{32}$N$_2$O$_7$S, [M+H]$^+$, requires 553.2003); HPLC (85:15 methanol:water with 1‰ TFA): t$_R$=9.69 min, 95.7%.

Synthesis of (S)-methyl 3-((4-((4-methoxy-2,6-dimethylphenyl) sulfonamido) naphthalen-1-yl)(prop-2-yn-1-yl) amino) butanoate (120)

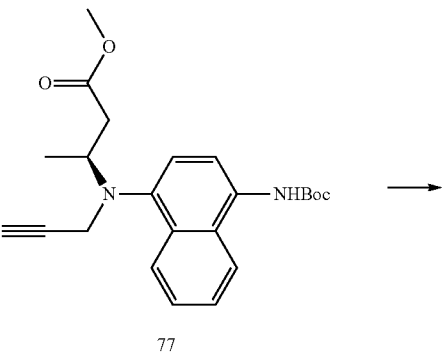

77

-continued

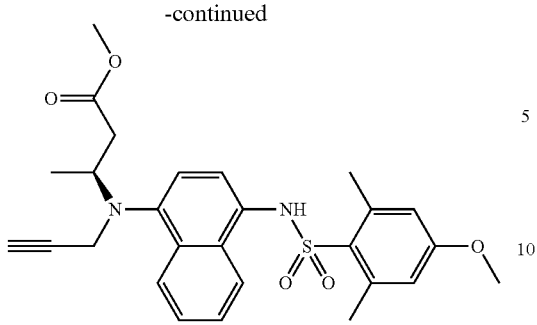

120

In the same way as the synthesis method of compound 48, after BOC removal, compound 77 (0.27 g, 0.68 mmol) reacts with 2,6-dimethyl-4-methoxybenzenesulfonyl chloride (0.19 g, 0.82 mmol) and pyridine (0.16 g, 2.04 mmol) to obtain a white solid 120 of 0.22 g with a yield of 65%; $^1$H NMR (300 MHz, Chloroform-d) δ 8.31-8.20 (m, 1H), 8.05-7.98 (m, 1H), 7.51 (dt, J=7.7, 4.5 Hz, 2H), 7.31 (s, 1H), 7.00 (d, J=7.9 Hz, 1H), 6.68 (s, 1H), 6.61 (s, 2H), 4.06-3.98 (m, 1H), 3.92 (dd, J=13.0, 2.4 Hz, 2H), 3.83 (d, J=3.5 Hz, 3H), 3.60 (s, 3H), 2.65 (dd, J=149, 4.6 Hz, 1H), 2.50 (s, 6H), 2.40 (dd, J=14.9, 8.6 Hz, 1H), 2.17 (t, J=2.3 Hz, 1H), 1.32 (d, J=6.2 Hz, 4H), ESI-MS m/z: 495.2 [M+H]$^+$.

Synthesis of (S)-methyl 3-((4-((4-methoxy-N-(2-methoxy-2-oxoethyl)-2,6-dimethylphenyl) sulfonamido) naphthalen-1-yl)(prop-2-yn-methyl)-1-yl) amino) butanoate (121)

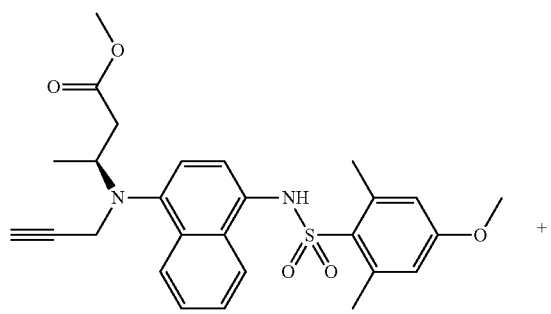

121

In the same way as the synthesis method of compound 49, reaction is performed on compound 120 (0.10 g, 0.20 mmol), methyl bromoacetate (36.72 mg, 0.24 mmol) and K$_2$CO$_3$ (82.80 mg, 0.60 mmol) as starting materials to obtain a pale yellow solid 121 of 68.60 mg with yield of 60%; ESI-MS m/z: 567.2 [M+H]$^+$.

Synthesis of (S)-3-((4-((4-methoxy-2,6-dimethylphenyl sulfonamide) naphthalen-1-yl) (prop-2-yn-1-yl) amino) butanoic acid (DDO-1220)

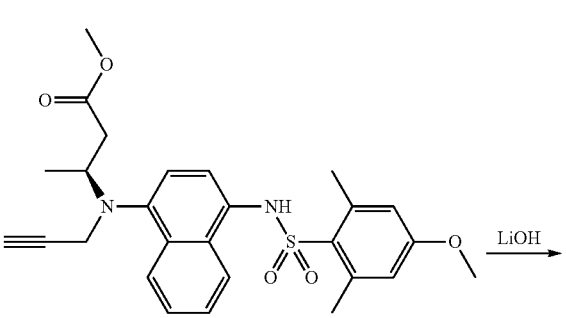

120

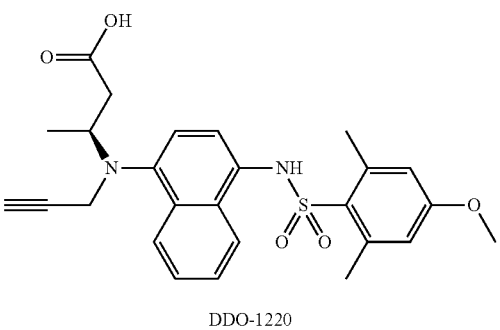

DDO-1220

In the same way as the synthesis method of compound DUO-1160, reaction is performed on compound 120 (7.20 mg, 0.20 mmol) and 2M aqueous LiOH (1.00 mL, 2.00 mmol) as starting materials to obtain a white solid DDO-1207 of 58.20 mg with yield of 60%; $^1$H NMR (300 MHz, DMSO-d$_6$) δ 12.19 (s, 1H), 9.79 (s, 1H), 8.15 (d, 8.3 Hz, 1H), 8.01 (d. J=8.5 Hz, 1H), 7.45 (p, J=7.1 Hz, 2H), 7.25 (d, J=7.9 Hz, 1H), 6.94 (d, J=8.2 Hz, 1H), 6.66 (s, 2H), 4.01-3.83 (m, 2H), 3.74 (d, J=2.1 Hz, 3H), 3.69 (s, 1H), 2.93 (s, 1H), 2.56 (s, 0H), 2.37 (s, 0H), 2.31 (d, J=2.4 Hz, 6H), 1.26-1.07 (m, 3H); $^{13}$C NMR (75 MHZ, DMSO-d$_6$) δ 172.86, 162.25, 144.52, 131.97, 131.03, 130.90, 128.96, 128.84, 125.78, 123.70, 123.62, 122.95, 119.59, 114.14, 81.10, 74.57, 55.57, 54.44, 38.66, 37.47, 17.19; HRMS (ESI): found 481.1787 (C$_{26}$H$_{28}$N$_2$O$_5$S, [M+H]$^+$, requires 481.1791); HPLC, (85:15 methanol:water with 1‰ TFA): t$_R$=8.86 min, 99.13%.

Synthesis of (S)-3-((4-((N-(Carboxy)-4-methoxy-2,6-dimethylphenyl) sulfonamido) naphthalen-1-yl) (prop-2-yn-1-yl) amino) butanoic acid (DDO-1221)

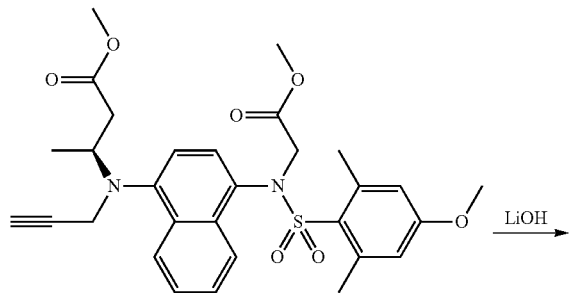

121

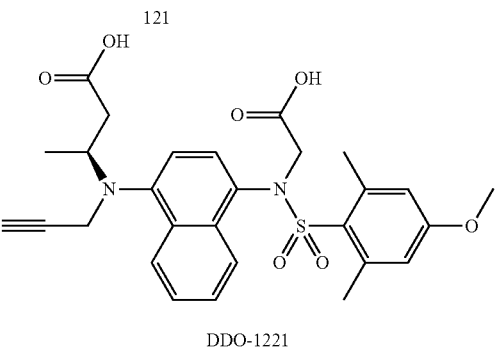

DDO-1221

In the same way as the synthesis method of compound DDO-1161, reaction is performed on compound 121 (7.20 mg, 0.12 mmol) and 2M aqueous LiOH (1.50 mL, 3.00 mmol) as starting materials to obtain a white solid DDO-1207 of 46.60 mg with yield of 71%; $^1$H NMR (300 MHZ, DMSO-$d_6$) δ 8.13 (t, J=7.5 Hz, 1H), 7.88 (d, J=8.4 Hz, 1H), 7.53-7.41 (m, 2H), 7.40-7.29 (m, 2H), 6.59 (d, J=8.9 Hz, 2H), 4.69 (d, J=17.7 Hz, 1H), 4.43 (d, J=17.7 Hz, 1H), 3.96 (s, 2H), 3.72 (s, 1H), 3.72-3.63 (m, 3H), 2.96 (s, 1H), 2.57 (d, J=14.1 Hz, 1H), 2.37 (t, J=11.9 Hz, 1H), 2.16 (d, J=3.4 Hz, 6H), 1.25-1.14 (m, 3H); $^1$H NMR (75 MHz, DMSO-$d_6$) δ 172.83, 170.00, 146.54, 132.83, 132.48, 129.82, 126.97, 125.99, 124.63, 123.61, 119.10, 114.17, 81.07, 74.69, 55.68, 54.58, 53.11, 38.67, 37.12, 17.11; HRMS(ESI): found 539.1842. ($C_{28}H_{30}N_2O_7S$, [M+H]$^+$, requires 539.1846); HPLC (85:15 methanol:water with 1% TFA): $t_R$=8.66 min, 98.77%.

Synthesis of (S)-methyl 3-((4-((2,3-dihydrobenzofuran)-5-sulfonamido) naphthalen-1-yl) (prop-2-yn-1-yl) amino) butanoate (122)

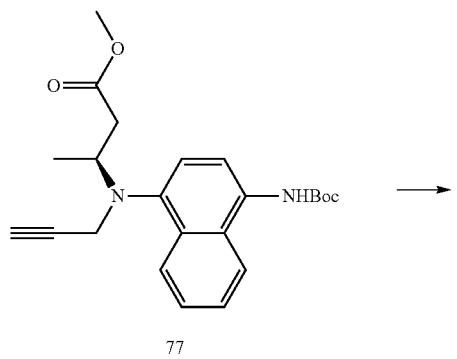

77

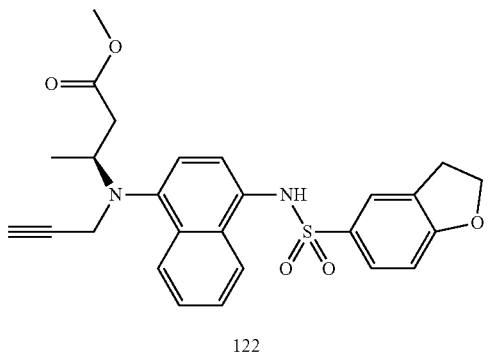

122

In the same way as the synthesis method of compound 48, after BOC removal, compound 77 (0.27 g, 0.68 mmol) reacts with 2,3-dihydrobenzofuran-5-sulfonyl chloride (0.18 g, 0.82 mmol) and pyridine (0.16 g, 2.04 mmol) to obtain a white solid 122 of 0.21 g with a yield of 65%; $^1$H NMR (300 MHz, Chloroform-d) δ 8.26 (dd, J=7.7, 1.9 Hz, 1H), 7.88 (dd, J=7.6, 1.8 Hz, 1H), 7.63-7.56 (m, 1H), 7.54-7.39 (m, 4H), 7.33 (d, J=8.4 Hz, 1H), 6.87 (s, 1H), 6.73 (d, J=8.4 Hz, 1H), 4.62 (t, J=8.8 Hz, 2H), 4.04 (d, J=5.1 Hz, 1H), 4.01-3.79 (m, 2H), 3.61 (d, J=6.8 Hz, 3H), 3.12 (t, J=8.8 Hz, 2H), 2.69 (dt, =15.1, 5.2 Hz, 1H), 2.51-2.39 (m, 1H), 2.22 (t, J=2.3 Hz, 1H), 1.38-1.32 (m, 3H); ESI-MS m/z: 479.2 [M+H]$^+$.

Synthesis of (S)-methyl 3-((N-(2-(2-methoxy-2-oxoethyl)-2,3-dihydrobenzofuran-5-sulfonamido) naphthalen-1-yl) (prop-2-yn-1-yl) amino) butanoate (123)

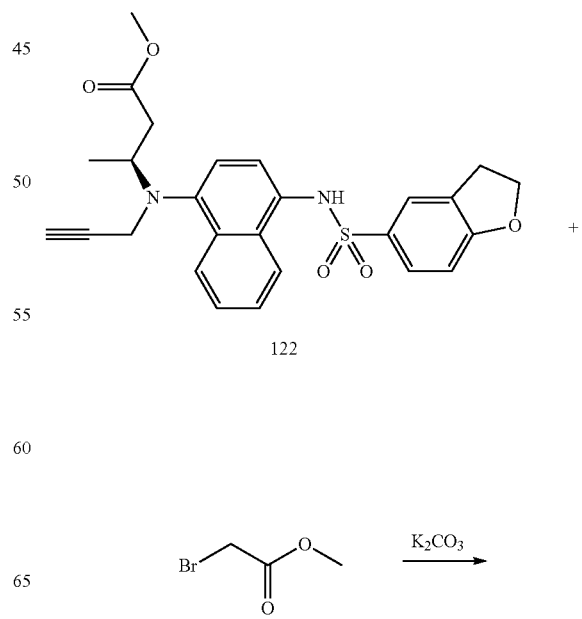

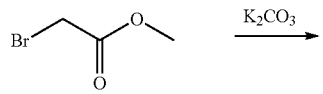

-continued

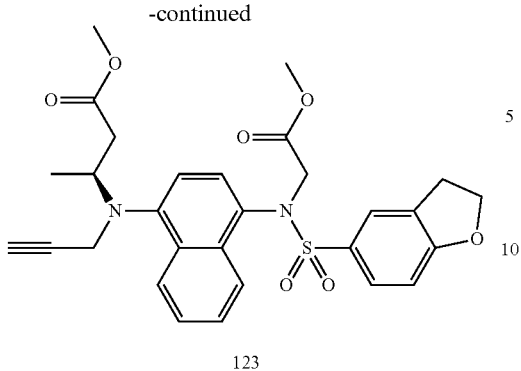

123

In the same way as the synthesis method of compound 49, reaction is performed on compound 122 (0.10 g, 0.21 mmol), methyl bromoacetate (38.56 mg, 0.25 mmol) and K$_2$CO$_3$ (86.94 mg, 0.63 mmol) as starting materials to obtain a pale yellow solid 123 of 68.21 mg with yield of 60%; ESI-MS 551.2 [M+H]$^+$.

Synthesis of (S)-3-((4-((2,3-dihydrobenzofuran)-5-sulfonamido) naphthalen-1-yl) (prop-2-yn-1-yl) amino) butanoic acid (DDO-1222)

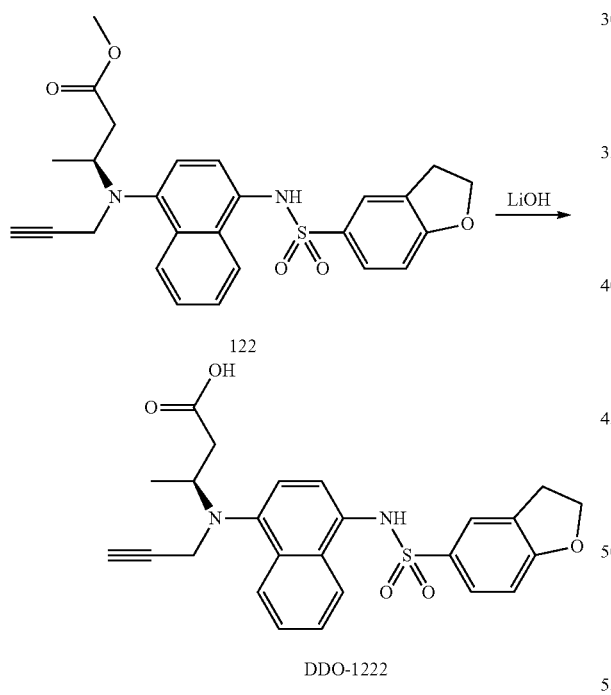

In the same way as the synthesis method of compound DDO-1160, reaction is performed on compound 122 (0.10 mg, 0.21 mmol) and 2M aqueous LiOH (1.00 mL, 2.00 mmol) as starting materials to obtain a white solid DDO-1222 of 57.00 mg with yield of 58%; $^1$H NMR (300 MHz, DMSO-d$_6$) δ 12.15 (s, 1H), 9.85 (s, 1H), 8.22-8.12 (m, 1H), 8.06-7.99 (m, 1H), 7.50-7.41 (m, 4H), 7.28 (d, J=8.1 Hz, 1H), 7.07-7.00 (m, 1H), 6.81 (dd, J=8.3, 2.9 Hz, 1H), 4.59 (t, J=8.8 Hz, 2H), 4.02-3.83 (m, 2H), 3.70 (p, J=5.1, 4.6 Hz, 1H), 3.13 (t, J=8.8 Hz, 2H), 2.95 (s, 1H), 2.61-2.52 (m, 1H), 2.34 (dd, J=15.1, 9.3 Hz, 1H), 1.23-1.14 (m, 3H); HRMS (ESI): found 465.1476. (C$_{25}$H$_{24}$N$_2$O$_5$S, [M+H]$^+$, requires 465.1479); HPLC (85:15 methanol:water with 1‰ TFA): t$_R$=8.27 min, 98.79%.

Synthesis of (S)-3-((4-((N-(Carboxymethyl)-2,3-dihydrobenzofuran)-5-sulfonamido) naphthalen-1-yl)(prop-2-yn-1-yl) amino) butanoic acid (DDO-1223)

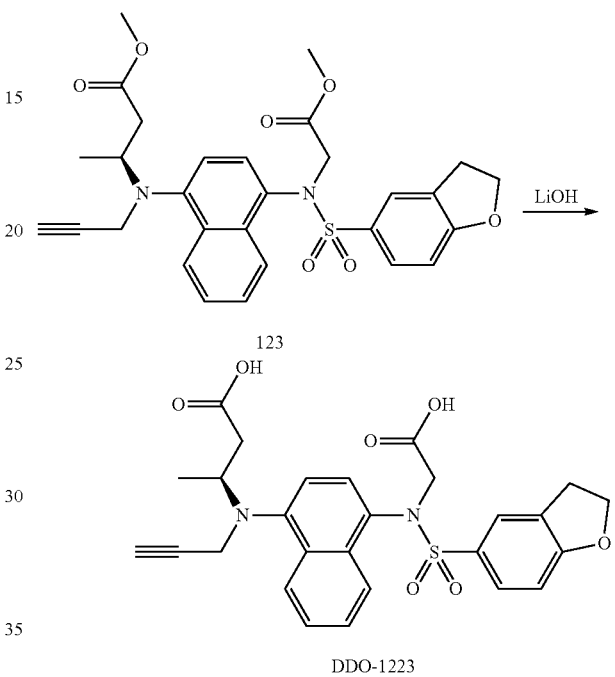

In the same way as the synthesis method of compound DDO-1161, reaction is performed on compound 123 (68.21 tug, 0.12 mmol) and 2M aqueous (1.50 mL, 3.00 mmol) as starting materials to obtain a white solid DDO-1223 of 49.30 mg with yield of 79%; $^1$H NMR (300 MHz, DMSO-d$_6$) δ 12.43 (s, 2H), 8.20-8.07 (m, 2H), 7.56-7.48 (m, 2H), 7.46 (d, J=7.7 Hz, 1H), 7.36 (dq, J=8.7, 3.0, 2.6 Hz, 1H), 7.28 (d, J=8.1 Hz, 1H), 7.15-7.08 (m, 1H), 6.85 (d, J=9.0 Hz, 1H), 4.65 (t, J=8.9 Hz, 2H), 4.46-4.32 (m, 2H), 4.08-3.88 (m, 2H), 3.76 (d, J=7.1 Hz, 1H), 3.19 (t, J=8.9 Hz, 2H), 3.00 (d, J=2.6 Hz, 1H), 2.59 (ddd, J=15.0, 7.7, 4.4 Hz, 1H), 2.39 (dd, J=15.1, 9.2 Hz, 1H), 1.27-1.14 (m, 3H); HRMS(ESI): found 523.1530 (C$_{25}$H$_{24}$N$_2$O$_5$S, [M+H]$^+$, requires 523.1533); HPLC (85:15 methanol:water with 1‰ TFA): t$_R$=8.10 min, 99.18%.

Example 2: Activity Testing of Compounds

1. Keap1-Nrf2 PPI Competitive Inhibition Test Based on Fluorescence Polarization (FP Experiment)

The 384-well blackboard model 3676 produced by Corning is used in FP experiment, with a total volume of reaction of 40 µL. 20 µL compound, 10 µL 4 nm FITC labeled Nrf2 9 peptide, 10 µL 12 nm Keap1 kelch domain protein are added to the well in order. 20 µL 200 nM DDO-1002, 10 µL 4 nM of the FITC-labeled Nrf2 9 peptide, 10 µL 12 nM of Keap1 Ketch domain protein are used in the positive control; 20 µL HEPES buffer, 10 µL 4 nM of the FITC-labeled Nrf2 9 peptide, 10 µL, 12 nM of Keap1 Kelch domain protein are used in the negative control; 10 μL 4 nM of the FITC-labeled Nrf2 9 peptide, 30 μL of HEPES buffer are used in the blank control. After addition is complete, they are incubated for 30 min at room temperature. The detection instrument is a SpectraMax Multi-Mode Microplate Reader (Molecular Devices), the excitation light wavelength selected is 485 nm, the emission light wavelength is 545 nm, and the fluorescence intensity in the horizontal and vertical directions is detected to calculate the polarization value. The inhibition rate is calculated as: inhibition $\% = (P_{obs} - P_{min})/(P_{max} - P_{min})$ wherein $P_{obs}$ is the polarization value of the compound well, $P_{max}$ is the polarization value of the negative control well, and $P_{min}$ is the polarization value of the blank well. Data treatment is performed using GraphPad Prism, and $IC_{50}$ of the compound is calculated using a concentration-inhibition rate curve. The $IC_{50}$ values for each compound are as previously described.

2. ARE Luciferase Reporter Gene Experiment

HepG2-ARE-C8 cells in log growth phase (these cells are given by A. N. Tony Kong of Rutgers University) are digested with 0.1% pancreatin to prepare a cell suspension, the cell suspension is added to a 96-well microtiter plate at a cell concentration of $4 \times 10^5$/mL, added 100 μL per well, and after overnight culture, a DMSO group serves as a negative control, t-BHQ serves as a positive control, and a cell culture lysis reagent serves as a background value. The compound is allowed to act for 12 h, three replicate wells were provided, the growth medium is carefully pipetted from the cells to be examined, 100 μL of pre-cooled. PBS is added to rinse the cells, 5× lysis buffer (1× buffer is equilibrated at room temperature before use) diluted beforehand was added after removal, added 30 μL per well, lysed on ice for 15 min, 20 μL of supernatant is pipetted into a luminoskan ascent (Thermo scientific, USA) for detection. 100 μL luciferase detection reagent is added to each well and read immediately. The light intensity of the present reaction can remain stable over a period of approximately 1 minute, followed by a slow decay with a half-life of approximately 10 minutes. Typical delay time is 2 seconds, typical reading time is 10 seconds, and the last measured data is divided from the DMSO group. The larger the obtained ratio is, the better the inducibility is.

By a fluorescence polarization based Keap1-Nrf2 PPI competitive inhibition experiment we have shown that on the target level, some compounds (compound numbers see FIG. 1) are able to efficiently compete for binding to Keap1 and thereby activating Nrf2. In order to further verify whether the series of compounds can effectively activate Nrf2 at the cell level, we select compounds with better activity (see FIG. 1) for testing using the ARE luciferase reporter assay (positive drugs t-BHQ). An ARE luciferase reporter assay. The basic principle of the assay is to insert an ARE gene into a plasmid in front of a luciferase expression sequence and transfect same to cells, so that the cells stably express the plasmid. When a small molecule activates Nrf2, Nrf2 can enter the nucleus and bind to ARE, and then up-regulate the expression of luciferase. When luciferin is present in a substrate, the luciferin can oxidize the luciferin to emit fluorescence, and the activation capability of a compound on Nrf2 is indirectly reflected by means of fluorescence intensity. FIG. 1 is a luciferase reporter assay result.

It can be determined from FIG. 1 that all the selected compounds can up-regulate the expression of Nrf2 to a certain extent. In the FP assay, the compound DDO-1221 having the optimal target activity does not have the optimal cell activity, and DDO-1220 having the optimal single acid form has the optimal cell activity. The membrane permeability is superior to that of the double acid form because the single acid form has a small molecular polarity.

Although the present invention has been described by means of some exemplary embodiments, it should be understood by those skilled in the art that the scope of the present invention should not be limited thereto.

The invention claimed is:

1. A naphthalenesulfonamide compound, wherein chemical structure is represented by formula I, II, III, IV, V or VI:

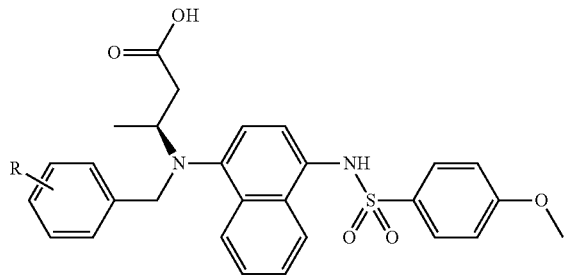

I

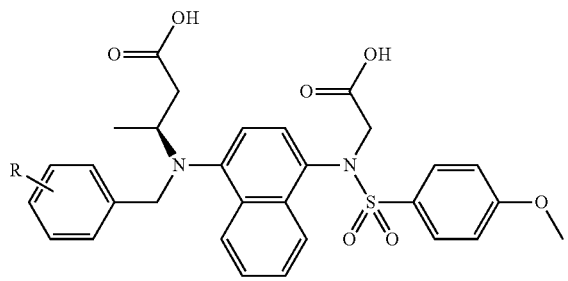

II wherein, in the formula I or II, a substituent R is:

| Formula I-number | Substituent R | Formula II-number | Substituent R |
|---|---|---|---|
| DDO-1160 | —H | DDO-1161 | —H |
| DDO-1162 | 4-CH$_3$ | DDO-1163 | 4-CH$_3$ |
| DDO-1164 | 4-Cl | DDO-1165 | 4-Cl |
| DDO-1166 | 4-F | DDO-1167 | 4-F |
| DDO-1168 | 3-CH$_3$ | DDO-1169 | 3-CH$_3$ |
| DDO-1170 | 2-CH$_3$ | DDO-1171 | 2-CH$_3$ |
| DDO-1172 | 3-Cl | DDO-1173 | 3-Cl |
| DDO-1174 | 2-Cl | DDO-1175 | 2-Cl |
| DDO-1176 | 3-F | DDO-1177 | 3-F |
| DDO-1178 | 2-F | DDO-1179 | 2-F |

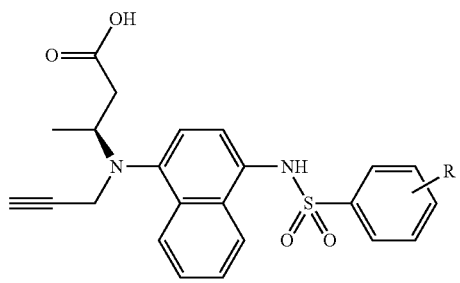

III

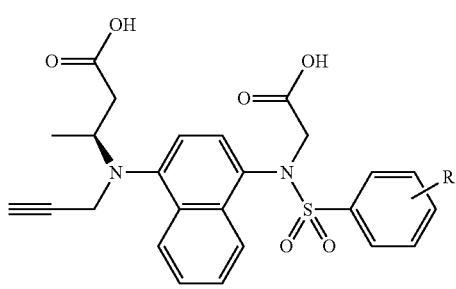

IV wherein, in the formula III or IV, a substituent R is:

| Formula III-number | Substituent R | Formula IIV-number | Substituent R |
|---|---|---|---|
| DDO-1186 | H | DDO-1187 | H |
| DDO-1188 | 4-NHCOCH$_3$ | DDO-1189 | 4-NHCOCH$_3$ |
| DDO-1180 | 4-OCH$_3$ | DDO-1181 | 4-OCH$_3$ |
| DDO-1190 | 4-F | DDO-1191 | 4-F |
| DDO-1192 | 4-Cl | DDO-1193 | 4-Cl |
| DDO-1194 | 4-CH(CH$_3$)$_2$ | DDO-1195 | 4-CH(CH$_3$)$_2$ |
| DDO-1196 | 4-CH$_3$ | DDO-1197 | 4-CH$_3$ |
| DDO-1198 | 2-OCH$_3$ | DDO-1199 | 2-OCH$_3$ |
| DDO-1200 | 3-OCH$_3$ | DDO-1201 | 3-OCH$_3$ |
| DDO-1202 | 2-CH$_3$ | DDO-1203 | 2-CH$_3$ |
| DDO-1204 | 2,4-CH$_3$ | DDO-1205 | 2,4-CH$_3$ |
| DDO-1206 | 2,4,6-CH$_3$ | DDO-1207 | 2,4,6-CH$_3$ |
| DDO-1208 | 2,3,5,6-CH$_3$ | DDO-1209 | 2,3,5,6-CH$_3$ |

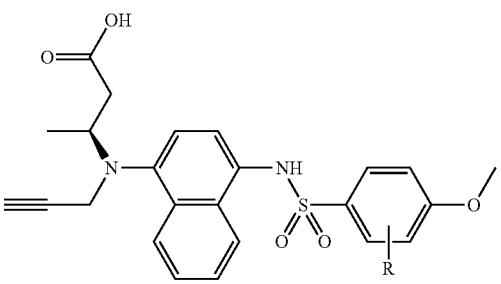

V

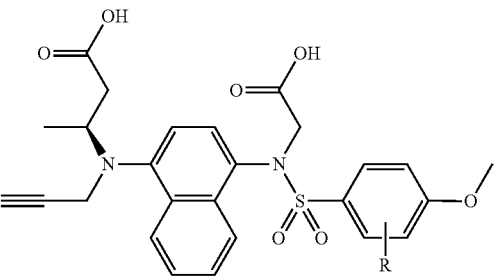

VI wherein, in the formula V or VI, a substituent R is:

| Formula V-number | Substituent R | Formula VI-number | Substituent R |
|---|---|---|---|
| DDO-1210 | 3-OMe | DDO-1211 | 3-OMe |
| DDO-1212 | 3-F | DDO-1213 | 3-F |
| DDO-1214 | 3-Cl | DDO-1215 | 3-Cl |
| DDO-1216 | 3-Me | DDO-1217 | 3-Me |
| DDO-1218 | 2,3,6-3Me | DDO-1219 | 2,3,6-3Me |
| DDO-1220 | 2,6-2Me | DDO-1221 | 2,6-2Me |
| DDO-1222 | (2,3-dihydrobenzofuran-5-yl) | DDO-1223 | (2,3-dihydrobenzofuran-5-yl) |

2. A method for preparing a compound represented by the formula I or II according to claim 1, comprising following steps:

performing nucleophilic substitution with 1-nitronaphthalene as a raw material to obtain a compound 18, and then reacting the compound 18 with Tf$_2$O (triflic anhydride) to obtain a compound 19 having an easy leaving group; performing Buchwald-Hartwig C—N coupling reaction on the compound 19 and (S)-methyl aminobutyrate hydrochloride to obtain an intermediate 20; performing nitro reduction on the intermediate 20 in the presence of Pd/C and H$_2$ to obtain an intermediate 21; reacting the intermediate 21 with di-tert-butyl dicarbonate to obtain an intermediate 22; reacting the intermediate 22 with benzyl bromide in the presence of K$_2$CO$_3$ and NaI to obtain an intermediate 23; removing Boc (t-butyloxy carbonyl) of the intermediate 23 with trifluoroacetic acid to an intermediate 24, and reacting the intermediate 24 with 4-methoxybenzene sulfonyl chloride to obtain a key intermediate 25; and reacting the intermediate 25 with methyl bromoacetate in the presence of K$_2$CO$_3$ to obtain a compound 26, and demethylating the compound 26 in the presence of LiOH to obtain a diacid compound of the formula II, or demethylating the intermediate 25 in the presence of LiOH to obtain a mono-acid compound of the formula I; a synthetic route is as follows:

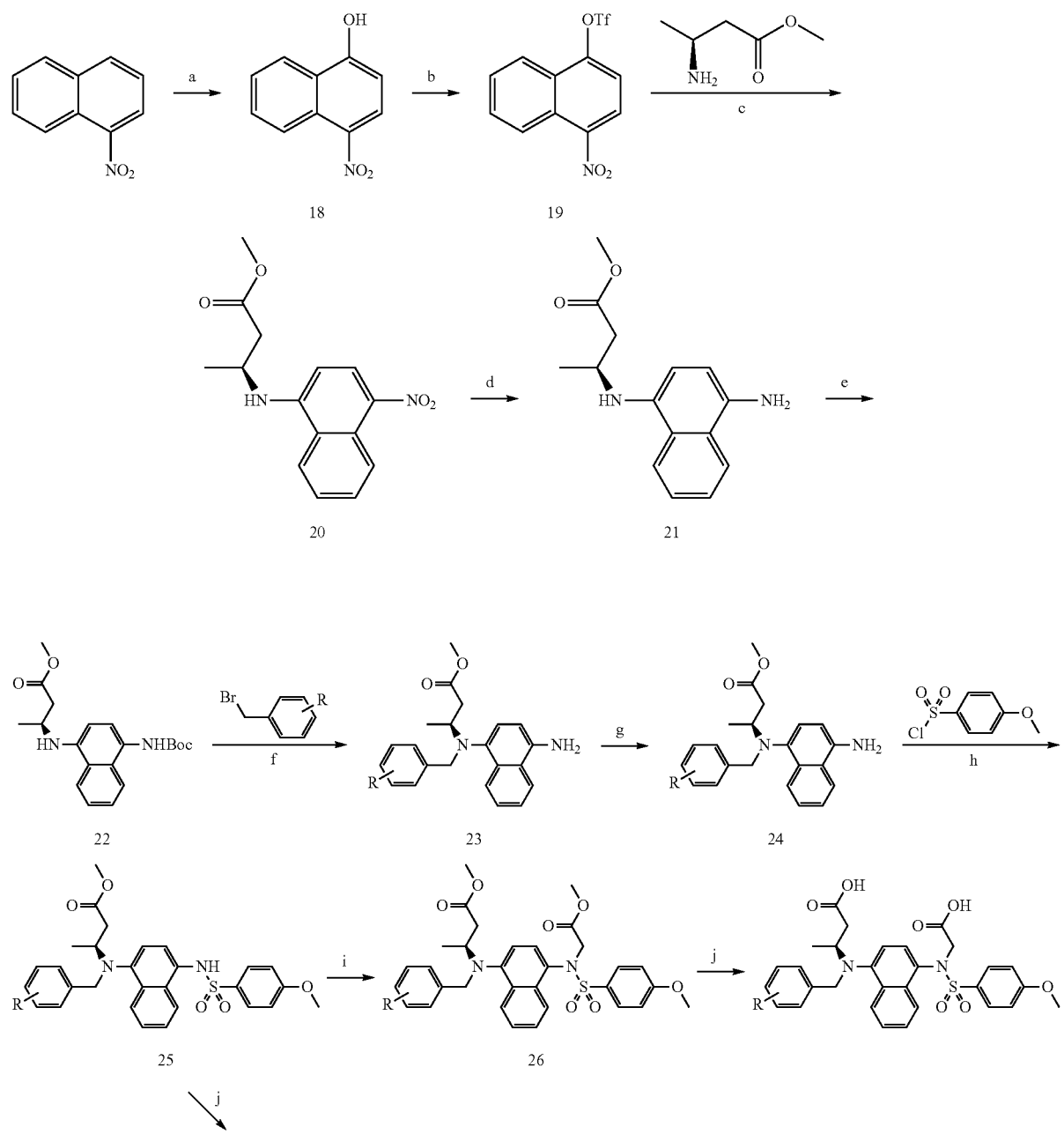

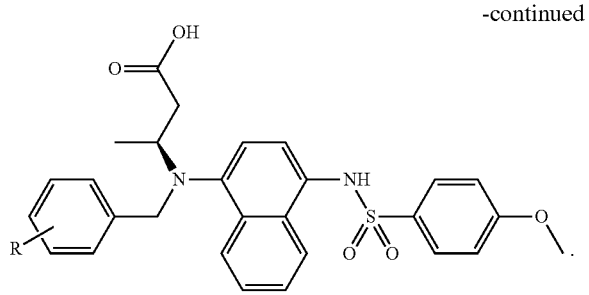

3. A method for preparing a compound represented by the formula III or IV according to claim 1, comprising following steps:

performing nucleophilic substitution with 1-nitronaphthalene as a raw material to obtain a compound 18, and then reacting the compound 18 with Tf$_2$O (triflic anhydride) to obtain a compound 19 having an easy leaving group; performing Buchwald-Hartwig C—N coupling reaction on the compound 19 and (S)-methyl aminobutyrate hydrochloride to obtain an intermediate 20; performing nitro reduction on the intermediate 20 in the presence of Pd/C and H$_2$ to obtain an intermediate 21; reacting the intermediate 21 with di-tert-butyl dicarbonate to obtain an intermediate 22; reacting the intermediate 22 with propargyl bromide in the presence of K$_2$CO$_3$ and NaI to obtain an intermediate 35; removing Boc (t-butyloxy carbonyl) of the intermediate 35 with trifluoroacetic acid to an intermediate 36, and reacting the intermediate 36 with benzene sulfonyl chloride with different substituents to obtain a key intermediate 37; and reacting the intermediate 37 with methyl bromoacetate in the presence of K$_2$CO$_3$ to obtain a compound 38, and demethylating the compound 38 in the presence of LiOH to obtain a diacid compound of the formula IV, or demethylating the intermediate 37 in the presence of LiOH to obtain a mono-acid compound of the formula III; a synthetic route is as follows:

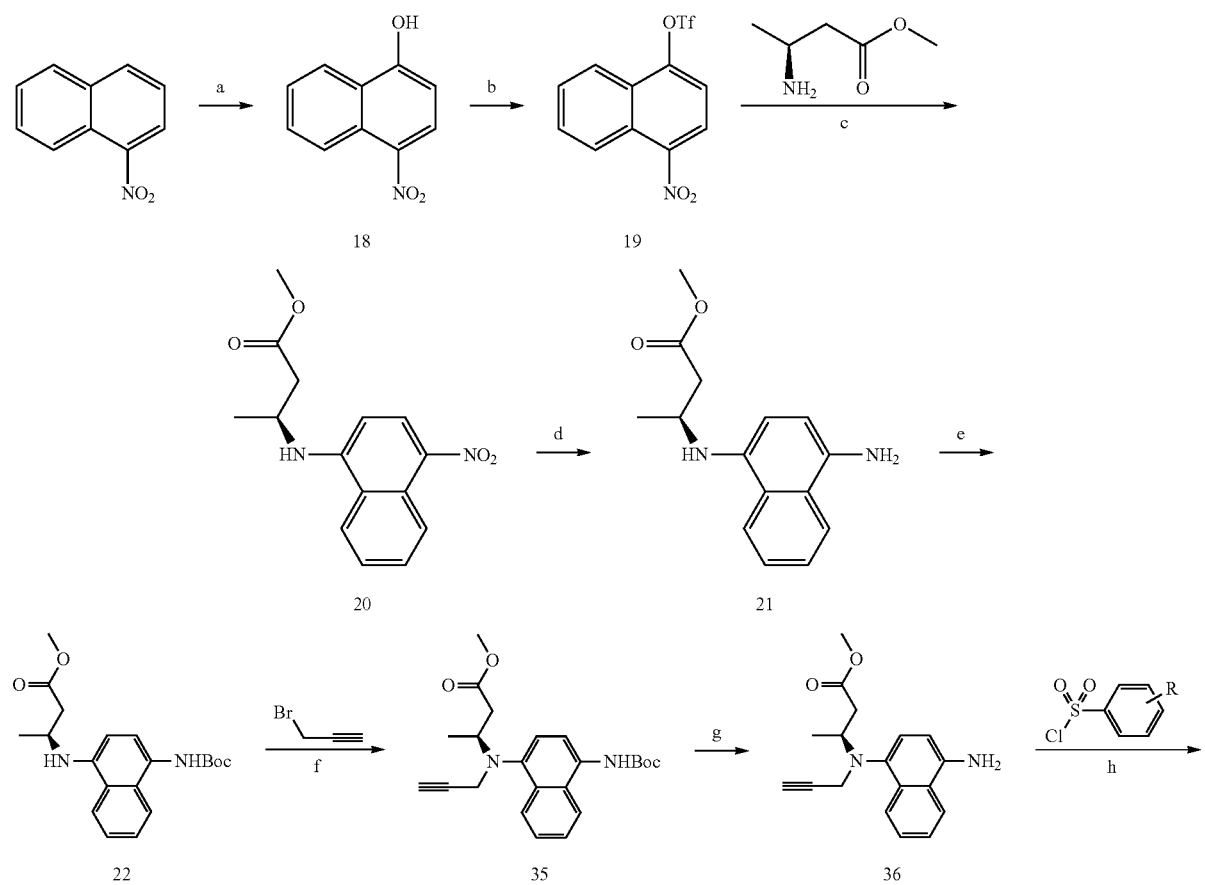

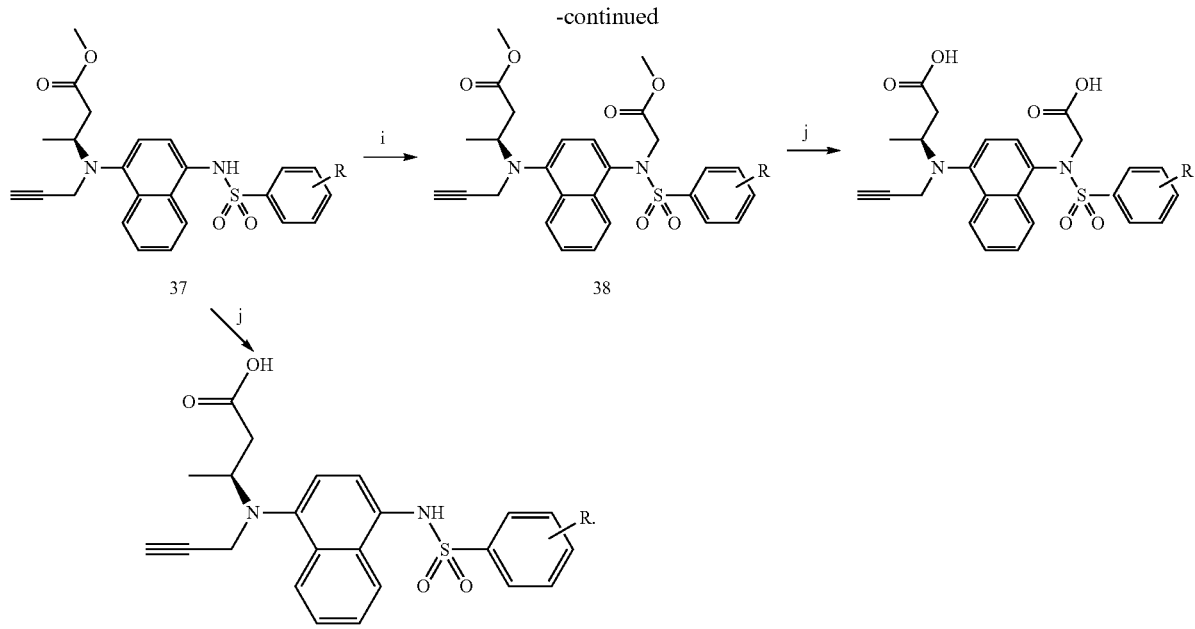

4. A method for preparing a compound represented by the formula V or VI according to claim 1, comprising following steps:

performing nucleophilic substitution with 1-nitronaphthalene as a raw material to obtain a compound 18, and then reacting the compound 18 with Tf₂O (triflic anhydride) to obtain a compound 19 having an easy leaving group; performing Buchwald-Hartwig C—N coupling reaction on the compound 19 and (S)-methyl aminobutyrate hydrochloride to obtain an intermediate 20; performing nitro reduction on the intermediate 20 in the presence of Pd/C and H₂ to obtain an intermediate 21; reacting the intermediate 21 with di-tert-butyl dicarbonate to obtain an intermediate 22; reacting the intermediate 22 with propargyl bromide in the presence of K₂CO₃ and NaI to obtain an intermediate 35; removing Boc (t-butyloxy carbonyl) of the intermediate 35 with trifluoroacetic acid to an intermediate 36, and reacting the intermediate 36 with 4-methoxybenzenesulfonyl chloride with different substituents to obtain a key intermediate 39; and reacting the intermediate 39 with methyl bromoacetate in the presence of K₂CO₃ to obtain a compound 40, and demethylating the compound 40 in the presence of LiOH to obtain a diacid compound of the formula VI, or demethylating the intermediate 39 in the presence of LiOH to obtain a mono-acid compound of the formula V; a synthetic route is as follows:

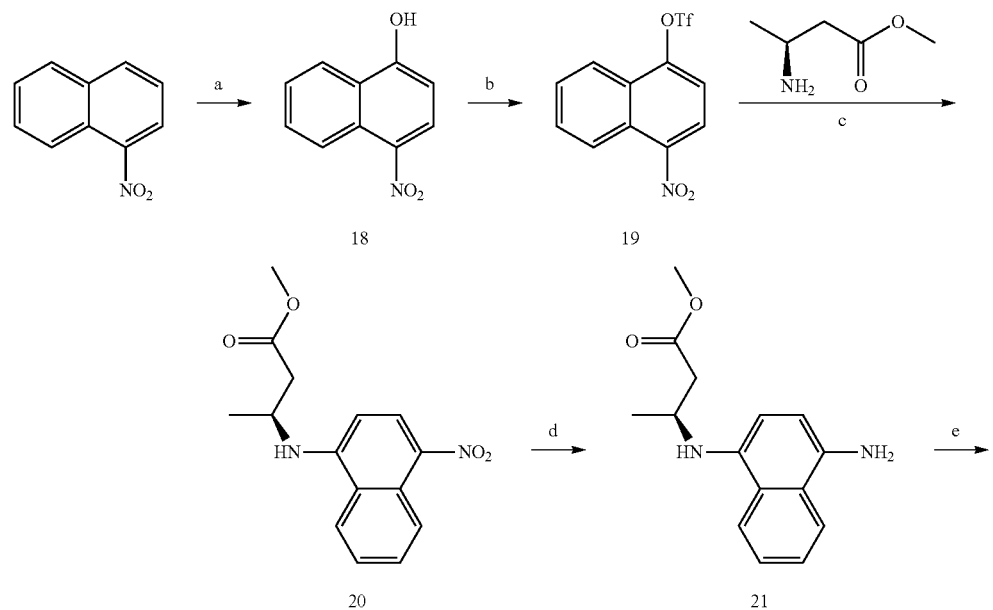

-continued

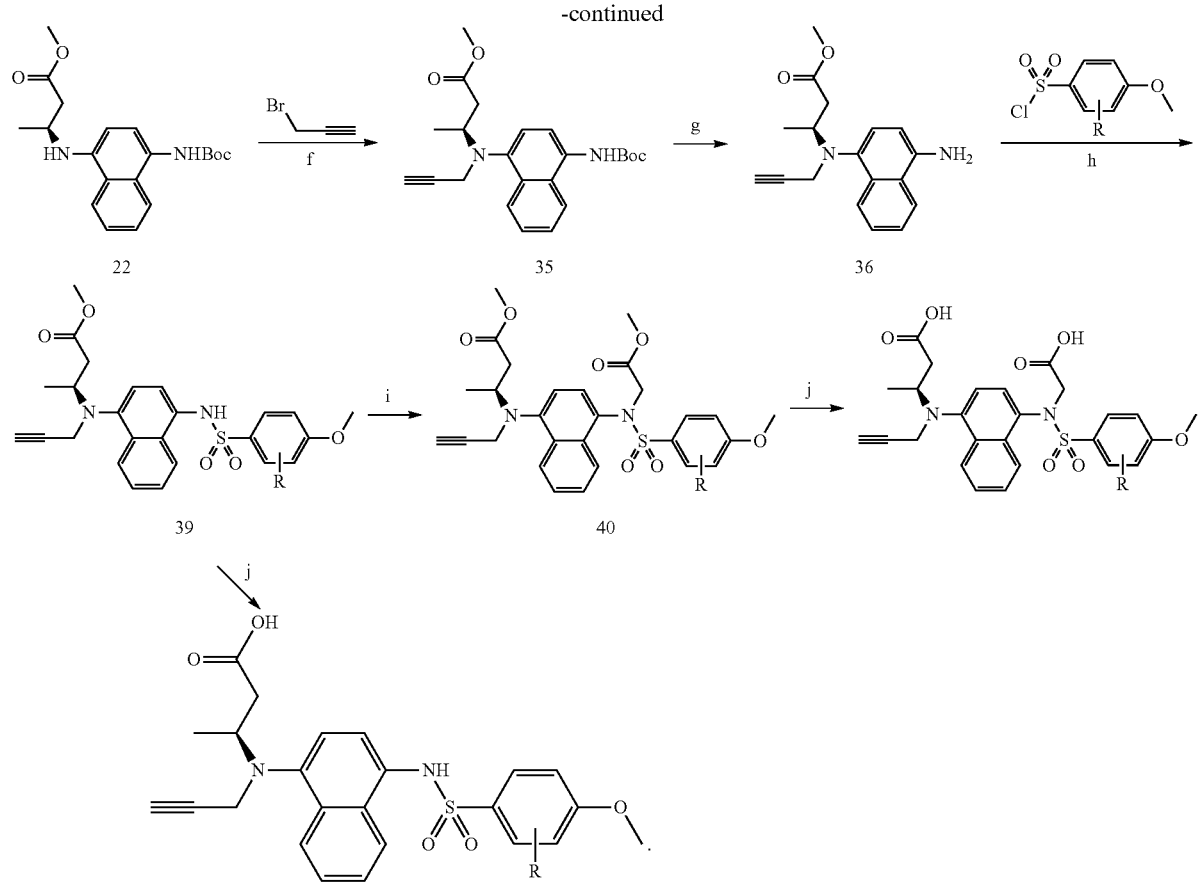

5. A pharmaceutically acceptable salt of the naphthalenesulfonamide compound according to claim 1.

6. A method of the naphthalenesulfonamide compound according to claim 1 and a pharmaceutically acceptable salt thereof in preparation of a Keap1-Nrf2 protein-protein interaction inhibitor.

7. A method of the naphthalenesulfonamide compound according to claim 1 and a pharmaceutically acceptable salt thereof in preparation of a drug for increasing an antioxidant capacity under an oxidative stress state.

* * * * *